US006846487B2

(12) United States Patent
Rosey et al.

(10) Patent No.: US 6,846,487 B2
(45) Date of Patent: Jan. 25, 2005

(54) **THERAPEUTIC COMPOSITIONS FOR TREATING INFECTION BY *LAWSONIA* SPP.**

(75) Inventors: Everett Lee Rosey, Preston, CT (US); Kendall Wayne King, Waterford, CT (US); Robert Trygve Good, Romsey (AU); Richard Anthony Strugnell, Hawthorn (AU)

(73) Assignees: Pfizer Inc., New York, NY (US); Agriculture Victoria Services Pty Ltd. (AU); Austrailian Pork Limited (AU)

( * ) Notice: Subject to any disclaimer, the term of this patent is extended or adjusted under 35 U.S.C. 154(b) by 0 days.

(21) Appl. No.: 10/010,160

(22) Filed: Nov. 9, 2001

(65) Prior Publication Data

US 2003/0103999 A1 Jun. 5, 2003

Related U.S. Application Data

(60) Provisional application No. 60/249,596, filed on Nov. 17, 2000.

(30) Foreign Application Priority Data

Nov. 10, 2000 (AU) .............................................. PR1381

(51) Int. Cl.[7] ...................... A61K 39/02; A61K 39/118; C07K 1/00; C12P 21/02; C12N 15/09
(52) U.S. Cl. ............................... 424/190.1; 424/184.1; 424/185.1; 424/263.1; 530/350; 435/69.3; 435/252.3; 435/320.1; 536/23.1; 536/23.2; 536/23.7
(58) Field of Search ........................... 424/190.1, 185.1, 424/184.1, 263.1; 530/350; 435/69.3, 252.3, 320.1; 536/23.1, 23.2, 23.7

(56) References Cited

FOREIGN PATENT DOCUMENTS

WO WO 96/39629 12/1996
WO WO 97/20040 6/1997

OTHER PUBLICATIONS

Rudinger et al, in "Peptide Hormones", edited by Parsons, J.A., University Park Press, Jun. 1976, p. 6.*
Burgess et al., The Journal of Cell Biology, 111:2129–2138, 1990.*
Lazar et al., Molecular and Cellular Biology, 8(3): 1247–1252, 1988.*
Jobling et al. (Mol. Microbiol, 1991, 5(7): 1755–67.*
Ellis, R.W. (Chapter 29 of "Vaccines" Plotkin, 5.A. et al. (eds) published by W. B. 5aunders company (Philadelphia) in 1988, especially p. 571.*
Boye et al., *Specific Detection of Lawsonia intracellularis in Porcine Proliferation Enteropathy Infered from Fluorecent rRNA In Situ Hybridization*, Vet Pathol 35:153–156 (1998).

* cited by examiner

Primary Examiner—Lynette R. F. Smith
Assistant Examiner—Padma Baskar
(74) Attorney, Agent, or Firm—Lorraine B. Ling; Kenneth I. Kohn; Kohn & Associates, PLLC

(57) ABSTRACT

The present invention relates generally to therapeutic compositions for the treatment and/or prophylaxis of intestinal disease conditions in animals and birds caused or exacerbated by *Lawsonia intracellularis* or similar or otherwise related microorganism. In particular, the present invention provides a novel gene derived from *Lawsonia intracellularis*, which encodes an immunogenic polypeptide that is particularly useful as an antigen in a vaccine preparation for conferring humoral immunity against *Lawsonia intracellularis* and related pathogens in animal hosts, wherein said polypeptide is selected from the group consisting of flhB, fliR, ntrC, glnH, motA, motB, tlyC, ytfM, and ytfN polypeptides, or a homologue, analogue or derivative of any one or more of said polypeptides. The present invention is also directed to methods for the treatment and/or prophylaxis of such intestinal disease conditions and to diagnostic agents and procedures for detecting *Lawsonia intracellularis* or similar or otherwise related microorganisms.

5 Claims, 1 Drawing Sheet

US 6,846,487 B2

THERAPEUTIC COMPOSITIONS FOR TREATING INFECTION BY *LAWSONIA* SPP.

RELATED APPLICATION DATA

This application claims benefit of priority from Australian Patent Application No. PR1381 filed on Nov. 10, 2000, and from U.S. patent application Ser. No. 60/249,596 filed on Nov. 17, 2000.

FIELD OF THE INVENTION

The present invention relates generally to therapeutic compositions for the treatment and/or prophylaxis of intestinal disease conditions in animals and birds caused or exacerbated by *Lawsonia intracellularis* or similar or otherwise related microorganism. In particular, the present invention provides a novel gene derived from *L. intracellularis* which encodes an immunogenic polypeptide. The polypeptide described herein, selected from the group consisting of flhB, fliR, ntrC, glnH, motA, motB, tlyC, ytfM, and ytfN polypeptides, or a homologue, analogue or derivative of any one or more of said polypeptides, is particularly useful as an antigen in vaccine preparation for conferring humoral immunity against *L. intracellularis* and related pathogens in animal hosts. The present invention is also directed to methods for the treatment and/or prophylaxis of such intestinal disease conditions and to diagnostic agents and procedures for detecting *L. intracellularis* or similar or otherwise related microorganisms.

GENERAL

Bibliographic details of the publications numerically referred to in this specification are collected at the end of the description. All patents, patent applications, and publications cited herein are incorporated by reference in their entirety.

Reference hereinafter to "*Lawsonia intracellularis*" or its abbreviation "*L. intracellularis*" includes all microorganisms similar to or otherwise related to this microorganism, as described by Stills (1991) or Jones et al. (1997) or Lawson et al. (1993) or McOrist et al. (1995).

References herein to "AGAL" shall be taken to mean a reference to the Australian Government Analytical Laboratories located at 1 Suakin Street, Pymble, New South Wales 2073, Australia. All biological deposits referred to herein in respect of the plasmids assigned AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); and NM00/16482 (plasmid pGTE#7 ytfM); and NM01/23286 (plasmid pGTE#8 ytfN) have been made under the provisions of the Budapest Treaty on the International Recognition of the Deposit of Microorganisms for the Purposes of Patent Procedure.

As used herein, the word "flhB", or the term "flhB gene", shall be taken to refer to a gene encoding the antigenic flhB polypeptide of the present invention, which gene comprises the nucleotide sequence set forth in SEQ ID NO: 1 or the nucleotide sequence of the *L. intracellularis* gene contained in the plasmid pGTE#2 which has been deposited under AGAL Accession No. NM00/16477. The word "flhB" or the term "flhB gene" shall further be taken to include a degenerate or complementary nucleotide sequence to SEQ ID NO: 1 or the nucleotide sequence of the *L. intracellularis* gene contained in the plasmid pGTE#2 which has been deposited under AGAL Accession No. NM00/16477. It shall also be understood that the term "flhB polypeptide" refers to a polypeptide of the invention which comprises the amino acid sequence set forth in SEQ ID NO: 2 or a polypeptide encoded by the *L. intracellularis* gene contained in the plasmid pGTE#2 which has been deposited under AGAL Accession No. NM00/16477. The term "flhB polypeptide" shall further be taken to include a polypeptide which is functionally-related to or immunologically cross-reactive with the polypeptide of SEQ ID NO: 2 or a polypeptide encoded by the *L. intracellularis* gene contained in the plasmid pGTE#2 which has been deposited under AGAL Accession No. NM00/16477.

As used herein, the word "fliR", or the term "fliR gene", shall be taken to refer to a gene encoding the antigenic fliR polypeptide of the present invention, which gene comprises the nucleotide sequence set forth in SEQ ID NO: 3 or the nucleotide sequence of the *L. intracellularis* gene contained in the plasmid pGTE#3 which has been deposited under AGAL Accession No.NM00/16478. The word "fliR" or the term "fliR gene" shall further be taken to include a degenerate or complementary nucleotide sequence to SEQ ID NO: 3, or the nucleotide sequence of the *L. intracellularis* gene contained in the plasmid pGTE#3 which has been deposited under AGAL Accession No.NM00/16478. It shall also be understood that the term "fliR polypeptide" refers to a polypeptide of the invention which comprises the amino acid sequence set forth in SEQ ID NO: 4 or a polypeptide encoded by the *L. intracellularis* gene contained in the plasmid pGTE#3 which has been deposited under AGAL Accession No.NM00/16478. The term "fliR polypeptide" shall further be taken to include a polypeptide which is functionally-related to or immunologically cross-reactive with the polypeptide of SEQ ID NO: 4 or a polypeptide encoded by the *L. intracellularis* gene contained in the plasmid pGTE#3 which has been deposited under AGAL Accession No.NM00/16478.

As used herein, the word "ntrC", or the term "ntrC gene", shall be taken to refer to a gene encoding the antigenic ntrC polypeptide of the present invention, which gene comprises the nucleotide sequence set forth in SEQ ID NO: 5 or the nucleotide sequence of the *L. intracellularis* gene contained in the plasmid pGTE#6 which has been deposited under AGAL Accession No.NM00/16481. The word "ntrC" or the term "ntrC gene" shall further be taken to include a degenerate or complementary nucleotide sequence to SEQ ID NO: 5, or the nucleotide sequence of the *L. intracellularis* gene contained in the plasmid pGTE#6 which has been deposited under AGAL Accession No.NM00/16481. It shall also be understood that the term "ntrC polypeptide" refers to a polypeptide of the invention which comprises the amino acid sequence set forth in SEQ ID NO: 6 or a polypeptide encoded by the *L. intracellularis* gene contained in the plasmid pGTE#6 which has been deposited under AGAL Accession No.NM00/16481. The term "ntrC polypeptide" shall further be taken to include a polypeptide which is functionally-related to or immunologically cross-reactive with the polypeptide of SEQ ID NO: 6 or a polypeptide encoded by the *L. intracellularis* gene contained in the plasmid pGTE#6 which has been deposited under AGAL Accession No.NM00/16481.

As used herein, the word "glnH", or the term "glnH gene", shall be taken to refer to a gene encoding the antigenic glnH polypeptide of the present invention, which gene comprises the nucleotide sequence set forth in SEQ ID NO: 7 or the nucleotide sequence of the *L. intracellularis* gene contained in the plasmid pGTE#1 which has been deposited under AGAL Accession No.NM00/16476. The word "glnH" or the term "glnH gene" shall further be taken to include a degenerate or complementary nucleotide sequence to SEQ ID NO: 7, or the nucleotide sequence of the *L. intracellularis* gene contained in the plasmid pGTE#1 which has been deposited under AGAL Accession No.NM00/16476. It shall also be understood that the term "glnH polypeptide" refers to a polypeptide of the invention which comprises the amino acid sequence set forth in SEQ ID NO: 8 or a polypeptide encoded by the *L. intracellularis* gene contained in the plasmid pGTE#1 which has been deposited under AGAL Accession No.NM00/16476. The term "glnH polypeptide" shall further be taken to include a polypeptide which is functionally-related to or immunologically cross-reactive with the polypeptide of SEQ ID NO: 8 or a polypeptide encoded by the *L. intracellularis* gene contained in the plasmid pGTE#1 which has been deposited under AGAL Accession No.NM00/16476.

As used herein, the word "motA", or the term "motA gene", shall be taken to refer to a gene encoding the antigenic motA polypeptide of the present invention, which gene comprises the nucleotide sequence set forth in SEQ ID NO: 9, or to the nucleotide sequence of the *L. intracellularis* gene contained in the plasmid pGTE#4 which has been deposited under AGAL Accession No.NM00/16479 and which has homology to SEQ ID NO: 9. The word "motA" or the term "motA gene" shall further be taken to include a degenerate or complementary nucleotide sequence to SEQ ID NO: 9, or the nucleotide sequence of the *L. intracellularis* gene contained in the plasmid pGTE#4 which has been deposited under AGAL Accession No.NM00/16479 and which has homology to SEQ ID NO: 9. It shall also be understood that the term "motA polypeptide" refers to a polypeptide of the invention which comprises the amino acid sequence set forth in SEQ ID NO: 10 or a polypeptide encoded by the *L. intracellularis* gene contained in the plasmid pGTE#4 which has been deposited under AGAL Accession No.NM00/16479 and which has homology to SEQ ID NO: 9. The term "motA polypeptide" shall further be taken to include a polypeptide which is functionally-related to or immunologically cross-reactive with the polypeptide of SEQ ID NO: 10 or a polypeptide encoded by the *L. intracellularis* gene contained in the plasmid pGTE#4 which has been deposited under AGAL Accession No.NM00/16479 and having homology to SEQ ID NO: 9.

As used herein, the word "motB", or the term "motB gene", shall be taken to refer to a gene encoding the antigenic motB polypeptide of the present invention, which gene comprises the nucleotide sequence set forth in SEQ ID NO: 11 or the nucleotide sequence of the *L. intracellularis* gene contained in the plasmid pGTE#4 which has been deposited under AGAL Accession No.NM00/16479 and having homology to SEQ ID NO: 11. The word "motB" or the term "motB gene" shall further be taken to include a degenerate or complementary nucleotide sequence to SEQ ID NO: 11, or the nucleotide sequence of the *L. intracellularis* gene contained in the plasmid pGTE#4 which has been deposited under AGAL Accession No.NM00/16479 and having homology to SEQ ID NO: 11. It shall also be understood that the term "motB polypeptide" refers to a polypeptide of the invention which comprises the amino acid sequence set forth in SEQ ID NO: 12 or a polypeptide encoded by the *L. intracellularis* gene contained in the plasmid pGTE#4 which has been deposited under AGAL Accession No.NM00/16479 and having homology to SEQ ID NO: 11. The term "motB polypeptide" shall further be taken to include a polypeptide which is functionally-related to or immunologically cross-reactive with the polypeptide of SEQ ID NO: 12 or a polypeptide encoded by the *L. intracellularis* gene contained in the plasmid pGTE#4 which has been deposited under AGAL Accession No.NM00/16479 and having homology to SEQ ID NO: 11.

As used herein, the word "tlyC", or the term "tlyC gene", shall be taken to refer to a gene encoding the antigenic tlyC polypeptide of the present invention, which gene comprises the nucleotide sequence set forth in SEQ ID NO: 13 or the nucleotide sequence of the *L. intracellularis* gene contained in the plasmid pGTE#5 which has been deposited under AGAL Accession No.NM00/16480. The word "tlyC" or the term "tlyC gene" shall further be taken to include a degenerate or complementary nucleotide sequence to SEQ ID NO: 13, or the nucleotide sequence of the *L. intracellularis* gene contained in the plasmid pGTE#5 which has been deposited under AGAL Accession No.NM00/16480. It shall also be understood that the term "tlyC polypeptide" refers to a polypeptide of the invention which comprises the amino acid sequence set forth in SEQ ID NO: 14 or a polypeptide encoded by the *L. intracellularis* gene contained in the plasmid pGTE#5 which has been deposited under AGAL Accession No.NM00/16480. The term "tlyC polypeptide" shall further be taken to include a polypeptide which is functionally-related to or immunologically cross-reactive with the polypeptide of SEQ ID NO: 14 or a polypeptide encoded by the *L. intracellularis* gene contained in the plasmid pGTE#5 which has been deposited under AGAL Accession No.NM00/16480.

As used herein, the word "ytfM", or the term "ytfM gene", shall be taken to refer to a gene encoding the antigenic ytfM polypeptide of the present invention, which gene comprises the nucleotide sequence set forth in SEQ ID NO: 15 or the nucleotide sequence of the *L. intracellularis* gene contained in the plasmid pGTE#7 which has been deposited under AGAL Accession No.NM00/16482. The word "ytfM" or the term "ytfM gene" shall further be taken to include a degenerate or complementary nucleotide sequence to SEQ ID NO: 15, or the nucleotide sequence of the *L. intracellularis* gene contained in the plasmid pGTE#7 which has been deposited under AGAL Accession No.NM00/16482. It shall also be understood that the term "ytfM polypeptide" refers to a polypeptide of the invention which comprises the amino acid sequence set forth in SEQ ID NO: 16 or a polypeptide encoded by the *L. intracellularis* gene contained in the plasmid pGTE#7 which has been deposited under AGAL Accession No.NM00/16482. The term "ytfM polypeptide" shall further be taken to include a polypeptide which is functionally-related to or immunologically cross-reactive with the polypeptide of SEQ ID NO: 16 or a polypeptide encoded by the *L. intracellularis* gene contained in the plasmid pGTE#7 which has been deposited under AGAL Accession No. NM00/16482.

As used herein, the word "ytfN", or the term "ytfN gene", shall be taken to refer to a gene encoding the antigenic ytfN polypeptide of the present invention, which gene comprises the nucleotide sequence set forth in SEQ ID NO: 17 or the nucleotide sequence of the *L. intracellularis* gene contained in the plasmid pGTE#8 which has been deposited under AGAL Accession No. NM01/23286. The word "ytfN" or the term "ytfN gene" shall further be taken to include a degenerate or complementary nucleotide sequence to SEQ ID NO: 17 or the nucleotide sequence of the *L. intracellularis* gene contained in the plasmid pGTE#8 which has been deposited under AGAL Accession No. NM01/23286. It shall also be understood that the term "ytfN polypeptide" refers to a polypeptide of the invention which comprises the amino acid sequence set forth in SEQ ID NO: 18 or a polypeptide encoded by the *L. intracellularis* gene contained in the plasmid pGTE#8 which has been deposited under AGAL Accession No. NM01/23286. The term "ytfN polypeptide" shall further be taken to include a polypeptide which is functionally-related to or immunologically cross-reactive with the polypeptide of SEQ ID NO: 18 or a polypeptide encoded by the *L. intracellularis* gene contained in the plasmid pGTE#8 which has been deposited under AGAL Accession No. NM01/23286.

As used herein the words "from" or "of", and the term "derived from" shall be taken to indicate that a specified product, in particular a macromolecule such as a polypeptide, protein, gene or nucleic acid molecule, antibody molecule, Ig fraction, or other macromolecule, or a biological sample comprising said macromolecule, may be obtained from a particular source, organism, tissue, organ or cell, albeit not necessarily directly from that source, organism, tissue, organ or cell.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps, features, compositions and compounds.

The present invention is not to be limited in scope by the specific embodiments described herein, which are intended for the purposes of exemplification only. Functionally equivalent products, compositions and methods are clearly within the scope of the invention, as described herein.

BACKGROUND OF THE INVENTION

The meat-producing sector of the agricultural industry is dependent upon the health of its livestock and there is a need to maintain disease-free livestock for human consumption. The industry is subject to rapid economic downturn in response to disease conditions adversely affecting livestock and the quality of meat products derived therefrom, including those diseases which may potentially be transmitted to humans. It is important, therefore, to have well defined treatments and prophylactic and diagnostic procedures available to deal with infections or potential infections in livestock animals and humans.

Meat products derived from porcine and avian species are significant commercial products in the agriculture industry. In particular, pigs form a major component of the meat industry. However, pigs are sensitive to a wide spectrum of intestinal diseases collectively referred to as porcine proliferative enteropathy (PPE). These diseases have previously been known as intestinal adenomatosis complex (Barker and van Drumel, 1985), porcine intestinal adenomatosis (PIA), necrotic enteritis (Rowland and Lawson, 1976), proliferative haemorrhagic enteropathy (Love and Love, 1977), regional ileitis (Jonsson and Martinsson, 1976), haemorrhagic bowel syndrome (O'Neil, 1970), porcine proliferative enteritis and *Campylobacter* spp—induced enteritis (Straw, 1990).

There are two main forms of PPE: a non-haemorrhagic form represented by intestinal adenomatosis which frequently causes growth retardation and mild diarrhoea; and a haemorrhagic form, which is often fatal, represented by proliferative haemorrhagic enteropathy (PHE), where the distal small intestine lumen becomes engorged with blood. PPE has been reported in a number of animal species including pigs (McOrist et al, 1993), hamsters (Stills, 1991), ferrets (Fox et al, 1989), guinea pigs (Elwell et al, 1981), rabbits (Schodeb and Fox, 1990) as well as avian species (Mason et al, 1998).

PPE is a significant cost component associated with the pig industry, especially in terms of stock losses, medication costs, reduced growth rates of pigs and increased feed costs. PPE also contributes to downstream indirect costs in, for example, additional labour costs and environmental costs in dealing with antibiotic residue contamination, and in control measures to prevent the organism from being passed on or carried to other animals or humans.

*L. intracellularis* is a causative agent of PPE (McOrist et al, 1995). *L. intracellularis* is an intracellular, possibly obligate intracellular, bacterium. It can only be cultured in vitro with tissue culture cells (Jones et al., 1997; Lawson et al., 1993; McOrist et al, 1995; International Patent Application No. PCT/US96/09576). *L. intracellularis* is located in the cytoplasm of the villus cells and intestinal crypt cells of infected animals. Pigs suffering from PPE are characterised by irregularities in the villus cells and intestinal crypt structure with epithelial cell dysplasia, wherein crypt abscesses form as the villi and intestinal crypts become branched and fill with inflammatory cells.

Current control strategies for PPE rely on the use of antibacterials. However, such a strategy is considered to only be short to medium term, especially since governmental regulatory pressures tend to discourage animal husbandry practices which involve the use of prophylactic antibiotics. There is a need, therefore, to develop effective, safe and low cost alternatives to the use of antibiotics and, in particular, to develop vaccine preparations capable of conferring protective immunity against *L. intracellularis* infection in livestock animals.

The most effective vaccine preparations are generally comprised of a highly antigenic component, such as a polypeptide or other macromolecule which is derived from the pathogenic organism against which the vaccine is directed, wherein said antigenic component produces little or no contraindications when administered to a susceptible host animal, and produces little or no antigenic cross-reactivity with desirable organisms, such as non-pathogenic organisms that are a part of the normal flora of the intestinal tract or other tissues of said host animal. In summary, an effective vaccine preparation must be immunogenic, specific and safe.

Accordingly, there is a need to identify highly immunogenic antigens produced by the bacterium *L. intracellularis*.

International Patent Application No. PCT/AU96/00767 describes several *L. intracellularis* partial genetic sequences, and partial polypeptides encoded thereby. However, there is a need to further identify polypeptide immunogens produced by the bacterium *L. intracellularis* and immunogenic peptides derived therefrom, including those immunogens which are genus- or species-specific, for use in improved vaccine compositions. The presently-described invention provides such immunogens.

SUMMARY OF THE INVENTION

One aspect of the present invention is directed to an isolated or recombinant immunogenic polypeptide which comprises, mimics or cross-reacts with a B-cell or T-cell epitope of a polypeptide derived from *Lawsonia* spp, in particular a polypeptide selected from the group consisting of flhB, fliR, ntrC, glnH, motA, motB, tlyC, ytfM, and ytfN polypeptides, or a homologue, analogue or derivative of any one or more of said polypeptides.

Preferably, the isolated or recombinant immunogenic polypeptide is selected from the group consisting of the following:

(i) a polypeptide which comprises an amino acid sequence which has at least about 60% sequence identity overall to an amino acid sequence selected from the group consisting of SEQ ID NOs: 2, 4, 6, 8, 10, 12, 14, 16, and 18;

(ii) a polypeptide which comprises an amino acid sequence which has at least about 60% sequence identity overall to an amino acid sequence encoded by *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motB); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(iii) a polypeptide which comprises at least about 5 contiguous amino acids of an amino acid sequence selected from the group consisting of SEQ ID NOs: 2, 4, 6, 8, 10, 12, 14, 16, and 18;

(iv) a polypeptide which comprises at least about 5 contiguous amino acids of an amino acid sequence encoded by *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motB); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN); and (v) a homologue, analogue or derivative of any one of (i) to (iv) which mimics a B-cell or T-cell epitope of *Lawsonia* spp.

In an alternative preferred embodiment, the isolated or recombinant immunogenic polypeptide is selected from the group consisting of the following:

(i) a polypeptide which comprises an amino acid sequence encoded by a nucleotide sequence having at least about 60% sequence identity overall to a nucleotide sequence selected from the group consisting of SEQ ID NOs: 1, 3, 5, 7, 9, 11, 13, 15, and 17;

(ii) a polypeptide which comprises an amino acid sequence encoded by a nucleotide sequence having at least about 60% sequence identity overall to the nucleotide sequence of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(iii) a polypeptide encoded by at least about 15 contiguous nucleotides of a nucleotide sequence selected from the group consisting of SEQ ID NOs: 1, 3, 5, 7, 9, 11, 13, 15, and 17;

(iv) a polypeptide encoded by at least about 15 contiguous nucleotides of a nucleotide sequence of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN); and (v) a homologue, analogue or derivative of any one of (i) to (iv) which mimics a B-cell or T-cell epitope of *Lawsonia* spp.

In a particularly preferred embodiment, the polypeptide of the present invention comprises or consists of an amino acid sequence selected from the group consisting of:

(i) an amino acid sequence selected from the group consisting of SEQ ID NOs: 2, 4, 6, 8, 10, 12, 14, 16, and 18; and (ii) an amino acid sequence encoded by *L. intracellularis* DNA contained within a deposited plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN).

A further aspect of the present invention provides a vaccine composition for the prophylaxis or treatment of infection in an animal, such as a pig or bird, by *L. intracellularis* or a similar or otherwise related microorganism, said vaccine composition comprising an immunologically effective amount of an immunogenic component which comprises an isolated or recombinant polypeptide selected from the group consisting of flhB, fliR, ntrC, glnH, motA, motB, tlyC, ytfM, and ytfN polypeptides as described herein and one or more carriers, diluents and/or adjuvants suitable for veterinary or pharmaceutical use.

A further aspect of the invention extends to an immunologically interactive molecule, such as an antibody or antibody fragment, which is capable of binding to an immunogenic polypeptide of the invention selected from the group consisting of flhB, fliR, ntrC, glnH, motA, motB, tlyC, ytfM, and ytfN polypeptides.

A further aspect of the invention provides a method of diagnosing infection of an animal by *L. intracellularis* or a related microorganism, said method comprising the steps of contacting a biological sample derived from said animal with an immunologically interactive molecule of the present invention for a time and under conditions sufficient for a complex, such as an antigen:antibody complex, to form, and then detecting said complex formation.

A further aspect of the present invention contemplates a method of determining whether or not an animal has suffered from a past infection, or is currently infected, by *L. intracellularis* or a related microorganism, said method comprising contacting a tissue or fluid sample, such as blood or serum derived from said animal, with an immunogenic polypeptide selected from the group consisting of flhB, fliR, ntrC, glnH, motA, motB, tlyC, ytfM, and ytfN polypeptides, or a peptide derived therefrom, for a time and under conditions sufficient for a complex, such as an antigen:antibody complex, to form, and then detecting said complex formation.

A further aspect of the present invention provides an isolated nucleic acid molecule which comprises a sequence of nucleotides that encodes, or is complementary to a nucleic acid molecule that encodes, a polypeptide selected from the group consisting of flhB, fliR, ntrC, glnH, motA, motB, tlyC, ytfM, and ytfN polypeptides, including any and all genes selected from the group consisting of flhB, fliR, ntrC, glnH, motA, motB, tlyC, ytfM, and ytfN genes as defined hereinabove.

In a preferred embodiment, the isolated nucleic acid molecule comprises a nucleotide sequence encoding a polypeptide that is immunologically cross-reactive with *L. intracellularis* or other causative agent of PPE, wherein said nucleotide sequence is selected from the group consisting of:

(i) a nucleotide sequence having at least about 60% sequence identity overall to a nucleotide sequence selected from the group consisting of SEQ ID NOs: 1, 3, 5, 7, 9, 11, 13, 15, and 17;

(ii) a nucleotide sequence having at least about 60% sequence identity overall to *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(iii) a nucleotide sequence which comprises at least about 15 contiguous nucleotides of a sequence selected from the group consisting of SEQ ID NOs: 1, 3, 5, 7, 9, 11, 13, 15, and 17;

(iv) a nucleotide sequence which comprises at least about 15 contiguous nucleotides of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(v) a nucleotide sequence which hybridizes under at least low stringency, more preferably moderate stringency, and most preferably high stringency conditions to a nucleotide sequence selected from the group consisting of SEQ ID NOs: 1, 3, 5, 7, 9,11, 13, 15, and 17 or a complementary nucleotide sequence thereto;

(vi) a nucleotide sequence which hybridizes under at least low stringency, more preferably moderate stringency, and most preferably high stringency conditions to *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN); and (vii) a homologue, analogue or derivative of any one of (i) to (vi) which encodes a polypeptide which mimics a B-cell or T-cell epitope of *Lawsonia* spp.

In a particularly preferred embodiment, the isolated nucleic acid molecule of the present invention comprises or consists of a nucleotide sequence selected from the group consisting of:

(i) a nucleotide sequence selected from the group consisting of SEQ ID NOs: 1, 3, 5, 7, 9, 11, 13, 15, and 17; or a degenerate variant thereof;

(ii) a nucleotide sequence of the *L. intracellularis* DNA contained within a deposited plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN); and (iii) a nucleotide sequence that encodes the same polypeptide as (i) or (ii), wherein said polypeptide is selected from the group consisting of flhB, fliR, ntrC, glnH, motA, motB, tlyC, ytfM, and ytfN;

(iv) a nucleotide sequence that is complementary to (i) or (ii) or (iii); and (v) a nucleotide sequence that hybridises under high stringency conditions to the complement of a sequence selected from the group consisting of: SEQ ID NOs: 1, 3, 5, 7, 9, 11, 13, 15 and 17, wherein said nucleotide sequence is the complement of a sequence that encodes a polypeptide that is immunologically cross-reactive to a polypeptide selected from the group consisting of flhB, fliR, ntrC, glnH, motA, motB, tlyC, ytfM, and ytfN.

A still further aspect of the invention provides a diagnostic method of detecting *L. intracellularis* or related microorganism in a biological sample derived from an animal subject, said method comprising the steps of hybridising one or more polynucleotide or oligonucleotide probes or primers derived from a gene selected from the group consisting of flhB, fliR, ntrC, glnH, motA, motB, tlyC, ytfM, and ytfN genes, or a homologue, analogue or derivative thereof, to said sample, and then detecting said hybridisation using a detection means. The detection means according to this aspect of the invention is any nucleic acid-based hybridisation or amplification reaction.

A further aspect of the invention provides an isolated probe or primer derived from a gene selected from the group consisting of flhB, fliR, ntrC, glnH, motA, motB, tlyC, ytfM, and ytfN genes. In a particularly preferred embodiment, the probe or primer of the invention is useful for isolating the ytfM and/or ytfN genes described herein. More preferably, the probe or primer of the invention comprises a nucleotide sequence selected from the group consisting of SEQ ID NO: 19 to SEQ ID NO: 68 or a complementary nucleotide sequence thereto.

DETAILED DESCRIPTION OF THE INVENTION

Figure 1:
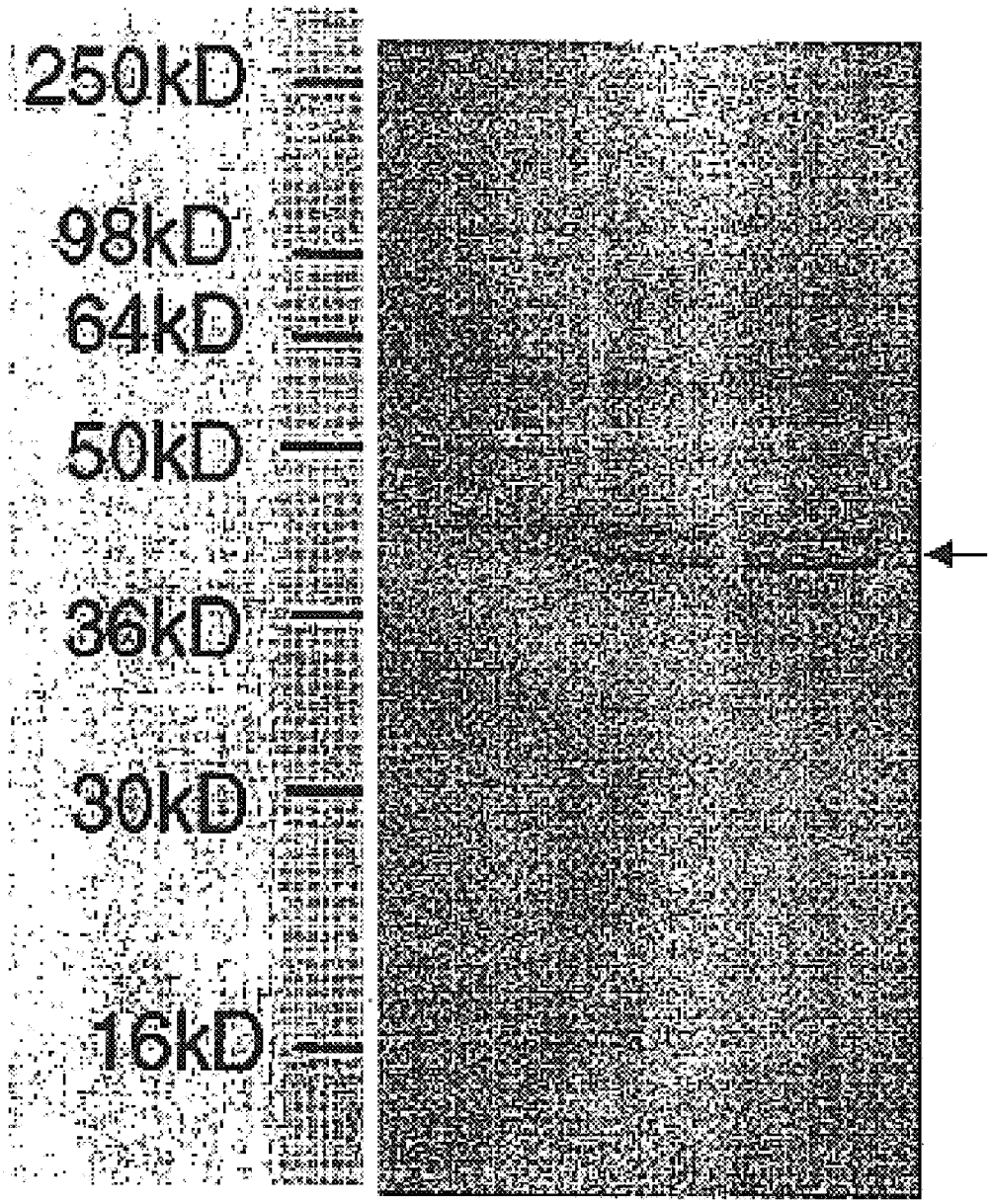
FIG. 1 is a copy of a photographic representation showing expression of recombinant YtfN protein. The 5' portion of the gene up to the BgIII site was cloned into pET-30a. A plasmid with the fragment inserted in the proper orientation was transformed into *E. coli* BL21 (DE3) cells, and a single clone was propagated. Induction was at $OD_{625}$=2.9 with 0.1 mM IPTG. Lane 1, whole cell lysate (WCL) from uninduced cells; lanes 2 and 3, WCL at 2.25 and 3 hrs post-induction, respectively. Arrow indicates the position of recombinant YtfN protein.

In work leading up to the present invention, the inventors sought to identify immunogenic proteins of *L. intracellularis* for use in vaccines for the prophylaxis and treatment of PPE in animals, including pigs and birds.

Accordingly, one aspect of the present invention is directed to an isolated or recombinant immunogenic polypeptide which comprises, mimics or cross-reacts with a B-cell or T-cell epitope of a polypeptide derived from *Lawsonia* spp, selected from the group consisting of flhB, fliR, ntrC, glnH, motA, motB, tlyC, ytfM, and ytfN, or a homologue, analogue or derivative of any one or more of said polypeptides.

Epitopes of *Lawsonia* spp. may be B cell epitopes or T-cell epitopes. It is well-known that antibody-binding sites (B-cell epitopes) involve linear as well as conformational epitopes (van Regenmortel, 1992). B-cell epitopes are predominantly conformational. In contrast, T-cells recognize predominantly linear epitope sequences in combination with MHC class II molecules.

A precise identification and careful selection of epitopes of *Lawsonia* spp. facilitates the development of diagnostic reagents and vaccine compositions for the effective treatment or prophylaxis of *Lawsonia* infections. Epitope identification and characterization (i.e., determination of the molecular weight, amino acid sequence, and structure of epitopes of *Lawsonia* spp.) may be performed using art-recognised techniques. For the detection of conformational epitopes, degrading and denaturing of the epitope molecule must be avoided in order to conserve the three-dimensional structure, because the antigen-antibody reaction will be diminished if the secondary structure of the epitope is altered significantly. In practice, the characterisation and isolation of linear non-conformational epitopes is easier, because any immunoreactive regions are contained within a single polypeptide or peptide fragment which is capable of being purified under a range of conditions.

Both non-conformational and conformational epitopes may be identified by virtue of their ability to bind detectable amounts of antibodies (such as IgM or IgG) from sera of animals immunised against or infected with *Lawsonia* spp. and, in particular *L. intracellularis*, or an isolated polypeptide derived therefrom or, alternatively, by virtue of their ability to bind detectable amounts of antibodies in a purified Ig fraction derived from such sera. The antibodies may be derived from or contained within pools of polyclonal sera, or may be monoclonal antibodies. Antibody fragments or recombinant antibodies, such as those expressed on the surface of a bacteriophage or virus particle, such as in a phage display library, may also be employed.

The determination of T-cell epitopes is performed by analysing the ability of the epitope peptides to induce the proliferation of peripheral blood lymphocytes or T-cell clones. The identification of T-cell epitopes is accomplished using a variety of methods as known in the art, including the use of whole and fragmented native or recombinant antigenic protein, as well as the more commonly employed "overlapping peptide" method. In the latter method, overlapping peptides which span the entire sequence of a polypeptide derived from *Lawsonia* spp. are synthesized and tested for their capacity to stimulate T-cell cytotoxic or proliferative responses in vitro.

Structure determination of both conformational non-linear and non-conformational linear epitopes may be performed by nuclear magnetic resonance spectroscopy (NMR) and X-ray crystallographic analysis. The determination of epitopes using X-ray techniques requires the protein-antibody complex to be crystallized, whereas NMR allows analysis of the complex in a liquid state. NMR measures the amount of amino acids as well as the neighbourhood of protons of different amino acid residues, wherein the alternating effect of two protons along the carbon backbone is characteristic of a particular epitope.

A successful method to recognize non-conformational linear epitopes is the immunoblot and in particular, the Western blot. Peptides may be generated from a complete *Lawsonia* spp. polypeptide by digestion with site-specific proteases, such as trypsin or chymotrypsin, and the peptides generated thereby can be separated using standard electrophoretic or chromatographic procedures. For example, after electrophoresis according to molecular weight using SDS/PAGE (SDS/polyacrylamide gel electrophoresis) and/or according to isoelectric point using IEF (isoelectric focussing) or alternatively, by two-dimensional electrophoresis, the peptides can be transferred to immobilizing nylon or nitrocellulose membranes and incubated with sera raised against the intact polypeptides. Peptides that comprise immunogenic regions (i.e., B-cell or T-cell epitopes) are bound by the antibodies in the sera and the bound antibodies may be detected using secondary antibodies, such as anti-IgG antibodies, that have been labelled radioactively or enzymatically. The epitopes may then be characterised by purification based upon their size, charge or ability to bind specifically to antibodies against the intact polypeptide, using one or more techniques, such as size-exclusion chromatography, ion-exchange chromatography, affinity chromatography or ELISA among others. After purification of the epitope, only one band or spot should be detectable with gel electrophoresis. The N-terminal or total sequencing of the polypeptide or peptide fragment offers the possibility to compare the amino acid sequence with known proteins in databases. Several computer-driven algorithms have now been devised to search for T-cell epitopes in proteins (Margalit et a, 1987; Vajda and C. DeLisi, 1990; Altuvia et al., 1994; Parker et al. 1994; DeGroot et al., 1995; Gabriel et al, 1995; Meister et al., 1995). These algorithms search the amino acid sequence of a given protein for characteristics believed to be common to immunogenic peptides, locating regions that are likely to induce a cellular immune response in vitro. Computer-driven algorithms can identify regions of a *Lawsonia* spp. polypeptide that contain epitopes and are less variable among different isolates. Alternatively, computer-driven algorithms can rapidly identify regions of each isolate's more variable proteins that should be included in a multivalent vaccine.

The AMPHI algorithm (Margalit et al., 1987), which is based on the periodicity of T cell epitopes, has been widely used for the prediction of T-cell antigenic sites from sequence information alone. Essentially, AMPHI describes a common structural pattern of MHC binding motifs, since MHC binding motifs (i.e., patterns of amino acids that appear to be common to most of the peptides that bind to a specific MHC molecule) appear to exhibit the same periodicity as an alpha helix. Identification of T-cell epitopes by locating MHC binding motifs in an amino acid sequence provides an effective means of identifying immunogenic epitopes in diagnostic assays.

The EpiMer algorithm (Meister et al., 1995; Gabriel et al., 1995; DeGroot et al., 1995) locates clustered MHC binding motifs in amino acid sequences of proteins, based upon the correlation between MHC binding motif-dense regions and peptides that may have the capacity to bind to a variety of MHC molecules (promiscuous or multi-determinant binders) and to stimulate an immune response in these various MHC contexts as well (promiscuous or multi-determinant epitopes). The EpiMer algorithm uses a library of MHC binding motifs for multiple class I and class II HLA alleles to predict antigenic sites within a protein that have the potential to induce an immune response in subjects with a variety of genetic backgrounds. EpiMer locates matches to each MHC-binding motif within the primary sequence of a given protein antigen. The relative density of these motif matches is determined along the length of the antigen, resulting in the generation of a motif-density histogram. Finally, the algorithm identifies protein regions in this histogram with a motif match density above an algorithm-defined cutoff density value, and produces a list of subsequences representing these clustered, or motif-rich regions. The regions selected by EpiMer may be more likely to act as multi-determinant binding peptides than randomly chosen peptides from the same antigen, due to their concentration of MHC-binding motif matches. The selection of regions that are MHC binding motif-dense increases the likelihood that the predicted polypeptide or peptide fragment contains a "valid" motif, and furthermore, that the reiteration of identical motifs may contribute to binding.

Additional MHC binding motif-based algorithms have been described by Parker et al. (1994) and Altuvia et al. (1994). In these algorithms, binding to a given MHC molecule is predicted by a linear function of the residues at each position, based on empirically defined parameters, and in the case of the Altuvia et al. (1994) algorithm, known crystallographic structures may also be taken into consideration.

Recombinant methods offer the opportunity to obtain well characterized epitopes of high purity for the production of diagnostic reagents and epitope-specific vaccine formulations (Mohapatra et al., 1995). Based upon the amino acid sequence of a linear epitope and identification of the corresponding nucleotide sequence encoding same, polymerase chain reaction (PCR) may be performed to amplify the epitope-encoding region from cDNA. After cloning and expression in a suitable vector/host system, a large amount of epitopes of high purity can be extracted. Accordingly, the present invention clearly extends to both isolated non-recombinant polypeptides and recombinant polypeptides in an impure or isolated form.

The term "polypeptide" as used herein shall be taken to refer to any polymer consisting of amino acids linked by covalent bonds and includes within its scope the full-length amino acids disclosed herein, and any parts or fragments thereof such as, for example, peptides consisting of about 5–50 amino acid residues in length, preferably about 5–30 amino acid residues in length, more preferably about 5–20 amino acid residues in length, and even more preferably about 5–10 amino acid residues in length. Also included within the scope of the definition of a "polypeptide" are amino acid sequence variants, containing one or more preferably conservative amino acid substitutions, deletions, or insertions, which do not alter at least one essential property of said polypeptide such as, for example, its immunogenicity, use as a diagnostic reagent, or effectiveness as a vaccine against *Lawsonia* spp, amongst others. Accordingly, a polypeptide may be isolated from a source in nature, or chemically synthesized. Furthermore, a polypeptide may be derived from a full-length protein by chemical or enzymatic cleavage, using reagents such as CNBr, trypsin, or chymotrypsin, amongst others.

Conservative amino acid substitutions are well-known in the art. For example, one or more amino acid residues of a native flagellar hook protein of the present invention can be substituted conservatively with an amino acid residue of similar charge, size or polarity, with the resulting polypeptide retaining an ability to function in a vaccine or as a diagnostic reagent as described herein. Rules for making such substitutions include those described by Dayhof (1978). More specifically, conservative amino acid substitutions are those that generally take place within a family of amino acids that are related in their side chains. Genetically-encoded amino acids are generally divided into four groups: (1) acidic=aspartate, glutamate; (2) basic=lysine, arginine, and histidine; (3) non-polar=alanine, valine, leucine, isoleucine, proline, phenylalanine, methionine, and tryptophan; and (4) uncharged polar=glycine, asparagine, glutamine, cysteine, serine, threonine, and tyrosine. Phenylalanine, tyrosine and tryptophan are also jointly classified as aromatic amino acids. One or more replacements within any particular group such as, for example, the substitution of leucine for isoleucine or valine or alternatively, the substitution of aspartate for glutamate or threonine for serine, or of any other amino acid residue with a structurally-related amino acid residue, will generally have an insignificant effect on the function of the resulting polypeptide.

The present invention is not limited by the source of the subject immunogen and clearly extends to isolated and recombinant polypeptides which are derived from a natural or a non-natural occurring source.

The term "recombinant polypeptide" as used herein shall be taken to refer to a polypeptide which is produced in vitro or in a host cell by the expression of a genetic sequence encoding said polypeptide, which genetic sequence is under the control of a suitable promoter, wherein a genetic manipulation has been performed in order to achieve said expression. Accordingly, the term "recombinant polypeptide" clearly encompasses polypeptides produced by the expression of genetic sequences contained in viral vectors, cosmids or plasmids that have been introduced into prokaryotic or eukaryotic cells, tissues or organs. Genetic manipulations which may be used in this context will be known to those skilled in the art and include, but are not limited to, nucleic acid isolation, restriction endonuclease digestion, exonuclease digestion, end-filling using the Klenow fragment of *E. coli* DNA polymerase I or T4 DNA polymerase enzymes, blunt-ending of DNA molecules using T4 DNA polymerase or ExoIII enzymes, site-directed mutagenesis, ligation, and amplification reactions. As will be known to those skilled in the art, additional techniques such as nucleic acid hybridisations and nucleotide sequence analysis may also be utilised in the preparation of recombinant polypeptides, in confirming the identity of a nucleic acid molecule encoding a desired recombinant polypeptide and a genetic construct comprising the nucleic acid molecule.

Wherein the polypeptide of the present invention is a recombinant polypeptide, it may be produced in and, if desirable, isolated from a recombinant viral vector expression system or host cell. As will be known to those skilled in the relevant art, a cell for production of a recombinant polypeptide is selected on the basis of several parameters including the genetic constructs used to express the polypeptide under consideration, as well as the stability and activity of said polypeptide. It will also be known to those skilled in the art that the stability or activity of a recombinant polypeptide may be determined, at least in part, by post-translational modifications to the polypeptide such as, for example, glycosylation, acylation or alkylation reactions, amongst others, which may vary between cell lines used to produce the recombinant polypeptide.

Accordingly, in a more particularly preferred embodiment, the present invention extends to a recombinant polypeptide or a derivative, homologue or analogue thereof as present in a virus particle, or as produced in prokaryotic or eukaryotic host cell, or in a virus or cell culture thereof.

The present invention also extends to a recombinant polypeptide according to any of the foregoing embodiments which is produced in a bacterial cell belonging to the genus *Lawsonia*, in particular a cell of *L. intracellularis*, or a culture thereof.

The term "isolated polypeptide" refers to a polypeptide of the present invention which has been purified to some extent, preferably to at least about 20% by weight of protein, preferably to at least about 50% by weight of protein, more preferably to at least about 60% by weight of protein, still more preferably to at least about 70% by weight of protein and even more preferably to at least about 80% by weight of protein or greater, from its natural source or, in the case of non-naturally-occurring polypeptides, from the culture medium or cellular environment in which it was produced. Such isolation may be performed to improve the immunogenicity of the polypeptide of the present invention, or to improve the specificity of the immune response against that polypeptide, or to remove toxic or undesirable contaminants therefrom. The necessary or required degree of purity of an isolated polypeptide will vary depending upon the purpose for which the polypeptide is intended, and for many applications it will be sufficient for the polypeptide preparation to contain no contaminants which would reduce the immunogenicity of the polypeptide when administered to a host animal, in particular a porcine or avian animal being immunized against PPE or, alternatively, which would inhibit immuno-specific binding in an immunoassay for the diagnosis of PPE or a causative agent thereof.

The purity of an isolated polypeptide of the present invention may be determined by any means known to those skilled in the art, including the degree of homogeneity of a protein preparation as assessed by SDS/polyacrylamide gel electrophoresis, 2-dimensional electrophoresis, or amino acid composition analysis or sequence analysis.

Preferably, the polypeptide of the present invention will be substantially homogeneous or substantially free of nonspecific proteins, as assessed by SDS/polyacrylamide gel electrophoresis, 2-dimensional electrophoresis, or amino acid composition analysis or sequence analysis.

The polypeptide of the present invention can be purified for use as a component of a vaccine composition by any one or a combination of methods known to those of ordinary skill in the art, including, for example, reverse phase chromatography, HPLC, ion-exchange chromatography, and affinity chromatography, among others.

In a preferred embodiment, the isolated or recombinant polypeptide of the invention functions is secretable into the periplasmic space of a cell, preferably into the periplasm of a prokaryotic cell, such as, for example, *Escherichia coli*. or *L. intracellularis*, or, alternatively, is immunologically cross-reactive with a *L. intracellularis* polypeptide selected from the group consisting of flhB, fliR, ntrC, glnH, motA, motB, tlyC, ytfM, and ytfN.

In a particularly preferred embodiment, the isolated or recombinant polypeptide of the invention is derived from *Lawsonia* spp. or other pathogenic agent associated with the onset and/or development of PPE and more preferably, the subject polypeptide is derived from *L. intracellularis*.

A B-cell or T-cell epitope of a polypeptide selected from the group consisting of flhB, fliR, ntrC, glnH, motA, motB, tlyC, ytfM, and ytfN polypeptides, or a homologue, analogue or derivative of any one or more of said polypeptides, may comprise one or more of the following:

(i) the primary amino acid sequence of any one of said polypeptides, as determined by an art-accepted methodology to comprise a continuous non-conformational epitope;

(ii) the secondary structure which any one of said polypeptides adopt, as determined by an art-accepted methodology to comprise a continuous conformational epitope;

(iii) the tertiary structure which any one of said polypeptides adopt in contact with another region of the same polypeptide molecule, as determined by an art-accepted methodology to comprise a discontinuous conformational epitope; or (iv) the quaternary structure which any one of said polypeptides adopt in contact with a region of another polypeptide molecule, as determined by an art-accepted methodology to comprise a discontinuous conformational epitope.

Accordingly, immunogenic polypeptides or derivatives, homologues or analogues thereof comprising the same, or substantially the same primary amino acid sequence are hereinafter defined as "immunogens which comprise a B-cell or T-cell epitope" or similar term.

Immunogenic polypeptides or derivatives, homologues, or analogues thereof comprising different primary amino acid sequences may comprise immunologically identical immunogens, because they possess conformational B-cell or T-cell epitopes that are recognised by the immune system of a host species to be identical. Such immunogenic polypeptides or derivatives, homologues or analogues thereof are hereinafter defined as "immunogens which mimic or cross-react with a B-cell or T-cell epitope", or similar term.

Accordingly, the present invention extends to an immunogen which comprises, mimics, or cross-reacts with a B-cell or T-cell epitope of an isolated or recombinant polypeptide according to any one of the foregoing embodiments or a derivative, homologue or analogue thereof. In a particularly preferred embodiment, the present invention provides an immunogen which comprises, mimics, or cross-reacts with a B-cell or T-cell epitope of an isolated or recombinant polypeptide which in its native form is obtainable from a species of *Lawsonia* such as, but not limited to *L. intracellularis* and which polypeptide preferably has the same biological function as a polypeptide selected from the group consisting of flhB, fliR, ntrC, glnH, motA, motB, tlyC, ytfM, and ytfN, as hereinbefore defined.

Preferably, such immunogenic polypeptides will not comprise a primary amino acid sequence which is highly-conserved between *L. intracellularis* and another non-pathogenic microorganism which is normally resident in the gut or other organ of an animal, in particular a porcine or avian animal. The significance of this exclusion to those embodiments of the invention wherein specificity is essential to performance (eg vaccine and diagnostic applications) will be apparent to those skilled in the art.

To improve the immunogenicity of a subject polypeptide of the present invention one or more amino acids not corresponding to the original protein sequence can be added to the amino or carboxyl terminus of the polypeptide. Such extra amino acids are useful for coupling the polypeptide to another peptide or polypeptide, to a large carrier protein or to a solid support. Amino acids that are useful for these purposes include but are not limited to tyrosine, lysine, glutamic acid, aspartic acid, cysteine and derivatives thereof. Additional protein modification techniques can be used such as, e.g., $NH_2$-acetylation or COOH-terminal amidation, to provide additional means for coupling the polypeptide to another polypeptide or peptide molecule, or to a solid support. Procedures for coupling polypeptides to each other, or to carrier proteins or solid supports, are well known in the art. Polypeptides containing the above-mentioned extra amino acid residues at either the carboxyl- or amino-termini and either uncoupled or coupled to a carrier or solid support, are consequently within the scope of the present invention.

Furthermore, the polypeptide can be immobilised to a polymeric carrier or support material.

In an alternative embodiment, the immunogenicity of a polypeptide of the present invention may be improved using molecular biology techniques to produce a fusion protein containing one or more polypeptides of the present invention fused to a carrier molecules such as a highly immunogenic protein. For example, a fusion protein containing a polypeptide of the present invention fused to the highly immunogenic B subunit of cholera toxin can be used to increase the immune response to the polypeptide. The present invention also contemplates fusion proteins comprising a cytokine, such as an interleukin, fused to the subject polypeptide of the present invention, and genes encoding same.

Preferably, the polypeptide of the present invention, or a derivative, homologue or analogue thereof, when administered to a mammal, induces an immune response in said mammal. More preferably, the polypeptide of the present invention, when administered to a mammal, in particular a porcine animal (e.g., a pig) induces a protective immune response against *Lawsonia* spp., and preferably against *L. intracellularis*, therein. As used herein, the phrase "induction of a protective immune response", and the like, refers to the ability of the administered polypeptide of the present invention to prevent or detectably slow the onset, development, or progression of symptoms associated with *Lawsonia* infection, and preferably, to prevent or detectably slow the onset, development, or progression of symptoms associated with PPE in pigs.

Preferably, the isolated or recombinant immunogenic polypeptide is selected from the group consisting of the following:

(i) a polypeptide which comprises an amino acid sequence which has at least about 60% sequence identity overall to an amino acid sequence selected from the group consisting of SEQ ID NOs: 2, 4, 6, 8, 10, 12, 14, 16, and 18;

(ii) a polypeptide which comprises an amino acid sequence which has at least about 60% sequence identity overall to an amino acid sequence encoded by *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(iii) a polypeptide which comprises at least about 5 contiguous amino acids, of an amino acid sequence selected from the group consisting of SEQ ID NOs: 2, 4, 6, 8, 10, 12, 14, 16, and 18;

(iv) a polypeptide which comprises at least about 5 contiguous amino acids of an amino acid sequence encoded by *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(v) a homologue, analogue or derivative of any one of (i) to (iv) which mimics a B-cell or T-cell epitope of *Lawsonia* spp.

In an alternative preferred embodiment, the isolated or recombinant immunogenic polypeptide is selected from the group consisting of the following:

(i) a polypeptide which comprises an amino acid sequence encoded by a nucleotide sequence having at least about 60% sequence identity overall to a nucleotide sequence selected from the group consisting of SEQ ID NOs: 1, 3, 5, 7, 9, 11, 13, 15, and 17;

(ii) a polypeptide which comprises an amino acid sequence encoded by a nucleotide sequence having at least about 60% sequence identity overall to the nucleotide sequence of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(iii) a polypeptide encoded by at least about 15 contiguous nucleotides of a nucleotide sequence selected from the group consisting of SEQ ID NOs: 1, 3, 5, 7, 9, 11, 13, 15, and 17;

(iv) a polypeptide encoded by at least about 15 contiguous nucleotides of a nucleotide sequence of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(v) a homologue, analogue or derivative of any one of (i) to (iv) which mimics a B-cell or T-cell epitope of *Lawsonia* spp.

Preferably, the immunogenic polypeptide encompassed by the present invention has at least about 70% identity, more preferably at least about 80% identity, even more preferably at least about 90% identity, and still even more preferably at least about 95% identity to the amino acid sequence of a polypeptide selected from the group consisting of flhB, fliR, ntrC, glnH, motA, motB, tlyC, ytfM, and ytfN polypeptides, as hereinbefore defined.

In determining whether or not two amino acid sequences fall within these percentage limits, those skilled in the art will be aware that it is necessary to conduct a side-by-side comparison or multiple alignment of sequences. In such comparisons or alignments, differences will arise in the positioning of non-identical residues, depending upon the algorithm used to perform the alignment. In the present context, reference to a percentage sequence identity or similarity between two or more amino acid sequences shall be taken to refer to the number of identical and similar residues respectively, between said sequences as determined using any standard algorithm known to those skilled in the art. For example, amino acid sequence identities or similarities may be calculated using the GAP programme of the Computer Genetics Group, Inc., University Research Park, Madison, Wis., United States of America (Devereaux et al, 1984). The GAP programme utilizes the algorithm of Needleman and Wunsch (1970) to maximise the number of identical/similar residues and to minimise the number and/or length of sequence gaps in the alignment. Alternatively or in addition, where more than two amino acid sequences are being compared, the ClustalW programme of Thompson et al (1994) can be used.

Preferably, the isolated or recombinant immunogenic polypeptide of the invention comprises at least about 10 contiguous amino acids of a polypeptide selected from the group consisting of flhB, fliR, ntrC, glnH, motA, motB, tlyC, ytfM, and ytfN polypeptides, as hereinbefore defined. More preferably, the isolated or recombinant immunogenic polypeptide of the invention comprises at least about 20 contiguous amino acid residues of a polypeptide selected from the group consisting of flhB, fliR, ntrC, glnH, motA, motB, tlyC, ytfM, and ytfN polypeptides, as hereinbefore defined. Even more preferably, the isolated or recombinant immunogenic polypeptide of the invention comprises at least about 30 contiguous amino acid residues of a polypeptide selected from the group consisting of flhB, fliR, ntrC, glnH, motA, motB, tlyC, ytfM, and ytfN polypeptides, as hereinbefore defined, and still even more preferably, at least about 40 contiguous amino acid residues of said flhB, fliR, ntrC, glnH, motA, motB, tlyC, ytfM, or ytfN polypeptides.

The present invention further encompasses homologues, analogues and derivatives of a polypeptide selected from the group consisting of flhB, fliR, ntrC, glnH, motA, motB, tlyC, ytfM, and ytfN polypeptides, as hereinbefore defined.

"Homologues" of a polypeptide are those immunogenic polypeptides that are derived from a full-length L. intracellularis polypeptides described herein, or have sequence similarity to a full-length L. intracellularis polypeptide, notwithstanding one or more amino acid substitutions, deletions and/or additions relative to the full-length L. intracellularis polypeptide. A homologue may also retain the biological activity or catalytic activity of the full-length polypeptide. In such homologues, one or more amino acids can be replaced by other amino acids having similar properties such as, for example, hydrophobicity, hydrophilicity, hydrophobic moment, antigenicity, propensity to form or break α-helical structures of β-sheet structures, and so on.

Substitutional variants are those in which at least one residue in the sequence has been removed and a different residue inserted in its place. Amino acid substitutions are typically of single residues, but may be clustered depending upon functional constraints placed upon the polypeptide; insertions will usually be of the order of about 1–10 amino acid residues. and deletions will range from about 1–20 residues. Preferably, amino acid substitutions will comprise conservative amino acid substitutions, such as those described supra.

Insertional amino acid sequence variants are those in which one or more amino acid residues are introduced into a predetermined site in the protein. Insertions can comprise amino-terminal and/or carboxyl terminal fusions as well as intra-sequence insertions of single or multiple amino acids. Generally, insertions within the amino acid sequence will be smaller than amino or carboxyl terminal fusions, of the order of about 1 to 4 residues.

Deletional variants are characterised by the removal of one or more amino acids from the sequence.

Amino acid variants of the polypeptide of the present invention may readily be made using polypeptide synthetic techniques well known in the art, such as solid phase synthesis and the like, or by recombinant DNA manipulations. The manipulation of DNA sequences to produce variant proteins which manifest as substitutional, insertional or deletional variants are well known in the art. For example, techniques for making substitution mutations at predetermined sites in DNA having known sequence are well known to those skilled in the art, such as by M13 mutagenesis or other site-directed mutagenesis protocol.

"Analogues" are defined as those immunogenic polypeptides that are derived from a full-length L. intracellularis polypeptides described herein, or have sequence similarity to a full-length L. intracellularis polypeptide, notwithstanding one or more non-naturally occurring or modified amino acid residues relative to the naturally-occurring full-length L. intracellularis polypeptide. The term "analogue" shall also be taken to include an amino acid sequence which is not similar to an amino acid sequence of a full-length L. intracellularis polypeptide set forth herein, however mimics or cross-reacts with a B-cell or T-cell epitope of Lawsonia spp. and preferably, mimics or cross-reacts with a B-cell or T-cell epitope of L. intracellularis, such as, for example, a polypeptide which is derived from a computational prediction or empirical data revealing the secondary, tertiary or quaternary structure of the full-length polypeptide or an epitope thereof.

For example, mimotopes (polypeptide analogues that cross-react with a B-cell or T-cell epitope of the Lawsonia polypeptide of the invention but, however, comprise a different amino acid sequence to said epitope) may be identified by screening random amino acid sequences in polypeptide libraries with antibodies that bind to a desired T-cell or B-cell epitope. As with techniques for the identification of B-cell or T-cell epitopes as described supra, the antibodies used to identify such mimotopes may be polyclonal or monoclonal or recombinant antibodies, in crude or purified form. Mimotopes of a T-cell epitope may then be assayed further for their ability to stimulate T-cell cytotoxic or proliferative responses in vitro. Mimotopes are particularly useful as analogues of non-linear (i.e., conformational) epitopes of the polypeptide of the present invention, because conformational epitopes are generally formed from non-contiguous regions in a polypeptide, and the mimotopes provide immunogenic equivalents thereof in the form of a single polypeptide molecule.

Additionally, the use of polypeptide analogues can result in polypeptides with increased immunogenic and/or antigenic activity, that are less sensitive to enzymatic degradation, and which are more selective. A suitable proline analogue is 2-aminocyclopentane carboxylic acid ($\beta AC^5c$) which has been shown to increase the immunogenic activity of a native polypeptide more than 20 times (Mierke et al, 1990; Portoghese et al, 1990; Goodman et al, 1987).

"Derivatives" of a polypeptide selected from the group consisting of flhB, fliR, ntrC, glnH, motA, motB, tlyC, ytfM, and ytfN polypeptides, as hereinbefore defined, are those peptides or polypeptides which comprise at least about five contiguous amino acid residues of any one or more of said flhB, fliR, ntrC, glnH, motA, motB, tlyC, ytfM, or ytfN polypeptides.

A "derivative" may further comprise additional naturally-occurring, altered glycosylated, acylated or non-naturally occurring amino acid residues compared to the amino acid sequence of a flhB, or fliR, or ntrC, or glnH, or motA, or motB, or tlyC, or ytfM, or ytfN polypeptide, as hereinbefore defined. Alternatively or in addition, a derivative may comprise one or more non-amino acid substituents such as, for example, a reporter molecule or other ligand, covalently or non-covalently bound to the amino acid sequence of a flhB, or fliR, or ntrC, or glnH, or motA, or motB, or tlyC, or ytfM, or ytfN polypeptide, such as, for example, a reporter molecule which is bound thereto to facilitate its detection.

Other examples of recombinant or synthetic mutants and derivatives of a polypeptide immunogen of the present invention include those incorporating single or multiple substitutions in the amino acid sequence of a polypeptide selected from the group consisting of flhB, fliR, ntrC, glnH, motA, motB, tlyC, ytfM, and ytfN polypeptides. Recombinant or synthetic mutants and derivatives produced by making deletions from the amino acid sequence of a polypeptide selected from the group consisting of flhB, fliR, ntrC, glnH, motA, motB, tlyC, ytfM, and ytfN polypeptides, are also included within the scope of preferred derivatives. Additionally, recombinant or synthetic mutants and derivatives produced by making additions to a polypeptide selected from the group consisting of flhB, fliR, ntrC, glnH, motA, motB, tlyC, ytfM, and ytfN polypeptides, such as, for example, using carbohydrates, lipids and/or proteins or polypeptides, are also encompassed by the present invention.

Naturally-occurring or altered glycosylated or acylated forms of the flhB, fliR, ntrC, glnH, motA, motB, tlyC, ytfM, or ytfN polypeptides are particularly contemplated by the present invention.

Additionally, homopolymers or heteropolymers comprising one or more copies of the reference polypeptides, or one or more derivatives, homologues or analogues thereof, are clearly within the scope of the present invention.

Preferably, homologues, analogues and derivatives of the flhB, fliR, ntrC, glnH, motA, motB, tlyC, ytfM, or ytfN polypeptides of the invention are "immunogenic", defined hereinafter as the ability of said polypeptide, or a derivative, homologue or analogue thereof, to elicit B cell and/or T cell responses in the host, in response to immunization.

Preferred homologues, analogues and derivatives of the flhB, fliR, ntrC, glnH, motA, motB, tlyC, ytfM, or ytfN polypeptides of the invention include any amino acid variant that functions as B cell or T cell epitope of any one of said polypeptides, wherein said variant is capable of mediating an immune response, such as, for example, a mimotope of the immunogenic polypeptide which has been produced by synthetic means, such as by Fmoc chemistry. The only requirement of such variant molecules is that they cross-react immunologically with a polypeptide selected from the group consisting of flhB, fliR, ntrC, glnH, motA, motB, tlyC, ytfM, and ytfN, as hereinbefore defined, or an epitope of said polypeptide.

As will be apparent to those skilled in the art, such homologues, analogues and derivatives of the polypeptides of the invention molecules will be useful to prepare antibodies that cross-react with antibodies against said polypeptide and/or to elicit a protective immune response of similar specificity to that elicited by said polypeptide. Such molecules will also be useful in diagnostic and other applications that are immunological in nature such as, for example, diagnostics which utilise one or more immunoassay formats (eg. ELISA, RIA and the like).

Accordingly, the immunogen of the present invention or a derivative, homologue or analogue thereof is useful in vaccine compositions that protect an individual against infection by *L. intracellularis* and/or as an antigen to elicit polyclonal or monoclonal antibody production and/or in the detection of antibodies against *L. intracellularis* in infected animals, particularly in porcine and avian animals.

The polypeptides of the present invention may comprise leader sequences to facilitate their secretion into the periplasmic space, either as part of the native protein, or alternatively, added by recombinant engineering means. Such may have improved immunogenicity compared to non-secreted or non-secretable polypeptides of *L. intracellularis*, or non-secreted or non-secretable polypeptides of other causative agents of PPE. The particular advantages of such peptides will be immediately apparent to those skilled in the production of vaccine compositions, where the inherent immunogenicity of the immunogen is an important consideration for a protective immune response to be conferred.

Moreover, unique regions of the *L. intracellularis* polypeptides exemplified herein are promising antigenic peptides for the formulation of *Lawsonia*-specific vaccines and diagnostics for the specific detection of *Lawsonia* spp. in biological samples.

A second aspect of the present invention provides a vaccine composition for the prophylaxis or treatment of infection in a mammal or bird by *L. intracellularis* or similar or otherwise related microorganism, said vaccine composition comprising:

(i) an immunogenic component which comprises an isolated or recombinant polypeptide selected from the group consisting of flhB, fliR, ntrC, glnH, motA, motB, tlyC, ytfM, and ytfN polypeptides or an immunogenic homologue, analogue or derivative of any one of said polypeptides which is immunologically cross-reactive with *L. intracellularis*; and (ii) one or more carriers, diluents and/or adjuvants suitable for veterinary or pharmaceutical use.

As used herein, the term "immunogenic component" refers to a polypeptide encoded by DNA from, or derived from, *L. intracellularis* or a related microorganism thereto which is capable of inducing a protective immune response in an animal, in particular a porcine or avian animal, whether or not said polypeptide is in an isolated or recombinant form. Accordingly, the vaccine composition clearly encompasses those vaccine compositions which comprise attenuated, killed or non-pathogenic isolates or forms of *L. intracellularis* or related microorganisms thereto which comprise or express said polypeptide.

By "protective immune response" is meant that the immunogenic component elicits an immune response in the animal to which the vaccine composition is administered at the humoral and/or cellular level which is sufficient to prevent infection by *L. intracellularis* or a related microorganism thereto and/or which is sufficient to detectably reduce one or more symptoms or conditions, or to detectably slow the onset of one or more symptoms or conditions, associated with infection by *L. intracellularis* or a related microorganism thereto in an animal host, as compared to a control infected animal. The term "effective amount" of an immunogenic component present in the vaccine composition refers to that amount of said immunogenic component that is capable of inducing a protective immune response after a single complete dose has been administered, or after several divided doses have been administered.

Preferably, the polypeptide component of the subject vaccine composition comprises an amino acid sequence which is both immunogenic and specific, by virtue of its immunological cross-reactivity with the causative agent of PPE, *L. intracellularis*. In this regard, it will be apparent from the preceding description that such polypeptide components may comprise the amino acid sequence of a polypeptide of *L. intracellularis* as exemplified herein, or alternatively, an immunologically cross-reactive homologue, analogue or derivative of said amino acid sequence, such as, for example, a mimotope of said sequence.

The immunogenic polypeptide or immunogenic homologue, analogue or derivative may be a naturally-occurring polypeptide in isolated or recombinant form according to any of the embodiments described supra or exemplified herein. Preferably, the immunogenic polypeptide or immunogenic homologue, analogue or derivative is derived from *Lawsonia* spp., in particular *L. intracellularis* or a microorganism that is related thereto.

Preferably, the immunogenic component has undergone at least one purification step or at least partial concentration from a cell culture comprising *L. intracellularis* or a related microorganism thereto, or from a lysed preparation of *L. intracellularis* cells or related microorganism, or from another culture in which the immunogenic component is recombinantly expressed. The purity of such a component which has the requisite immunogenic properties is preferably at least about 20% by weight of protein in a particular preparation, more preferably at least about 50%, even more preferably at least about 60%, still more preferably at least about 70% and even more preferably at least about 80% or greater.

The immunogenic component of the vaccine of the present invention can comprise a single polypeptide, or a range or combination of different polypeptides covering different or similar epitopes. In addition or, alternatively, a single polypeptide can be provided with multiple epitopes. The latter type of vaccine is referred to as a polyvalent vaccine. A multiple epitope includes two or more epitopes located within a polypeptide molecule.

The formulation of vaccines is generally known in the art and reference can conveniently be made to Remington's Pharmaceutical Sciences, 17th ed., Mack Publishing Co., Easton, Pa., USA.

A particularly useful form of the vaccine is a recombinant vaccine produced, for example, in a vaccine vector, such as but not limited to a mammalian cell transfected with a vaccinia virus vector, an insect cell transfected with a baculovirus vector, or a bacterial cell transfected with a plasmid or cosmid, the only requirement being that the vector expresses the immunogenic component.

The present invention clearly extends to recombinant vaccine compositions in which the immunogenic component at least is contained within killed vaccine vectors prepared, for example, by heat, formalin or other chemical treatment, electric shock or high or low pressure forces. According to this embodiment, the immunogenic component of the vaccine is generally synthesized in a live vaccine vector which is killed prior to administration to an animal.

Furthermore, the vaccine vector expressing the immunogenic component may be non-pathogenic or attenuated. Within the scope of this embodiment are cells that have been transfected with non-pathogenic or attenuated viruses encoding the immunogenic component of the vaccine and non-pathogenic or attenuated cells that directly express the immunogenic component.

Attenuated or non-pathogenic host cells include those cells which are not harmful to an animal to which the subject vaccine is administered. As will be known to those skilled in the art, "live vaccines" can comprise an attenuated virus vector encoding the immunogenic component or a host cell comprising same, which is capable of replicating in an animal to which it is administered, and using host cell machinery to express the immunogenic component albeit producing no adverse side-effects therein. Such vaccine vectors may colonise the gut or other organ of the vaccinated animal. Such live vaccine vectors are efficacious by virtue of their ability to continually express the immunogenic component in the host animal for a time and at a level sufficient to confer protective immunity against a pathogen which expresses an immunogenic equivalent of said immunogenic component. The present invention clearly encompasses the use of such attenuated or non-pathogenic vectors and live vaccine preparations.

The vaccine vector may be a virus, bacterial cell or a eukaryotic cell such as an insect, avian, porcine or other mammalian cell or a yeast cell or a cell line such as COS, VERO, HeLa, mouse C127, Chinese hamster ovary (CHO), WI-38, baby hamster kidney (BHK) or MDCK cell lines. Suitable prokaryotic cells include *Mycobacterium* spp., *Corynebacterium* spp., *Salmonella* spp., *Escherichia coli*, *Bacillus* spp. and *Pseudomonas* spp, amongst others. Bacterial strains which are suitable for the present purpose are well-known in the relevant art (Ausubel et al, 1987; Sambrook et al, 1989).

Such cells and cell lines are capable of expression of a genetic sequence encoding a polypeptide of the present invention from *L. intracellularis*, or a homologue, analogue or derivative thereof, in a manner effective to induce a protective immune response in the animal. For example, a non-pathogenic bacterium can be prepared containing an expression vector which comprises a nucleotide sequence encoding a polypeptide selected from the group consisting of flhB, fliR, ntrC, glnH, motA, motB, tlyC, ytfM, and ytfN polypeptides, or a homologue, analogue, or derivative thereof, wherein said nucleotide sequence is placed operably under the control of a constitutive or inducible promoter sequence. The bacterium is then permitted to colonise suitable locations in a pig's gut, where it replicates and expresses the said polypeptide in amount sufficient to induce a protective immune response against *L. intracellularis*.

In a further alternative embodiment, the vaccine can be a DNA or RNA vaccine comprising a DNA or RNA molecule encoding a polypeptide selected from the group consisting of flhB, fliR, ntrC, glnH, motA, motB, tlyC, ytfM, and ytfN polypeptides or homologues, analogues or derivatives thereof, wherein said vaccine is injected into muscular tissue or other suitable tissue in a pig under conditions sufficient to permit transient expression of said DNA or RNA to produce an effective amount of said polypeptide to induce a protective immune response. In a preferred embodiment, the DNA vaccine is in the form of a plasmid, in which the DNA is operably connected with a promoter region capable of expressing the nucleotide sequence encoding the immunogen in cells of the immunized animal.

In the production of a recombinant vaccine, except for a DNA vaccine described herein, it is therefore necessary to express the immunogenic component in a suitable vector system. For the present purpose, the immunogenic component can be expressed by:

(i) placing an isolated nucleic acid molecule in an expressible format, said nucleic acid molecule comprising the coding region of a gene selected from the group consisting of flhB, fliR, ntrC, glnH, motA, motB, tlyC, ytfM, and ytfN genes, or a protein-encoding homologue, analogue or derivative thereof;

(ii) introducing the isolated nucleic acid molecule of (i) in an expressible format into a suitable vaccine vector; and (iii) incubating or growing the vaccine vector for a time and under conditions sufficient for expression of the immunogenic component encoded by said nucleic acid molecule to occur.

It will be apparent from the preceding discussion that the protein-encoding region of a flhB, fliR, ntrC, glnH, motA, motB, tlyC, ytfM, or ytfN gene comprises a nucleotide sequence selected from the group consisting of SEQ ID NOs:1, 3, 5, 7, 9, 11, 13, 15, and 17, or alternatively or in addition, a protein-encoding nucleotide sequence of *L. intracellularis* DNA contained within a deposited plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN).

Preferred homologues of the protein-encoding region of a flhB, fliR, ntrC, glnH, motA, motB, tlyC, ytfM, or ytfN gene include those nucleotide sequences selected from the group consisting of:

(i) a protein-encoding nucleotide sequence having at least about 60% sequence identity overall to a nucleotide sequence selected from the group consisting of SEQ ID NOs: 1, 3, 5, 7, 9, 11, 13, 15, and 17 or a degenerate variant thereof;

(ii) a protein-encoding nucleotide sequence having at least about 60% sequence identity overall to the protein-encoding sequence of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(iii) a protein-encoding nucleotide sequence which comprises at least about 15 contiguous nucleotides of a sequence selected from the group consisting of SEQ ID NOs: 1, 3, 5, 7, 9, 11, 13, 15, and 17;

(iv) a protein-encoding nucleotide sequence which comprises at least about 15 contiguous nucleotides of the protein-encoding sequence of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(v) a protein-encoding nucleotide sequence which hybridizes under at least low stringency conditions to the complement of a nucleotide sequence selected from the group consisting of SEQ ID NOs: 1, 3, 5, 7, 9, 11, 13, 15, and 17; and (vi) a protein-encoding nucleotide sequence which hybridizes under at least low stringency conditions to the non-coding strand of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN).

The present invention clearly extends to analogues or derivatives of any one of (i) to (vi) which encode a polypeptide which mimics a B-cell or T-cell epitope of *Lawsonia* spp.

For the present purpose, a preferred homologue of the protein-encoding region of a flhB, fliR, ntrC, glnH, motA, motB, tlyC, ytfM, or ytfN gene will have at least about 80% nucleotide sequence identity to the coding region of said gene, still more preferably at least about 90% identity, and yet still more preferably at least about 95% identity.

In determining whether or not two nucleotide sequences fall within these percentage limits, those skilled in the art will be aware that it is necessary to conduct a side-by-side comparison or multiple alignment of sequences. In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BESTFIT programme or other appropriate programme of the Computer Genetics Group, Inc., University Research Park, Madison, Wis., United States of America (Devereaux et al, 1984).

Preferably, a homologue of the protein-encoding region of a flhB, fliR, ntrC, glnH, motA, motB, tlyC, ytfM, or ytfN gene hybridizes under at least medium stringency conditions to the non-coding strand of said gene, even more preferably under high stringency conditions to the non-coding strand of said gene.

For the purposes of defining the level of stringency, a low stringency is defined herein as being a hybridisation and/or a wash carried out in 6×SSC buffer, 0.1% (w/v) SDS at 28° C. A moderate stringency is defined herein as being a hybridisation and/or washing carried out in 2×SSC buffer, 0.1% (w/v) SDS at a temperature in the range 45° C. to 65° C. A high stringency is defined herein as being a hybridisation and/or wash carried out in 0.1×SSC buffer, 0.1% (w/v) SDS, or lower salt concentration, and at a temperature of at least 65° C. Reference herein to a particular level of stringency encompasses equivalent conditions using wash/hybridization solutions other than SSC known to those skilled in the art.

Generally, the stringency is increased by reducing the concentration of SSC buffer, and/or increasing the concentration of SDS and/or increasing the temperature of the hybridisation and/or wash. Those skilled in the art will be aware that the conditions for hybridisation and/or wash may vary depending upon the nature of the hybridisation membrane or the type of hybridisation probe used. Conditions for hybridisations and washes are well understood by one normally skilled in the art. For the purposes of clarification of the parameters affecting hybridisation between nucleic acid molecules, reference is found in pages 2.10.8 to 2.10.16. of Ausubel et al. (1987), which is herein incorporated by reference.

As used herein, a "nucleic acid molecule in an expressible format" is a protein-encoding region of a nucleic acid molecule placed in operable connection with a promoter or other regulatory sequence capable of regulating expression in the vaccine vector system.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e., upstream activating sequences, enhancers and silencers) which alter gene expression in response to developmental and/or external stimuli, or in a tissue-specific manner. In the present context, the term "promoter" is also used to describe a recombinant, synthetic or fusion molecule, or derivative which confers, activates or enhances the expression of a nucleic acid molecule to which it is operably connected, and which encodes the immunogenic polypeptide. Preferred promoters can contain additional copies of one or more specific regulatory elements to further enhance expression and/or to alter the spatial expression and/or temporal expression of the said nucleic acid molecule.

Placing a nucleic acid molecule under the regulatory control of, i.e., "in operable connection with", a promoter sequence means positioning said molecule such that expression is controlled by the promoter sequence. Promoters are generally, but not necessarily, positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. Furthermore, the regulatory elements comprising a promoter are usually positioned within 2 kb of the start site of transcription of the gene. As is known in the art, some variation in this distance can be accommodated without loss of promoter function. Similarly, the-preferred positioning of a regulatory sequence element with respect to a heterologous gene to be placed under its control is defined by the positioning of the element in its natural setting, i.e., the genes from which it is derived. Again, as is known in the art, some variation in this distance can also occur.

The prerequisite for producing intact polypeptides in bacteria such as E. coli is the use of a strong promoter with an effective ribosome binding site. Typical promoters suitable for expression in bacterial cells such as E. coli include, but are not limited to, the lacz promoter, temperature-sensitive $\lambda_L$ or $\lambda_R$ promoters, T7 promoter or the IPTG-inducible tac promoter. A number of other vector systems for expressing the nucleic acid molecule of the invention in E. coli are well-known in the art and are described, for example, in Ausubel et al (1987) or Sambrook et al (1989). Numerous plasmids with suitable promoter sequences for expression in bacteria and efficient ribosome binding sites have been described, such as for example, pKC30 ($\lambda_L$: Shimatake and Rosenberg, 1981); pKK173-3 (tac: Amann and Brosius, 1985), pET-3 (T7: Studier and Moffat, 1986); the pBAD/TOPO or pBAD/Thio-TOPO series of vectors containing an arabinose-inducible promoter (Invitrogen, Carlsbad, Calif.), the latter of which is designed to also produce fusion proteins with thioredoxin to enhance solubility of the expressed protein; the pFLEX series of expression vectors (Pfizer Inc., CT, USA); or the pQE series of expression vectors (Qiagen, Calif.), amongst others. Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others.

Means for introducing the isolated nucleic acid molecule or a genetic construct comprising same into a cell for expression of the immunogenic component of the vaccine composition are well-known to those skilled in the art. The technique used for a given organism depends on the known successful techniques. Means for introducing recombinant DNA into animal cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., Wis., USA) amongst others.

The immunogenic component of a vaccine composition as contemplated herein exhibits excellent therapeutic activity, for example, in the treatment and/or prophylaxis of PPE when administered in an amount which depends on the particular case. For example, for recombinant polypeptide molecules, from about 0.5 $\mu$g to about 20 mg may be administered, preferably from about 1 $\mu$g to about 10 mg, more preferably from about 10 $\mu$g to about 5 mg, and most preferably from about 50 $\mu$g to about 1 mg equivalent of the immunogenic component in a volume of about 1 ml to about 5 ml. For DNA vaccines, a preferred amount is from about 0.1 $\mu$g/ml to about 5 mg/ml in a volume of about 1 to about 5 ml. The DNA can be present in "naked" form or it can be administered together with an agent facilitating cellular uptake (e.g., in liposomes or cationic lipids). The important feature is to administer sufficient immunogen to induce a protective immune response. The above amounts can be administered as stated or calculated per kilogram of body weight. Dosage regime can be adjusted to provide the optimum therapeutic response. For example, several divided doses can be administered or the dose can be proportionally reduced as indicated by the exigencies of the therapeutic situation. Booster administration may also be required.

The vaccine of the present invention can further comprise one or more additional immunomodulatory components such as, for example, an adjuvant or cytokine molecule, amongst others, that is capable of increasing the immune response against the immunogenic component. Non-limiting examples of adjuvants that can be used in the vaccine of the present invention include the RIBI adjuvant system (Ribi Inc., Hamilton, Mont., USA), alum, mineral gels such as aluminium hydroxide gel, oil-in-water emulsions, water-in-oil emulsions such as, for example, Block co-polymer (CytRx, Atlanta Ga., USA),QS-21 (Cambridge Biotech Inc., Cambridge Mass., USA), SAF-M (Chiron, Emeryville Calif., USA), AMPHIGEN® adjuvant, Freund's complete adjuvant; Freund's incomplete adjuvant; and Saponin, QuilA or other saponin fraction, monophosphoryl lipid A, and Avridine lipid-amine adjuvant. Other immunomodulatory agents that can be included in the vaccine include, for example, one or more cytokines, such as interferon and/or interleukin, or other known cytokines. Non-ionic surfactants such as, for example, polyoxyethylene oleyl ether and n-hexadecyl polyethylene ether may also be included in the vaccines of the present invention.

The vaccine composition can be administered in a convenient manner such as by oral, intravenous (where water soluble), intramuscular, subcutaneous, intranasal, intradermal or suppository routes or by implantation (eg., using slow release technology), provided that a sufficient degree of the immunogenicity of the immunizing antigen is retained for the purposes of eliciting an immune response in the animal being treated. Depending on the route of administration, the immunogenic component may be required to be coated in a material to protect it from the action of enzymes, acids and other natural conditions which may inactivate it, such as those in the digestive tract.

The vaccine composition may also be administered parenterally or intraperitoneally. Dispersions can also be prepared in glycerol, liquid polyethylene glycols, and mixtures thereof, or in oils. Under ordinary conditions of storage and use, these preparations can contain a preservative to prevent the growth of microorganisms. Alternatively, the vaccine composition can be stored in lyophilised form to be rehydrated with an appropriate vehicle or carrier prior to use.

Pharmaceutical forms suitable for injectable use include sterile aqueous solutions (where water soluble) or dispersions and sterile powders for the extemporaneous preparation of sterile injectable solutions or dispersion. In all cases the form must be fluid to the extent that easy syringability exists, unless the pharmaceutical form is a solid or semi-solid such as when slow release technology is employed. In any event, it must be stable under the conditions of manufacture and storage and must be preserved against the contaminating action of microorganisms.

The carrier may be a solvent or dispersion medium containing, for example, water, ethanol, polyol (for example, glycerol, propylene glycol and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents such as, for example, parabens, chlorobutanol, phenol, sorbic acid, thimerosal and the like. In many cases, it will be preferable to include isotonic agents such as, for example, sugars or sodium chloride. Prolonged absorption of the injectable compositions can be brought about by the use in the compositions of agents delaying absorption such as, for example, aluminum monostearate and gelatin.

Sterile injectable solutions are prepared by incorporating the active compound in the required amount in the appropriate solvent with various of the other ingredients enumerated above, as required, followed by filter-sterilization. Generally, dispersions are prepared by incorporating the sterilized active ingredient into a sterile vehicle which contains the basic dispersion medium and the required other ingredients selected from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The present invention extends to vaccine compositions which confer protection against infection by one or more isolates or sub-types of *L. intracellularis* including those that belong to the same serovar or serogroup as *L. intracellularis*. The vaccine composition preferably also confers protection against infection by other species of the genus *Lawsonia* or other microorganisms related thereto, as determined at the nucleotide, biochemical, structural, physiological and/or immunointeractive level; the only requirement being that said other species or other microorganism expresses a polypeptide which is immunologically cross-reactive to a polypeptide selected from the group consisting of flhB, fliR, ntrC, glnH, motA, motB, tlyC, ytfM, and ytfN polypeptides, or a homologue, analogue or derivative of any one or more of said polypeptides as described herein. For example, such related microorganisms may comprise genomic DNA which is at least about 70% identical overall to the genomic DNA of *L. intracellularis* as determined using standard genomic DNA hybridisation and analysis techniques.

The terms "serogroup" and "serovar" relate to a classification of microorganisms which is based upon serological typing data, in particular data obtained using agglutination assays such as the microscopic agglutination test (MAT). Those skilled in the art will be aware that serovar and serogroup antigens are a mosaic on the cell surface and, as a consequence there will be no strict delineation between bacteria belonging to a serovar and/or serogroup. Moreover, organisms which belong to different species may be classified into the same serovar or serogroup because they are indistinguishable by antigenic determination. As used herein, the term "serovar" means one or more *Lawsonia* strains which are antigenically-identical with respect to antigenic determinants produced by one or more loci. Quantitatively, serovars may be differentiated from one another by cross-agglutination absorption techniques. As used herein, the term "serogroup" refers to a group of *Lawsonia* spp. whose members cross-agglutinate with shared group antigens and do not cross-agglutinate with the members of other groups and, as a consequence, the members of a serogroup have more or less close antigenic relations with one another by simple cross-agglutination.

The present invention thus clearly extends to vaccine compositions for the treatment and/or prophylaxis of animals, in particular, vaccine compositions for the treatment and/or prophylaxis of porcine and/or avian species, against any bacterium belonging to the same serovar or serogroup as *L. intracellularis*. Preferably, such organisms will express a polypeptide homologue, analogue or derivative of a polypeptide selected from the group consisting of flhB, fliR, ntrC, glnH, motA, motB, tlyC, ytfM, and ytfN polypeptides.

The present invention extends further to vaccine compositions capable of conferring protection against a "genetic variant" of *L. intracellularis*, the only requirement being that said variant expresses a polypeptide which is immunologically cross-reactive to a polypeptide selected from the group consisting of flhB, fliR, ntrC, glnH, motA, motB, tlyC, ytfM, and ytfN polypeptides. Genetic variants of *L. intracellularis* can be developed by mutation, recombination, conjugation or transformation of *L. intracellularis* or may occur naturally. It will be known to a person skilled in the art how to produce such derivatives.

In a particularly preferred embodiment, the vaccine composition of the invention is intended for or suitable for the prophylaxis and/or treatment of infection in a porcine or avian animal and more preferably, for prophylaxis and/or treatment of a porcine animal for infection by *L. intracellularis*.

Accordingly, the present invention clearly extends to the use of the immunogenic polypeptide of the invention or a DNA or RNA molecule encoding the same, according to any one of the preceding embodiments or as exemplified herein in the preparation of a medicament for the treatment and/or prophylaxis of PPE in animals, particularly porcine or avian animals.

The invention further extends to a method of treatment and/or prophylaxis of PPE in an animal such as an avian or porcine animal, said method comprising administering the vaccine composition or the immunogenic polypeptide of the invention or a DNA or RNA molecule encoding the same, as described or exemplified herein to said animal for a time and under conditions sufficient for an immune response to occur thereto. Preferably, in the case of administration of a vaccine composition, the immune response to the immunogen is a protective immune response.

Those skilled in the art will recognise the general applicability of the invention in vaccinating animals other than porcine and avian animals against *L. intracellularis* and/or related microorganisms. In the general application of the vaccine of the present invention, the only prerequisite is that the animal on which protection is conferred is capable of being infected with *L. intracellularis* and/or a related microorganism thereto and that, in the case of a related microorganism to *L. intracellularis*, said related microorganism expresses a B-cell or T-cell epitope which mimics or cross-reacts with the polypeptide component of the vaccine composition described herein. Animals which may be protected by the vaccine of the present invention include, but are not limited to, humans, primates, companion animals (e.g., cats, dogs), livestock animals (e.g., pigs, sheep, cattle, horses, donkeys, goats), laboratory test animals (e.g., mice, rats, guinea pigs, rabbits) and captive wild animals (e.g., kangaroos, foxes, deer). The present invention also extends to the vaccination of birds such as poultry birds, game birds and caged birds.

The present invention further extends to combination vaccines comprising an effective amount of a first immunogenic component comprising a polypeptide selected from the group consisting of flhB, fliR, ntrC, glnH, motA, motB, tlyC, ytfM, and ytfN polypeptides, or a homologue, analogue or derivative thereof as described herein, or a DNA or RNA molecule encoding the same, combined with an effective amount of a second immunogenic component comprising one or more other antigens capable of protecting a porcine animal, or bird, against either *Lawsonia* spp. or another pathogen that infects and causes disease in said animal. The second immunogenic component is different from the first immunogenic component and is preferably selected from the group consisting of the *L. intracellularis* FlgE, hemolysin, OmpH, SodC, flhB, fliR, ntrC, glnH, motA, motB, tlyC, ytfM, and ytfN polypeptides and homologues, analogues or derivatives thereof. The present invention clearly extends to DNA vaccines and vaccine vectors which express said first immunogenic component and said second immunogenic component.

It is within the scope of the invention to encompass vaccine compositions comprising multimeric and polymeric forms of any one or more of the immunogenic polypeptides described herein, such as tandem arrays of homologous amino acid sequences, or, alternatively, tandem arrays of heterologous immunogenic repeats of amino acid sequences. The present invention extends further to nucleic acid molecules encoding such polymeric forms.

The isolated or recombinant polypeptide of the invention, or an immunologically-equivalent homologue, analogue or derivative thereof is also useful for the preparation of immunologically interactive molecules which are useful in the diagnosis of infection of an animal by *Lawsonia* spp., in particular by *L. intracellularis* or a related organism thereto.

As used herein, the term "immunologically interactive molecule" includes antibodies and antibody derivatives and functional equivalents, such as a Fab, or a SCAB (single-chain antibody), any of which optionally can be conjugated to an enzyme, radioactive or fluorescent tag, amongst others. The only requirement of such immunologically interactive molecules is that they are capable of binding specifically to the immunogenic polypeptide of the present invention as hereinbefore described.

Accordingly, a further aspect of the invention extends to an immunologically interactive molecule which is capable of binding to a polypeptide selected from the group consisting of:

(i) a polypeptide which comprises an amino acid sequence which has at least about 60% sequence identity overall to an amino acid sequence selected from the group consisting of SEQ ID NOs: 2, 4, 6, 8, 10, 12, 14, 16, and 18;

(ii) a polypeptide which comprises an amino acid sequence which has at least about 60% sequence identity overall to an amino acid sequence encoded by *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(iii) a polypeptide which comprises at least about 5 contiguous amino acids of an amino acid sequence selected from the group consisting of SEQ ID NOs: 2, 4, 6, 8, 10, 12, 14, 16, and 18;

(iv) a polypeptide which comprises at least about 5 contiguous amino acids of an amino acid sequence encoded by *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(v) a polypeptide which comprises an amino acid sequence encoded by a nucleotide sequence having at least about 60% sequence identity overall to a nucleotide sequence selected from the group consisting of SEQ ID NOs: 1, 3, 5, 7, 9, 11, 13, 15, and 17;

(vi) a polypeptide which comprises an amino acid sequence encoded by a nucleotide sequence having at least about 60% sequence identity overall to the nucleotide sequence of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(vii) a polypeptide encoded by at least about 15 contiguous nucleotides of a nucleotide sequence selected from the group consisting of SEQ ID NOs: 1, 3, 5, 7, 9, 11, 13, 15, and 17;

(viii) a polypeptide encoded by at least about 15 contiguous nucleotides of a nucleotide sequence of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN); and (ix) a homologue, analogue or derivative of any one of (i) to (viii) which mimics a B-cell or T-cell epitope of *Lawsonia* spp.

In a preferred embodiment, the immunologically interactive molecule is an antibody that binds specifically to one or more epitopes of a polypeptide selected from the group consisting of flhB, fliR, ntrC, glnH, motA, motB, tlyC, ytfM, and ytfN polypeptides. More preferably, the immunologically interactive molecule binds specifically to one or more epitopes of a polypeptide from a causative agent of PPE, such as, for example, *L. intracellularis*.

Conventional methods can be used to prepare the immunologically interactive molecules. For example, by using a polypeptide immunogen of the present invention, polyclonal antisera or monoclonal antibodies can be made using standard methods. For example, a mammal, (e.g., a mouse, hamster, or rabbit) can be immunized with an immunogenic form of the polypeptide of the present invention which elicits an antibody response in the mammal. Techniques for conferring immunogenicity on a polypeptide include conjugation to carriers, or other techniques well known in the art. For example, the polypeptide can be administered in the presence of adjuvant or can be coupled to a carrier molecule, as known in the art, that enhances the immunogenicity of the polypeptide. The progress of immunization can be monitored by detection of antibody titres in plasma or serum. Standard ELISA or other immunoassay can be used with the immunogen as antigen to assess the levels of antibodies. Following immunization, antisera can be obtained and, for example, IgG molecules corresponding to the polyclonal antibodies can be isolated from the antisera.

To produce monoclonal antibodies, antibody producing cells (lymphocytes) can be harvested from an animal immunised with a polypeptide of the present invention and fused with myeloma cells by standard somatic cell fusion procedures, thus immortalizing these cells and yielding hybridoma cells. Such techniques are well known in the art, for example, the hybridoma technique originally developed by Kohler and Milstein (1975), as well as other techniques such as the human B-cell hybridoma technique (Kozbor et al., 1983), the EBV-hybridoma technique to produce human monoclonal antibodies (Cole et al., 1985), and screening of combinatorial antibody libraries (Huse et al., 1989). Hybridoma cells can be isolated and screened immunochemically for production of antibodies that are specifically reactive with the polypeptide and monoclonal antibodies isolated therefrom.

As with all immunogenic-compositions for eliciting antibodies, the immunogenically effective amounts of the peptides of the invention must be determined empirically. Factors to be considered include the immunogenicity of the native polypeptide, whether or not the polypeptide will be complexed with or covalently attached to an adjuvant or carrier protein or other carrier, the route of administration for the composition, i.e., intravenous, intramuscular, subcutaneous, etc., and the number of immunizing doses to be administered. Such factors are known in the vaccine art and it is well within the skill of immunologists to make such determinations without undue experimentation.

The term "antibody" as used herein, is intended to include fragments thereof which are also specifically reactive with a polypeptide that mimics or cross-reacts with a B-cell or T-cell epitope of the L. intracellularis polypeptide selected from the group consisting of flhB, fliR, ntrC, glnH, motA, motB, tlyC, ytfM, and ytfN polypeptides. Antibodies can be fragmented using conventional techniques and the fragments screened for utility in the same manner as described above for whole antibodies. For example, F(ab')2 fragments can be generated by treating antibody with pepsin. The resulting F(ab')2 fragment can be treated to reduce disulfide bridges to produce Fab' fragments.

It is within the scope of this invention to include any secondary antibodies (monoclonal, polyclonal or fragments of antibodies), including anti-idiotypic antibodies, directed to the first mentioned antibodies discussed above. Both the first and second antibodies can be used in detection assays or a first antibody can be used with a commercially available anti-immunoglobulin antibody. An antibody as contemplated herein includes any antibody specific to any region of a polypeptide which mimics, or cross-reacts with a B-cell or T-cell epitope of a L. intracellularis polypeptide selected from the group consisting of flhB, fliR, ntrC, glnH, motA, motB, tlyC, ytfM, and ytfN polypeptides.

The antibodies described herein are useful for determining B-cell or T-cell epitopes of a polypeptide selected from the group consisting of flhB, fliR, ntrC, glnH, motA, motB, tlyC, ytfM, and ytfN polypeptides, such as, for example, by testing the ability of synthetic peptides to cross-react immunologically with said polypeptide or to elicit the production of antibodies which cross-react with said polypeptide. Using methods described herein, polyclonal antibodies, monoclonal antibodies or chimeric monoclonal antibodies can also be raised to peptides which mimic or cross-react with a B-cell or T-cell epitope of a L. intracellularis polypeptide selected from the group consisting of flhB, fliR, ntrC, glnH, motA, motB, tlyC, ytfM, and ytfN polypeptides.

More particularly, the polyclonal, monoclonal or chimeric monoclonal antibodies can be used to detect the polypeptide of the invention and/or any homologues, analogues or derivatives thereof, in various biological materials. For example, they can be used in an ELISA, radioimmunoassay, or histochemical test. In other words, the antibodies can be used to test for binding to a polypeptide of the invention or to a homologue, analogue or derivative thereof, in a biological sample to diagnose the presence of L. intracellularis therein.

Accordingly, a further aspect of the invention provides a method of diagnosing infection of an animal by L. intracellularis or a related microorganism thereto, said method comprising the steps of contacting a biological sample derived from said animal with an immunologically interactive molecule which is capable of binding to a polypeptide selected from the group consisting of flhB, fliR, ntrC, glnH, motA, motB, tlyC, ytfM, and ytfN polypeptides, or a homologue, analogue or derivative thereof, for a time and under conditions sufficient for an antigen:antibody complex to form, and detecting said complex formation.

According to this embodiment of the present invention, the immunologically interactive molecule is preferably an antibody molecule prepared against a L. intracellularis polypeptide selected from the group consisting of flhB, fliR, ntrC, glnH, motA, motB, tlyC, ytfM, and ytfN polypeptides, or an analogue or derivative thereof.

If the biological sample being tested contains one or more epitopes of a polypeptide selected from the group consisting of flhB, fliR, ntrC, glnH, motA, motB, tlyC, ytfM, and ytfN polypeptides, or an immunologically cross-reactive homologue, analogue or derivative thereof, it will give a positive binding result to the immunologically interactive molecule.

Preferably, the biological sample is derived from a porcine or avian host of the pathogen L. intracellularis or a related microorganism thereto, and includes an appropriate tissue or fluid sample from the animal.

Preferred biological samples are derived from the ileum, caecum, small intestine, large intestine, whole serum or lymph nodes of the porcine or avian host animal being tested. Alternatively or in addition the biological test sample may comprise faeces or a rectal swab derived from the animal.

To distinguish L. intracellularis from other microorganisms resident in the gut or other organ of an animal, the antibodies should not be prepared against highly-conserved epitopes of the L. intracellularis polypeptide, such as, for example, those amino acid sequences of at least 5 amino acids in length which are conserved between *L. intracellularis* and a microorganism which is present in the gut or other organ of an animal in respect of which diagnosis is sought such as, for example, *E.coli.*

Conventional immunoassays can be used to perform this embodiment of the invention. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as the traditional competitive binding assays. These assays also include direct binding of a labelled antibody to a target. It will be readily apparent to the skilled technician how to modify or optimise such assays to perform this embodiment of the present invention, and all such modifications and optimisations are encompassed by the present invention.

In one alternative embodiment, the present invention contemplates a method of identifying whether or not an animal has suffered from a past infection, or is currently infected with *L. intracellularis* or a related microorganism thereto, said method comprising contacting blood or serum derived from said animal with the immunogenic polypeptide of the invention for a time and under conditions sufficient for an antigen:antibody complex to form, and detecting said complex formation. This embodiment differs from the embodiment described supra in that it relies upon the detection of circulating antibodies against *L. intracellularis* or related organism in the animals blood or serum which are present as a consequence of a past or present infection by this pathogen. However, it will be apparent to those skilled in the art that the principle of the assay format is the same. As with other embodiments of the invention referred to supra, conventional immunoassays can be used. Persons skilled in the art will readily be capable of varying known immunoassay formats to perform the present embodiment. This embodiment of the invention can also utilise derivatives of blood and serum which comprise immunologically interactive molecules such as, for example, partially-purified IgG or IgM fractions and buffy coat samples, amongst others. The preparation of such fractions will also be known to those skilled in the art.

A further aspect of the present invention provides an isolated nucleic acid molecule which comprises a sequence of nucleotides that encodes, or is complementary to a nucleic acid molecule that encodes a polypeptide selected from the group consisting of flhB, fliR, ntrC, glnH, motA, motB, tlyC, ytfM, and ytfN polypeptides, including any and all genes selected from the group consisting of flhB, fliR, ntrC, glnH, motA, motB, tlyC, ytfM, and ytfN genes as defined hereinabove.

In a preferred embodiment, the isolated nucleic acid molecule comprises a nucleotide sequence encoding a polypeptide that is immunologically cross-reactive with *L. intracellularis* or other causative agent of PPE, wherein said nucleotide sequence is selected from the group consisting of:

(i) a nucleotide sequence having at least about 60% sequence identity overall to a nucleotide sequence selected from the group consisting of SEQ ID NOs: 1, 3, 5, 7, 9, 11, 13, 15, and 17;

(ii) a nucleotide sequence having at least about 60% sequence identity overall to *L. intracellularis* DNA contained within a plasmid selected from the group consisting of AGAL Accession Nos: NM00/16476 (plasmid pGTE#1 glnH); NM0016477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00116481 (plasmid pGTE#6 ntrC); NM00/16482 (plasmid pGTE#7 ytfM); and NM01/23286 (plasmid pGTE#8 ytfN);

(iii) a nucleotide sequence which comprises at least about 15 contiguous nucleotides of a sequence selected from the group consisting of SEQ ID NOs: 1, 3, 5, 7, 9, 11, 13, 15, and 17;

(iv) a nucleotide sequence which comprises at least about 15 contiguous nucleotides of *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);

(v) a nucleotide sequence which hybridizes under at least low stringency conditions to a nucleotide sequence selected from the group consisting of SEQ ID NOs: 1, 3, 5, 7, 9, 11, 13,15, and 17 or a complementary nucleotide sequence thereto;

(vi) a nucleotide sequence which hybridizes under at least low stringency conditions to *L. intracellularis* DNA contained within a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN); and (vii) a homologue, analogue or derivative of any one of (i) to (vi) which encodes a polypeptide which mimics a B-cell or T-cell epitope of *Lawsonia* spp.

For the present purpose, a "homologue" of a nucleotide sequence shall be taken to refer to an isolated nucleic acid molecule which encodes a polypeptide that is immunologically cross-reactive to a polypeptide selected from the group consisting of flhB, fliR, ntrC, glnH, motA, motB, tlyC, ytfM, and ytfN polypeptides, but which includes one or more nucleotide substitutions, insertions, deletions, or rearrangements.

An "analogue" of a nucleotide sequence set forth herein shall be taken to refer to an isolated nucleic acid molecule which encodes a polypeptide which is immunologically cross-reactive to a polypeptide selected from the group consisting of flhB, fliR, ntrC, glnH, motA, motB, tlyC, ytfM, and ytfN polypeptides, but which includes one or more non-nucleotide constituents not normally present in said isolated nucleic acid molecule, such as, for example, carbohydrates, radiochemicals including radio nucleotides, reporter molecules such as, but not limited to biotin, DIG, alkaline phosphatase or horseradish peroxidase, amongst others.

A "derivative" of a nucleotide sequence set forth herein shall be taken to refer to any isolated nucleic acid molecule which contains at least about 60% nucleotide sequence identity to 15 or more contiguous nucleotides present in the nucleotide sequence of a gene selected from the group consisting of flhB, fliR, ntrC, glnH, motA, motB, tlyC, ytfM, and ytfN genes.

Generally, a flhB, fliR, ntrC, glnH, motA, motB, tlyC, ytfM, or ytfN gene may be subjected to mutagenesis to produce single or multiple nucleotide substitutions, deletions and/or insertions. Nucleotide insertional derivatives include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of the gene, although random insertion is also possible with suitable screening of the resulting product being performed. Deletional nucleotide sequence variants are characterised by the removal of one or more nucleotides from the gene. Substitutional nucleotide sequence variants are those in which at least one nucleotide in the gene sequence has been removed and a different nucleotide or nucleotide analogue inserted in its place. In a preferred embodiment, such substitutions are selected based on the degeneracy of the genetic code, as known in the art, with the resulting substitutional variant encoding the amino acid sequence of a flhB, fliR, ntrC, glnH, motA, motB, tlyC, ytfM, or ytfN polypeptide.

Preferred homologues, analogues and derivatives of a flhB, fliR, ntrC, glnH, motA, motB, tlyC, ytfM, or ytfN gene comprise a sequence of nucleotides which has at least about 80%identity, even more preferably at least about 90% identity, and yet still more preferably at least about 95% identity to said gene.

In determining whether or not two nucleotide sequences fall within these percentage limits, reference is made to the description supra of methods for conducting a side-by-side comparison or multiple alignment of nucleotide sequences.

Alternatively or in addition, preferred homologues, analogues and derivatives of a flhB, fliR, ntrC, glnH, motA, motB, tlyC, ytfM, or ytfN gene comprise a sequence of nucleotides which hybridizes under at least moderate stringency conditions and to the nucleotide sequence of said gene, or to a nucleic acid fragment comprising at least about 20 contiguous nucleotides in length derived therefrom, and even more preferably, under high stringency conditions to said gene, or to said nucleic acid fragment. For the purposes of defining the level of stringency, reference is made to the description hereinabove of hybridization stringencies.

In a more preferred embodiment, such a nucleotide sequence encodes a polypeptide that is immunologically cross-reactive with L. intracellularis or other causative agent of PPE.

In a particularly preferred embodiment, the isolated nucleic acid molecule of the present invention comprises or consists of a nucleotide sequence selected from the group consisting of:

(i) a nucleotide sequence selected from the group consisting of SEQ ID NOs: 1, 3, 5, 7, 9, 11, 13, 15, and 17;
(ii) a nucleotide sequence of the L. intracellularis DNA contained within a deposited plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN);
(iii) a nucleotide sequence that encodes the same polypeptide as (i) or (ii), wherein said polypeptide is selected from the group consisting of flhB, fliR, ntrC, glnH, motA, motB, tlyC, ytfM, and ytfN polypeptides; and
(iv) a nucleotide sequence that is complementary to (i) or (ii) or (iii).

The present invention clearly encompasses genetic constructs comprising the subject nucleic acid molecule in an expressible format suitable for the preparation of a recombinant immunogenic polypeptide selected from the group consisting of flhB, fliR, ntrC, glnH, motA, motB, tlyC, ytfM, and ytfN polypeptides, such as for use in recombinant univalent or polyvalent recombinant vaccines.

In such cases, the nucleic acid molecule will be operably connected to a promoter sequence which can thereby regulate expression of said nucleic acid molecule in a prokaryotic or eukaryotic cell as described supra.

The genetic construct optionally further comprises a terminator sequence. The term "terminator" refers to a DNA sequence at the end of a transcriptional unit which signals termination of transcription. A "terminator" is a nucleotide sequence, generally located within the 3'-non-translated region of a gene or mRNA, comprising a polyadenylation signal to facilitate the post-transcriptional addition of a polyadenylate sequence to the 3'-end of a primary mRNA transcript. Terminator sequences may be isolated from the genetic sequences of bacteria, fungi, viruses, animals and/or plants. Terminators active in animal cells are known and described in the literature.

In a preferred embodiment, the genetic construct can be a cloning or expression vector, as known in the art, such as a plasmid, cosmid, or phage, comprising a nucleic acid molecule of the present invention, and host cells transformed or transfected therewith. In a non-limiting embodiment, the vector is a plasmid selected from the group consisting of AGAL Accession Nos: NM00/16476 (plasmid pGTE#1 glnH); NM00/16477 (plasmid pGTE#2 flhB); NM00/16478 (plasmid pGTE#3 fliR); NM00/16479 (plasmid pGTE#4 motA/B); NM00/16480 (plasmid pGTE#5 tlyC); NM00/16481 (plasmid pGTE#6 ntrC); NM00/16482 (plasmid pGTE#7 ytfM); and NM01/23286 (plasmid pGTE#8 ytfN).

The genetic constructs of the present invention are particularly useful for producing the immunogenic component of the vaccine composition described herein or for use in a DNA vaccine.

A range of genetic diagnostic assays to detect infection of an animal by L. intracellularis or a related microorganism can be employed using the nucleic acid molecule described herein such as, for example, assays based upon the polymerase chain reaction (PCR) and nucleic acid hybridisation. All such assays are contemplated in the present invention.

Accordingly, a still further aspect of the invention provides a diagnostic method of detecting L. intracellularis or related microorganism in a biological sample derived from an animal subject, said method comprising the steps of hybridising one or more probes or primers derived from a nucleotide sequence of a flhB, fliR, ntrC, glnH, motA, motB, tlyC, ytfM, or ytfN gene as defined hereinabove, or a homologue, analogue or derivative thereof, to a DNA or RNA molecule present in said sample and then detecting said hybridisation using a detection means.

As used herein, the term "probe" refers to a nucleic acid molecule which is capable of being used in the detection of a gene selected from the group consisting of flhB, fliR, ntrC, glnH, motA, motB, tlyC, ytfM, and ytfN genes. Probes may comprise DNA (single-stranded or double-stranded) or RNA (i.e., riboprobes) or analogues thereof.

The term "primer" refers to a probe as hereinbefore defined which is further capable of being used to amplify a nucleotide sequence from L. intracellularis or a related microorganism thereto in a PCR.

Preferred probes and primers include fragments of a gene selected from the group consisting of flhB, fliR, ntrC, glnH, motA, motB, tlyC, ytfM, and ytfN genes, including synthetic single-stranded DNA or RNA molecules of at least about 15 nucleotides in length.

Preferably, probes and primers according to this embodiment will comprise at least about 20 contiguous nucleotides in length from a gene selected from the group consisting of flhB, fliR, ntrC, glnH, motA, motB, tlyC, ytfM, and ytfN genes, even more preferably at least about 25 contiguous nucleotides, still even more preferably at least about 50 contiguous nucleotides, and even more preferably at least about 100 nucleotides to about 500 nucleotides in length from said gene. Probes and primers comprising the full-length gene or a complementary nucleotide sequence thereto are also encompassed by the present invention.

Probes or primers can comprise inosine, adenine, guanine, thymidine, cytidine or uracil residues or functional analogues or derivatives thereof that are capable of being incorporated into a polynucleotide molecule, provided that the resulting probe or primer is capable of hybridising under at least low stringency conditions to a gene selected from the group consisting of flhB, fliR, ntrC, glnH, motA, motB, tlyC, ytfM, and ytfN genes, or is at least about 60% identical to one strand of said gene.

The biological sample according to this aspect of the invention includes any organ, tissue, cell or exudate which contains or is likely to contain L. intracellularis or a nucleic acid derived therefrom. A biological sample can be prepared in a suitable solution such as, for example, an extraction buffer or suspension buffer. The present invention extends to the testing of biological solutions thus prepared, the only requirement being that said solution at least comprises a biological sample as described herein.

The diagnostic assay of the present invention is useful for the detection of *L. intracellularis* or a microorganism which is related thereto which expresses a polypeptide selected from the group consisting of flhB, fliR, ntrC, glnH, motA, motB, tlyC, ytfM, and ytfN polypeptides.

The present invention clearly contemplates diagnostic assays which are capable of both genus-specific and species-specific detection. Accordingly, in one embodiment, the probe or primer, or a homologue, analogue or derivative thereof, comprises DNA capable of being used to detect multiple *Lawsonia* spp. In an alternative embodiment, the probe or primer or a homologue, analogue or derivative thereof comprises DNA capable of being used to distinguish *L. intracellularis* from related microorganisms.

Less-highly conserved regions within the flhB, fliR, ntrC, glnH, motA, motB, tlyC, ytfM, or ytfN genes are particularly useful as species-specific probes and/or primers for the detection of *L. intracellularis* and very closely related species.

Furthermore, the diagnostic assays described herein can be adapted to a genus-specific or species-specific assay by varying the stringency of the hybridisation step. Accordingly, a low stringency hybridisation can be used to detect several different species of *Lawsonia* in one or more biological samples being assayed, while a high stringency hybridisation can be used to distinguish *L. intracellularis* from such other species.

The detection means according to this aspect of the invention may be any nucleic acid-based detection means such as, for example, nucleic acid hybridisation techniques or paper chromatography hybridisation assay (PACHA), or an amplification reaction such as PCR, or nucleic acid sequence-based amplification (NASBA) system. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR), in situ polymerase chain reaction and reverse transcription polymerase chain reaction (RT-PCR), amongst others.

Where the detection means is a nucleic acid hybridisation technique, the probe can be labelled with a reporter molecule capable of producing an identifiable signal (e.g., a radioisotope such as $^{32}P$ or $^{35}S$, or a biotinylated molecule). According to this embodiment, those skilled in the art will be aware that the detection of said reporter molecule provides for identification of the probe and that, following the hybridisation reaction, the detection of the corresponding nucleotide sequences in the biological sample is facilitated. Additional probes can be used to confirm the assay results obtained using a single probe.

A variation of the nucleic acid hybridisation technique contemplated by the present invention is the paper chromatography hybridisation assay (PACHA) described by Reinhartz et al. (1993) and equivalents thereof, wherein a target nucleic acid molecule is labelled with a reporter molecule such as biotin, applied to one end of a nitrocellulose or nylon membrane filter strip and subjected to chromatography under the action of capillary or other forces (e.g., an electric field) for a time and under conditions sufficient to promote migration of said target nucleic acid along the length of said membrane to a zone at which a DNA probe is immobilised thereto such as, for example, in the middle region. According to this detection format, labelled target nucleic acid comprising the *Lawsonia* spp. nucleotide sequences complementary to the probe will hybridise thereto and become immobilised in that region of the membrane to which the probe is bound. Non-complementary sequences to the probe will diffuse past the site at which the probe is bound. The target nucleic acid may comprise a crude or partially-pure extract of DNA or RNA or, alternatively, an amplified or purified DNA. Additional variations of this detection means which utilise the nucleotide sequences described herein are clearly encompassed by the present invention.

Wherein the detection means is a RFLP, nucleic acid derived from the biological sample, in particular DNA, is digested with one or more restriction endonuclease enzymes and the digested DNA is subjected to electrophoresis, transferred to a solid support such as, for example, a nylon or nitrocellulose membrane, and hybridised to a probe optionally labelled with a reporter molecule as hereinbefore defined. According to this embodiment, a specific pattern of DNA fragments is displayed on the support, wherein said pattern is preferably specific for a particular *Lawsonia* spp., to enable the user to distinguish between different species of the bacterium.

Wherein the detection means is an amplification reaction such as, for example, a polymerase chain reaction or a nucleic acid sequence-based amplification (NASBA) system or a variant thereof, one or more nucleic acid primer molecules of at least 15 contiguous nucleotides in length derivable from a gene selected from the group consisting of flhB, fliR, ntrC, glnH, motA, motB, tlyC, ytfM, and ytfN genes is hybridised to nucleic acid derived from a biological sample, and nucleic acid copies of the FlgE-encoding genetic sequences in said sample, or a part or fragment thereof, are enzymically-amplified.

Those skilled in the art will be aware that there must be a sufficiently high percentage of nucleotide sequence identity between the primers and the sequences in the biological sample template molecule to which they hybridise (i.e., the "template molecule"). As stated previously, the stringency conditions can be selected to promote hybridisation.

Preferably, each primer is at least about 95% identical to a region of a gene selected from the group consisting of flhB, flhR, ntrC, glnH, motA, motB, tlyC, ytfM, and ytfN genes in the template molecule to which it hybridises.

Those skilled in the art will also be aware that, in one format, PCR provides for the hybridisation of non-complementary primers to different strands of the template molecule, such that the hybridised primers are positioned to facilitate the 5'→3' synthesis of nucleic acid in the intervening region, under the control of a thermostable DNA polymerase enzyme. As a consequence, PCR provides an advantage over other detection means in so far as the nucleotide sequence in the region between the hybridised primers may be unknown and unrelated to any known nucleotide sequence.

In an alternative embodiment, wherein the detection means is AFLP, the primers are selected such that, when nucleic acid derived from the biological sample, in particular DNA, is amplified, different length amplification products are produced from different Lawsonia spp. The amplification products can be subjected to electrophoresis, transferred to a solid support such as, for example, a nylon or nitrocellulose membrane, and hybridised to a probe optionally labelled with a reporter molecule as hereinbefore described. According to this embodiment, a specific pattern of amplified DNA fragments is displayed on the support, said pattern optionally specific for a particular Lawsonia ssp., to enable the user to distinguish between different species of the bacterium in much the same way as for RFLP analysis.

The technique of AMD facilitates, not only the detection of Lawsonia spp. DNA in a biological sample, but also the determination of nucleotide sequence variants which differ from the primers and probes used in the assay format. Wherein the detection means is AMD, the probe is end-labelled with a suitable reporter molecule and mixed with an excess of the amplified template molecule. The mixtures are subsequently denatured and allowed to renature to form nucleic acid "probe:template hybrid molecules" or "hybrids", such that any nucleotide sequence variation between the probe and the temple molecule to which it is hybridised will disrupt base-pairing in the hybrids. These regions of mismatch are sensitive to specific chemical modification using hydroxylamine (mismatched cytosine residues) or osmium tetroxide (mismatched thymidine residues), allowing subsequent cleavage of the modified site using piperidine. The cleaved nucleic acid may be analysed using denaturing polyacrylamide gel electrophoresis, followed by standard nucleic acid hybridisation as described supra, to detect the Lawsonia-derived nucleotide sequences. Those skilled in the art will be aware of the means of end-labelling a genetic probe according to the performance of the invention described in this embodiment.

According to this embodiment, the use of a single end-labelled probe allows unequivocal localisation of the sequence variation. The distance between the point(s) of sequence variation and the end-label is represented by the size of the cleavage product.

In an alternative embodiment of AMD, the probe is labelled at both ends with a reporter molecule, to facilitate the simultaneous analysis of both DNA strands.

Wherein the detection means is RT-PCR, the nucleic acid sample comprises an RNA molecule which is a transcription product of Lawsonia-derived DNA or a homologue, analogue or derivative thereof. As a consequence, this assay format is particularly useful when it is desirable to determine expression of one or more Lawsonia genes. According to this embodiment, the RNA sample is reverse-transcribed to produce the complementary single-stranded DNA which is subsequently amplified using standard procedures.

Variations of the embodiments described herein are described in detail by McPherson et al. (1991).

The present invention clearly extends to the use of any and all detection means referred to supra for the purposes of diagnosing Lawsonia spp. and in particular L. intracellularis infection in animals.

The amplification reaction detection means described supra can be further coupled to a classical hybridisation reaction detection means to further enhance sensitivity and specificity of the inventive method, such as by hybridising the amplified DNA with a probe which is different from any of the primers used in the amplification reaction.

Similarly, the hybridisation reaction detection means described supra can be further coupled to a second hybridisation step employing a probe which is different from the probe used in the first hybridisation reaction.

A further aspect of the invention provides an isolated probe or primer derived from a gene selected from the group consisting of flhB, fliR, ntrC, glnH, motA, motB, tlyC, ytfM, and ytfN genes. Preferably, the probe or primer of the invention comprises a nucleotide sequence selected from the group consisting of SEQ ID NO: 19 to SEQ ID NO: 68 or a complementary nucleotide sequence thereto.

The present invention does not extend to any nucleic acid or polypeptide of Camplylobacter or Helicobacter that was disclosed publicly before the filing date or priority date of this application, or otherwise takes priority over the instant application, and which is homologous to a nucleotide sequence or amino acid sequence of Lawsonia spp. disclosed herein.

The present invention is further described with reference to the following non-limiting Examples.

EXAMPLE 1

Molecular Cloning of Lawsonia Intracellularis Genes

Isolation of DNA and Construction of DNA Libraries

L. intracellularis DNA was purified from pig intestinal mucosa isolated from the ileum of pigs experimentally infected with L. intracellularis. DNA purification from homogenized intestinal mucosa was performed according to the method of Nollau et al. (1996); or alternatively, by phenol extraction and sodium acetate-ethanol precipitation of DNA.

To facilitate cloning of L. intracellularis gene sequences, several genomic libraries were constructed. These libraries were specifically modified by ligation of a known sequence (Vectorette II™, Genosys Biotechnologies, Inc., The Woodlands, Tex.) to the 5'- and 3'-ends of restricted DNA fragments. Vectorette™ libraries were constructed by separately digesting aliquots of L. intracellularis-infected pig mucosal DNA extract with restriction endonucleases HindIII, EcoRI, DraI or HpaI at 37° C. overnight. The reaction was then spiked with additional fresh restriction enzyme and adjusted to 2 mM ATP, 2 mM DTT final concentration. Vectorette™ tailing was carried out by addition of $T_4$ DNA Ligase (1 unit) plus 3 pMol of the appropriate compatible Vectorette™ linker (HindIII Vectorette™: HindIII-digested DNA; EcoRI: EcoRI digested DNA; Blunt: DraI-, HpaI-digested DNA). The mixture was incubated for three cycles, each cycle consisting of 20° C. for 60 min; followed by 37° C. for 30 min, to complete the tailing reaction. Reaction volumes were then adjusted to 200 µl with water, and reactions were stored at −20° C.

EXAMPLE 2

Expression of the YtfN and YtfM genes of L. intracellularis i) Isolation of a C-Terminal Fragment of ytfN Gene by Genome Walking The complete sequence of the L. intracellularis YtfN gene was determined from genomic DNA and is set forth herein as SEQ ID NO: 17. Based upon the 2,035 bp sequence obtained for the amino terminal portion of the ytfN gene fragment, oligonucleotide primer KWK-Li-YtfN-4C (SEQ ID NO:29) was designed and synthesized (Life Technologies; Rockville, Md.). This oligonucleotide binds within the 3'-region of the YtfN gene in the *L. intracellularis* chromosome to allow amplification of DNA downstream of the existing gene fragment. For polymerase chain amplification, primer KWK-Li-YtfN-4C (SEQ ID NO:29) was used in combination with a Vectorette™ specific oligonucleotide primer (ER70; SEQ ID NO:108) in 50 µl reactions containing 1×PCR Buffer II (Perkin Elmer; Foster City, Calif.), 2.0 mM MgCl$_2$, 250 µM each deoxy-NTP, 50 pMol each primer, and 2.5 U AmpliTaq™ Gold (Perkin Elmer) thermostable polymerase. Reactions were performed with 1 µl of the Vectorette™ libraries as DNA template. Amplification was carried out as follows: denaturation (94° C., 9 min); 40 cycles of denaturation (94° C., 30 sec), annealing (60° C., 30 sec), and polymerization (72° C., 4.0 min); this was followed by a final extension at 72° C. for 7 minutes.

The amplified products were visualized by separation on a 1.0% agarose gel (Sigma; St. Louis, Mo.). Screening of the HpaI library by PCR resulted in amplification of a fragment approximately 1.5 kb in length. The PCR product was purified using a QIAquick™ PCR Purification kit (Qiagen; Valencia, Calif.) and cloned into the TA cloning site of pCR2.1-TOPO (Invitrogen; Carlsbad, Calif.); the ligated product was transformed into Max Efficiency *E. coli* DH5α cells (Life Technologies; Rockville, Md.). Sequence analysis of the cloned fragment failed to identify a termination codon for ytfN. Therefore, oligonucleotide primer KWK-Li-YtfN-12C (SEQ ID NO:21) was designed and synthesized to be used in a second round of PCR amplification using the Vectorette™ libraries. The above-mentioned conditions for amplification were used, and products were visualized by agarose gel electrophoresis. A fragment approximately 1.6 kb in length was amplified from the DraI library. The PCR product was purified using a QIAquick PCR Purification kit, cloned into pCR2.1-TOPO, and subsequently transformed into Max Efficiency *E. coli* DH5α cells. Sequence analysis of the fragment identified a terminal TAA codon indicating the end of the ytfN gene.

ii) Determination of Genomic Sequence of Complete ytfN Gene

Results from the preliminary sequencing described above were used to design oligonucleotide primers for the specific amplification of two overlapping ytfN gene fragments directly from *L. intracellularis* chromosomal DNA. These products encompass the entire ytfN gene and were sequenced directly in an attempt to avoid introduction of sequence artifacts due to mutations which might arise during PCR amplification and subsequent cloning steps. To obtain the first of the two fragments, PCR amplifications were carried out in triplicate and contained 100 pMol of primers YtfN-D (SEQ. ID NO:45) and YtfN-U (SEQ. ID NO:46), 100 ng purified chromosomal DNA, 1×PC2 buffer (Ab Peptides; St. Louis, Mo.), 200 µM each dNTP, 15 U KlenTaq1 (Ab Peptides) and 0.3 U cloned Pfu (Stratagene; La Jolla, Calif.) thermostable polymerases in a 100 µl final sample volume. Conditions for amplification consisted of denaturation (94° C., 9 min), followed by 40 cycles of denaturation (94° C., 30 sec), annealing (60° C., 30 sec), and polymerization (72° C., 4.0 min), and a final extension at 72° C. for 7 min. To obtain the second (overlapping) fragment, PCR amplifications were carried out in triplicate as described above, except that primers KWK-Li-YtfN-12C (SEQ ID NO:21) and KWK-LI-YtfN-15N (SEQ ID NO:24) were used. Conditions for amplification consisted of denaturation (94° C., 9 min), followed by 40 cycles of denaturation (94° C., 30 sec), annealing (55° C., 30 sec), and polymerization (72° C., 2.5 min), and a final extension at 72° C. for 7 min.

Following amplification, each set of triplicate samples was pooled and the specific product from each was purified (QlAquick™ PCR Purification kit). Both purified DNA fragments were then subjected to direct sequence analysis using DyeDeoxy termination reactions on an ABI automated DNA sequencer (Lark Technologies Inc., Houston, Tex.). Synthetic oligonucleotide primers (SEQ ID NOs:21, 24, 26–38, 4346, 51–53, and 55–60) were used to sequence both DNA strands of the amplified products.

The ytfN ORF extends from nucleotides 1–4149 of SEQ ID NO:17 and encodes a 1382 amino acid protein (SEQ ID NO:18), having a theoretical molecular weight of 150,887 Daltons. The sequence of the amino terminus of the encoded protein resembles a prokaryotic signal sequence (von Heijne, 1985; Nielsen, et al., 1997), although the precise site of cleavage is not presently known. The ytfN ORF was compared against existing nucleotide and protein databases using the Basic Local Alignment Search Tool (BLAST) programs (Altschul, et al., 1990). The entry with which it shared the greatest homology was a hypothetical 40.5 kDa protein from *Zymomonas mobilis*. The second-most-significant homologous sequence identified was a YtfN homolog from *Neisseria meningitidis*.

iii) Cloning of Recombinant ytfM Gene into Expression Vectors

For the purpose of recombinant protein expression, both the ytfM and ytfN genes or fragments thereof were cloned without the sequences encoding their respective signal peptides.

The ytfM gene was amplified from *L. intracellularis* chromosomal DNA using oligonucleotide primers RA202-b (SEQ ID NO: 50) and RA201-b (SEQ ID NO: 49). For polymerase chain amplification, triplicate 50 µl reactions were set up with Eachcontaining 100 ng of chromosomal DNA as template, 1×PC2 buffer, 200 µM each dNTP, 50 pMol each primer, 7.5 U KlenTaq1 and 0.15 U cloned Pfu thermostable polymerases. Amplification was carried out as follows: denaturation (94° C., 9 min); 40 cycles of denaturation (94° C., 30 sec), annealing (60° C., 30 sec), and polymerization (72° C., 2.5 min), followed by a final extension at 72° C. for 7 minutes. Following amplification, the samples were purified (QlAquick™ PCR Purification kit) and pooled. The purified PCR product was cloned directly into the TA cloning site of both pBAD-TOPO and pBAD/Thio-TOPO (Invitrogen). The ligated products were transformed into Max Efficiency *E. coli* DH5α cells. The predicted amino terminal sequence of the encoded protein expressed from pBAD-TOPO:YtfM would consist of the vector-encoded sequence MGSGSGDDDDKLALLTM (SEQ ID NO: 61) followed immediately by the sequence ATSITTS (SEQ ID NO: 62) beginning at Alanine-24 of the YtfM ORF (SEQ ID NO:16). A clone containing the appropriate plasmid was identified, and purified plasmid was isolated from a small-scale broth culture using a QIAprep Spin Miniprep kit (Qiagen). This plasmid was transformed into *E. coli* BL21 (Novagen; Madison, Wis.) and BL21-CodonPlus-RIL cells (Stratagene); a clone was identified in each strain that contained the appropriate plasmid.

The predicted amino terminal sequence of the encoded fusion protein expressed from pBAD/Thio-TOPO:YtfM would consist of the thioredoxin protein and a 15 amino acid residue linker followed immediately by the sequence ATSITTS (SEQ ID NO: 62) beginning at Alanine-24 of the YtfM ORF (SEQ ID NO:16). A clone containing the appropriate plasmid was identified, and purified plasmid was isolated from a small-scale broth culture using a QIAprep Spin Miniprep kit. This plasmid was transformed into E. coli BL21 and BL21-CodonPlus-RIL cells; a clone was identified in each strain that contained the appropriate plasmid.

For cloning into pET-30a, the purified PCR product encoding YtfM was digested with BamHI and NcoI, then purified using a QIAquick™ PCR Purification kit. pET-30a was also digested with BamHI and NcoI; the linearized plasmid was purified using a JETsorb™ kit (Genomed; Frederick, Md.) prior to ligation. The ligated product was transformed into Max Efficiency E. coli DH5α cells. The predicted amino terminal sequence of the encoded fusion protein expressed from pET-30a:YtfM would consist of MHHHHHHSSGLVPRGSGMKETAAAKFER-QHMDSPDLGTDDDDKAM (SEQ ID NO: 63) encoded by the vector, followed by the sequence ATSITTS (SEQ ID NO: 62) beginning at Alanine-24 of the YtfM ORF (SEQ ID NO:16). A clone containing the appropriate plasmid was identified, and purified plasmid was isolated from a small-scale broth culture using a QIAprep Spin Miniprep kit. This plasmid was transformed into E. coli BL21 (DE3) (Novagen) and BL21-CodonPlus(DE3)-RIL cells (Stratagene); a clone was identified in each strain that contained the appropriate plasmid.

The ytfM gene was also amplified from L. intracellularis chromosomal DNA by PCR amplification using oligonucleotide primers RA200 (SEQ ID NO: 47) and RA201 (SEQ ID NO: 48). Duplicate 50 µl reactions were set up each containing 100 ng of chromosomal DNA as template, 1×PC2 buffer, 200 µM each dNTP, 50 pMol each primer, 7.5 U KlenTaq1 and 0.15 U cloned Pfu thermostable polymerases. Amplification was carried out as follows: denaturation (94° C., 9 min); 30 cycles of denaturation (94° C., 30 sec), annealing (60° C., 30 sec), and polymerization (72° C., 2 min), followed by a final extension at 72° C., for 7 minutes. Following amplification, the samples were purified (QIAquick™ PCR Purification kit) and pooled. The purified PCR product was cloned directly into the TA cloning site of pCR2.1-TOPO. The ligated product was transformed into Max Efficiency E. coli DH5α cells. A clone containing the appropriate plasmid was identified, propagated, and plasmid DNA was isolated using a QIAprep Spin Miniprep kit. Following digestion of the plasmid with EcoRI, a fragment corresponding to bp 437 of SEQ ID NO:15 to the EcoRI site in the MCS of pCR2.1-TOPO was purified using a JETsorb™ kit. pET-30a was also digested with EcoRI, and purified using a QIAquick PCR™ Purification kit. The two fragments were ligated and transformed into Max Efficiency E. coli DH5a cells. The predicted amino terminal sequence of the encoded fusion protein would consist of MHHHH-HHSSGLVPRGSGMKETMAKFERQHMDSP-DLGTDDDDKAMADIGS (SEQ ID NO: 64) encoded by the vector followed by the sequence EFNLSKG (SEQ ID NO: 65) beginning at Aspartate-146 of the YtfM ORF (SEQ ID NO:16). A clone containing the plasmid with the gene fragment inserted in the proper orientation was identified, and purified plasmid was isolated from a small-scale broth culture using a QIAprep Spin Miniprep kit. This plasmid was transformed into E. coli BL21-CodonPlus(DE3)-RIL cells; a clone was identified that contained the appropriate plasmid.

iv) Cloning of Recombinant ytfN Gene into Expression Vectors

The 5' half of the ytfN gene, excluding that encoding the signal sequence, was amplified from L. intracellularis chromosomal DNA using oligonucleotide primers RA205-b (SEQ ID NO: 53) and RA204-b (SEQ ID NO: 52). For polymerase chain amplification, triplicate 100 µl reactions were set up each containing 100 ng of chromosomal DNA as template, 1×PC2 buffer, 200 µM each dNTP, 100 pMol each primer, 15 U KlenTaq1 and 0.3 U cloned Pfu thermostable polymerases. Amplification was carried out as follows: denaturation (94° C., 9 min); 40 cycles of denaturation (94° C., 30 sec), annealing (60° C., 30 sec), and polymerization (72° C., 4 min), followed by a final extension at 72° C. for 7 minutes. Following amplification, the samples were purified (QIAquick™ PCR Purification kit) and pooled. The purified PCR product was cloned directly into the TA cloning site of both pBAD-TOPO and pBAD/Thio-TOPO (Invitrogen). The ligated products were transformed into Max Efficiency E. coli DH5α cells. The predicted amino terminal sequence of the encoded protein expressed from pBAD-TOPO:YtfN would consist of the vector-encoded sequence MGSGSGDDDDKLALGHM (SEQ ID NO: 66) followed immediately by the sequence RTSTGIA (SEQ ID NO: 67) beginning at Arginine-33 of the YtfN ORF (SEQ ID NO:18). A clone containing the appropriate plasmid was identified, and purified plasmid was isolated from a small-scale broth culture using a QIAprep Spin Miniprep kit. This plasmid was transformed into E. coli BL21-CodonPlus-RIL cells; a clone was identified that contained the appropriate plasmid.

The predicted amino terminal sequence of the encoded protein expressed from pBAD/Thio-TOPO:YffN would consist of the thioredoxin protein and a 15 amino acid linker followed immediately by the sequence RTSTGIA (SEQ ID NO: 67) beginning at Arginine-33 of the YtfN ORF (SEQ ID NO:18). A clone containing the appropriate plasmid was identified, and purified plasmid was isolated from a small-scale broth culture using a QIAprep Spin Miniprep kit. This plasmid was transformed into E. coli BL21-CodonPlus-RIL cells; a clone was identified that contained the appropriate plasmid.

For cloning into pET-30a, the purified PCR product was digested with BamHI and NdeI and extracted using a QIAquick PCR Purification kit. The linearized plasmid was purified using a JETsorb™ kit prior to ligation. The ligated product was transformed into Max Efficiency E. coli DH5α cells. The predicted amino terminal sequence of the protein expressed from pET-30a:YtfN would consist of Met encoded by RA205-b (SEQ ID NO: 53) followed by the sequence RTSTGIA (SEQ ID NO: 67) beginning at Arginine-33 of the YtfN ORF (SEQ ID NO:18). A clone containing the appropriate plasmid was identified, and purified plasmid was isolated from a small-scale broth culture using a QIAprep Spin Miniprep kit. This plasmid was transformed into E. coli BL21-CodonPlus(DE3)-RIL and BL21-CodonPlus(DE3)-RP cells (Stratagene); a clone was identified in each strain that contained the appropriate plasmid.

Utilizing oligonucleotide primers RA205-b (SEQ ID NO: 53) and KWK-Li-YffN-BgIII-3' (SEQ ID NO:39), an approximate 1 kb fragment encoding the N-terminal portion of YtfN, excluding the signal sequence, was amplified by PCR. Triplicate 50 µl reactions were set up each containing 100 ng of chromosomal DNA as template, 1×PC2 buffer, 200 µM each dNTP, 50 pMol each primer, 7.5 U KlenTaq1 and 0.15 U cloned Pfu thermostable polymerases. Amplification was carried out as follows: denaturation (94° C., 9 min); 40 cycles of denaturation (94° C., 30 sec), annealing (55° C., 30 sec), and polymerization (72° C., 1 min); followed by a final extension at 72° C. for 7 minutes. Following amplification, the samples were purified (QIAquick™ PCR Purification kit) and pooled. The purified PCR product was cloned directly into the TA cloning site of both pBAD-TOPO and pBAD/Thio-TOPO. The ligated products were transformed into Max Efficiency *E. coli* DH5α cells. The predicted amino terminal sequence of the protein expressed from pBAD-TOPO would consist of the vector-encoded sequence MGSGSGDDDDKLALGHM (SEQ ID NO: 66) followed immediately by the sequence RTSTGIA (SEQ ID NO: 67) beginning at Arginine-33 of the YtfN ORF (SEQ ID NO:18); the protein would terminate with Isoleucine-332 of ytfN (SEQ ID NO:18). A clone containing the appropriate plasmid was identified, and purified plasmid was isolated from a small-scale broth culture using a QIAprep Spin Miniprep kit. This plasmid was transformed into *E. coli* BL21-CodonPlus-RIL cells; a clone was identified that contained the appropriate plasmid.

The predicted amino terminal sequence of the encoded fusion protein expressed from pBAD/Thio-TOPO:YtfN would consist of the thioredoxin protein and a 15 amino acid linker followed immediately by the sequence RTSTGIA (SEQ ID NO: 67) beginning at Arginine-33 of the YtfN ORF (SEQ ID NO:18); again, the polypeptide would terminate with lsoleucine-332 of ytfN (SEQ ID NO:18). A clone containing the appropriate plasmid was identified, and purified plasmid was isolated from a small-scale broth culture using a QIAprep Spin Miniprep kit. This plasmid was transformed into *E. coli* BL21-CodonPlus-RIL cells; a clone was identified that contained the appropriate plasmid.

In order to generate a construct consisting of the above-described 1 kb (5' to Bg/II site) ytfN fragment in pET30a, the plasmid pET-30a:YtfN containing the 5' half of ytfN amplified using RA205-b (SEQ ID NO: 53) and RA204-b (SEQ ID NO: 52) was digested with Bg/II and BamHI, thus excising the gene sequence downstream of the Bg/II site within ytfN. The fragment containing the vector and ytfN sequence up to the Bg/II site was purified using a JETsorb m kit, and the remaining fragment was religated and transformed into *E. coli* Max Efficiency DH5α cells. The predicted amino terminal sequence of the protein expressed would consist of Met encoded by RA205-b (SEQ ID NO: 53) followed by the sequence RTSTGIA (SEQ ID NO: 67) beginning at Arginine-33 of the YtfN ORF (SEQ ID NO: 18). The polypeptide would terminate with lsoleucine-332 of SEQ ID NO:18, followed by a C-terminal extension consisting of DPNSSSVDKLAAALEHHHHHH (SEQ ID NO: 68) encoded by the vector. A clone containing the appropriate plasmid was identified, and purified plasmid was isolated from a small-scale broth culture using a QIAprep Spin Miniprep kit (Qiagen). This plasmid was transformed into *E. coli* BL21(DE3) and BL21-CodonPlus(DE3)-RIL cells; a clone was identified in each strain that contained the appropriate plasmid. Stocks of the clone containing this plasmid in *E. coli* BL21 (DE3) were frozen at −80° C.

v) Expression of Recombinant YtfN Polypeptide

Frozen working stock of the *E. coli* BL21 (DE3) transformant harboring pET-30a containing the 5' portion of ytfN up to the Bg/II site (eg. corresponding to amino acids 33–332 of the encoded YtfN protein) was thawed and seeded at a 1:5000 dilution in RWLDM/G vi defined medium [$K_2HPO_4$ (6 g/L), $KH_2PO_4$ (3 g/L), $(NH_4)_2SO_4$ (5 g/L), NaCl (2 g/L), 0.2 mL $CaCl_2$ (15 g/L), 0.4 mL $FeCl_3.6H_2O$ (5 g/L), 0.4 ml $MgSO_4.7H_2O$ (480 g/L), $ZnCl_2$ (6.5 g/L), $MnSO_4.H_2O$ (12 g/L), $Na_2MoO_4.2H_2O$ (5 g/L), $CuSO_4$ (1.5 g/L), $CoCl_2.6H_2O$ (2 g/L), $H_3BO_3$ (0.5 g/L), and 37% HCl (5 ml/L)]. Kanamycin was also added to a concentration of 25 μg/ml to maintain the expression plasmid. The culture was grown under fed-batch (50% glycerol) in a 5 liter working volume BioFlow 3000 fermentor (New Brunswick Scientific; Edison, N.J.) at 37° C. until $A_{625}$ was 2.9. At this time, IPTG was added to 0.1 mM, and culture samples were collected at 0, 2.25, and 3 hours post induction to monitor expression of recombinant YtfN (see Figure). The primary culture was maintained 28 hours post inoculation then immediately chilled, and wet cells were collected by centrifugation and stored at −20° C. Data showing expression of ytfN protein are presented in FIG. 1.

References

1. Altuvia, Y., Schueler, O., and Margalit, H. (1995) *J. Mol. Biol.* 249:244–250.
2. Amann and Brosius (1985). *Gene* 40: 183.
3. Anderson, B. J., M. M. Bills, J. R. Egerton, and J. S. Mattick. (1984) *Journal of Bacteriology* 160:748–754.
4. Altschul, S. F., Gish, W., Miller, W., Myers, E. W., Lipman, D. J., 1990, *J. Mol. Biol.* 215:403–410.
5. Ausubel, F. M., Brent, R., Kingston, R E, Moore, D. D., Seidman, J. G., Smith, J. A., and Struhl, K. (1987). In: Current Protocols in Molecular Biology. Wiley Interscience (ISBN 047150338).
6. Barker, I. K. and Van Dreumel, A. A. (1985) In □Pathology of Domestic Animals,□ 3rd Edition, Vol. 2 p. 1–237, eds K. V. F. Jubb, P. C. Kennedy and N. Palmer. (Academic Press: Orlando).
7. Cole et al. (1985) In: Monoclonal antibodies in cancer therapy, Alan R. Bliss Inc., pp 77–96.
8. Dayhof, M. D. (1978) In: *Nat. Biomed. Res. Found.* Washington D.C. Vol5, Suppl. 3.
9. De Groot, A. S., Carter, E. J., Roberts, C. G. P., Edelson, B. T., Jesdale, B. M., Meister, G. E., Houghten, R. A., Montoya, J., Romulo, R. C., Berzofsky, J. A., and Ramirezm, B. D. L. L. (1995) *Vaccines* 96, Cold Spring Harbor Laboratory, Cold Spring Harbor N.Y.
10. Devereux, J., Haeberli, P. and Smithies, O. (1984). *Nucl. Acids Res.* 12: 387–395.
11. Elwell, M R, Chapman, A L and Frenkel, J K (1981) *Veterinary Pathology* 18: 136–139.
12. Fox, J G, Murphy, J C, Otto, G Pecquet-Goad, M E, Larson, Q H K and Scott J A (1989) *Veterinary Pathology* 26: 515–517.
13. Gabriel, E. Meister, G. E., Caroline, G. P., Roberts, C. G. P., Berzofsky, J. A., and De Groot, A. S. (1995) *Vaccines* 95, Cold Spring Harbor Laboratory, Cold Spring Harbor N.Y.
14. Gebhart, C. J., Ward, G. E., Chang, K. And Kurtz, H. J. (1983). *American Journal of Veterinary Research* 44:361–367.
15. Gish, W and States, D. J. (1993) *Nature Genetics* 3: 266–272.
16. Goodman et al. (1987) *Biopolymers* 26: 525–532.
17. Huse et al. (1989) *Science* 246: 1275–1281.
18. Jones, L. A., Nibbelink, S., and Glock, R. D. (1997) *Am. J. Vet. Res.* 58:1125–1131.
19. Jonsson, L. and Martinsson, K. (1976) *Acta Veterinaria Scandinavica* 17:223–232.
20. Kohler and Milstein (1975) *Nature* 256: 495–499
21. Kozbor et al. (1983) *Immunol. Today* 4:72.
22. Lawson, G. H. K., McOrist, S., Jansi, S. and Mackie, R. A. (1993) *Journal of Clinical Microbiology* 31:1136–1142.
23. Love, R. J. and Love, D. M. (1977) *Veterinary Record* 100:473

24. Margalit, H., Spouge, J. L., Cornette, J. L., Cease, K. B., DeLisi, C., and Berzofsky, J. A. (1987) *J. Immunol.* 138:2213–2229.
25. Mason, R W, Monkton, P and Hasse D (1998) *Australian Veterinary Journal* (submitted for publication).
26. McOrist, S., Boid, R., Lawson, G. H. K. and McConnell, I. (1987) *The Veterinary Record* 121:421–422.
27. McOrist, S, Jasni, S, Mackie, R A, Macintyre, N, Neef, N. and Lawson G H K (1993) *Infection and Immmunity* 61: 4286–4292.
28. McOrist, S et al (1995) *International Journal of Systematic Bacteriology* 45: 820–825.
29. McPherson, M. J., Quirke, P., and Taylor, G. R. (1991) In: PCR: A Practical Approach. (series editors, D. Rickwood and B. D. Hames) IRL Press Limited, Oxford. pp1–253.
30. Meister, G. E., Roberts, C. G. P., Berzofsky, J. A., and De Groot, A. S. (1995) *Vaccine* 13: 581–591.
31. Mierke et al. (1990) *Int. J. Peptide Protein Research* 35:35–45.
32. Mohapatra, S. S., Cao, Y., Ni, H., and Salo, D. (1995) *Allergy* 50:37–44.
33. Needleman and Wunsch (1970) *J. Mol. Biol.* 48:443–453.
34. Nielsen, H., Engelbrecht, J., Brunak, S., and von Heijne, G., (1997) *Protein Engineering*, 10: 1–6
35. Nollau, P., Moser, C. and C. Wagener (1996) *Bio Techniques* 20:784–788.
36. O'Neil, I. P. A. (1970) *Veterinary Record* 87:742–747.
37. Parker, K. C., Bednarek, M. A., and Coligan, J. E. (1994) *J. Immunol.* 152:163–175.
38. Portoghese et al. (1990) *J. Med. Chem.* 33:1714–1720.
39. Reinhartz, A., Alajem, S., Samson, A. and Herzberg, M.(1993). *Gene* 136: 221–226.
40. Rowland, A. C. and Lawson, G. H. K. (1976) *Veterinary Record* 97:178–180.
41. Sambrook, J., E. F. Fritsch, and T. Maniatis. (1989) Molecular cloning. A laboratory manual. Second edition. Cold Spring Harbour Laboratory, Cold Spring Harbour, N.Y.
42. Schodeb, T R and Fox J G (1990) *Veterinary Pathology* 27: 73–80.
43. Shimatake and Rosenberg (1981) *Nature* 292:128.
44. Stills, H. F. (1991). *Infection and immunology* 59:3227–3236.
45. Straw, B. E. (1990). *Journal of American Veterinary Medical Association* 197:355–357.
46. Studier and Moffat (1986) *J. Mol. Biol.* 189: 113.
47. Thompson, J. D., Higgins, D. G., and Gibson, T. J. (1994) *Nucl. Acids Res.* 22: 4673–4680.
48. Vajda, S. and DeLisi, C. (1990) *Biopolymers* 29:1755–1772.
49. van Regenmortel, M. (1992) Molecular dissection of protein antigens. In: Structure of antigens, (van Regenmortel M. ed.) CRC Press, London, pp1–27.
50. von Heijne, (1985), *J. Mol. Biol.* 184: 99–105.

What is claimed is:

1. An isolated polynucleotide sequence as set forth in SEQ ID No: 1 that encodes a *Lawsonia intracelluaris* flhB polypeptide.

2. A plasmid of pGTE#2 flhB AGAL Accession No. NM00/16477.

3. A recombinant vector capable of replication in a host cell, wherein said vector comprises the isolated polynucleotide sequence as set forth in claim 1.

4. A host cell comprising the recombinant vector of claim 3.

5. The host cell of claim 4 wherein said host cell is a bacterium.

* * * * *

SEQUENCE LISTING

```
<160> NUMBER OF SEQ ID NOS: 68

<210> SEQ ID NO 1
<211> LENGTH: 622
<212> TYPE: DNA
<213> ORGANISM: Lawsonia intracellularis
<220> FEATURE:
<221> NAME/KEY: CDS
<222> LOCATION: (1)...(621)

<400> SEQUENCE: 1 atg tct gat gat ccc agt aaa aca gag aaa gca acc ccg aaa cga cgt        48
Met Ser Asp Asp Pro Ser Lys Thr Glu Lys Ala Thr Pro Lys Arg Arg
1               5                   10                  15 cag gaa gct cgt tct gaa ggg agt gtc cct aaa tca gaa gag gtt act        96
Gln Glu Ala Arg Ser Glu Gly Ser Val Pro Lys Ser Glu Glu Val Thr
            20                  25                  30 aaa gca ttg act act gca gca ggg atg ctg ggg ctt gct att tat tca       144
Lys Ala Leu Thr Thr Ala Ala Gly Met Leu Gly Leu Ala Ile Tyr Ser
        35                  40                  45 ggc gta atg gga cgt cat ttt gaa aca att ttc tac tat att ttt aca       192
Gly Val Met Gly Arg His Phe Glu Thr Ile Phe Tyr Tyr Ile Phe Thr
    50                  55                  60 gaa tca ttt cgg ttt gag gtt aca gca cag tca gta tat gct tta ttt       240
Glu Ser Phe Arg Phe Glu Val Thr Ala Gln Ser Val Tyr Ala Leu Phe
65                  70                  75                  80 att tat gtt gct caa gag ata gct att tta ttg atg cca ata tta ctt       288
Ile Tyr Val Ala Gln Glu Ile Ala Ile Leu Leu Met Pro Ile Leu Leu
                85                  90                  95 ttt att gct gtt acg gca tgg att tca tta cgt gta caa gtt ggt gca       336
Phe Ile Ala Val Thr Ala Trp Ile Ser Leu Arg Val Gln Val Gly Ala
            100                 105                 110
```

```
tta tgg act aca aag gtt ttt aaa ttt aaa tgg agt aaa ttt aat ata    384
Leu Trp Thr Thr Lys Val Phe Lys Phe Lys Trp Ser Lys Phe Asn Ile
            115                 120                 125 ata aaa ggg ttg aaa gga atg ttt gct tct caa caa aca ctt gtt cga    432
Ile Lys Gly Leu Lys Gly Met Phe Ala Ser Gln Gln Thr Leu Val Arg
        130                 135                 140 ctt tta cgt agt tta gtt caa gta att gtt ata ggt att gtt cca tat    480
Leu Leu Arg Ser Leu Val Gln Val Ile Val Ile Gly Ile Val Pro Tyr
145                 150                 155                 160 atg att ata aaa gga gag ttt tca aac ttt tta cca tta tat tat gca    528
Met Ile Ile Lys Gly Glu Phe Ser Asn Phe Leu Pro Leu Tyr Tyr Ala
                165                 170                 175 agt cct tca ggt gtg gca gat tat atg ctt aat aca gga ata gta ctt    576
Ser Pro Ser Gly Val Ala Asp Tyr Met Leu Asn Thr Gly Ile Val Leu
            180                 185                 190 gtt tta tat acg cta att cct atg aca att att gca gtc gca gat       621
Val Leu Tyr Thr Leu Ile Pro Met Thr Ile Ile Ala Val Ala Asp
        195                 200                 205 c                                                                  622

<210> SEQ ID NO 2
<211> LENGTH: 207
<212> TYPE: PRT
<213> ORGANISM: Lawsonia intracellularis

<400> SEQUENCE: 2

Met Ser Asp Asp Pro Ser Lys Thr Glu Lys Ala Thr Pro Lys Arg Arg
 1               5                  10                  15

Gln Glu Ala Arg Ser Glu Gly Ser Val Pro Lys Ser Glu Glu Val Thr
            20                  25                  30

Lys Ala Leu Thr Thr Ala Ala Gly Met Leu Gly Leu Ala Ile Tyr Ser
        35                  40                  45

Gly Val Met Gly Arg His Phe Glu Thr Ile Phe Tyr Tyr Ile Phe Thr
    50                  55                  60

Glu Ser Phe Arg Phe Glu Val Thr Ala Gln Ser Val Tyr Ala Leu Phe
65                  70                  75                  80

Ile Tyr Val Ala Gln Glu Ile Ala Ile Leu Leu Met Pro Ile Leu Leu
                85                  90                  95

Phe Ile Ala Val Thr Ala Trp Ile Ser Leu Arg Val Gln Val Gly Ala
            100                 105                 110

Leu Trp Thr Thr Lys Val Phe Lys Phe Lys Trp Ser Lys Phe Asn Ile
        115                 120                 125

Ile Lys Gly Leu Lys Gly Met Phe Ala Ser Gln Gln Thr Leu Val Arg
    130                 135                 140

Leu Leu Arg Ser Leu Val Gln Val Ile Val Ile Gly Ile Val Pro Tyr
145                 150                 155                 160

Met Ile Ile Lys Gly Glu Phe Ser Asn Phe Leu Pro Leu Tyr Tyr Ala
                165                 170                 175

Ser Pro Ser Gly Val Ala Asp Tyr Met Leu Asn Thr Gly Ile Val Leu
            180                 185                 190

Val Leu Tyr Thr Leu Ile Pro Met Thr Ile Ile Ala Val Ala Asp
        195                 200                 205

<210> SEQ ID NO 3
<211> LENGTH: 789
<212> TYPE: DNA
<213> ORGANISM: Lawsonia intracellularis
<220> FEATURE:
```

```
-continued

<221> NAME/KEY: CDS
<222> LOCATION: (1)...(786)

<400> SEQUENCE: 3 atg aat tta ttt aat ttt gat cct agt atg ttt ctt agt ttt tta ctt      48
Met Asn Leu Phe Asn Phe Asp Pro Ser Met Phe Leu Ser Phe Leu Leu
 1               5                  10                  15 aca ttt tta cgt att agt gtt gtc tta ttt atg ctt cct ttt ttt tct      96
Thr Phe Leu Arg Ile Ser Val Val Leu Phe Met Leu Pro Phe Phe Ser
                20                  25                  30 att gat ggt ttt cct aat atg tta aaa gca tca ata gct ctt att cta     144
Ile Asp Gly Phe Pro Asn Met Leu Lys Ala Ser Ile Ala Leu Ile Leu
             35                  40                  45 act ata gtt ctt tgg ggg cgt ctt tct ctt tca gga aca caa atg cca     192
Thr Ile Val Leu Trp Gly Arg Leu Ser Leu Ser Gly Thr Gln Met Pro
         50                  55                  60 gcg cat cct ttc gat cta gta ttg tta atc ata agc gag gtt ttt ctt     240
Ala His Pro Phe Asp Leu Val Leu Leu Ile Ile Ser Glu Val Phe Leu
 65                  70                  75                  80 ggt att gta ttg ggg ctt gcg gta aac ttt ttc ttt gca gga att caa     288
Gly Ile Val Leu Gly Leu Ala Val Asn Phe Phe Phe Ala Gly Ile Gln
                 85                  90                  95 gct ggg gga gaa att ctt gct aca caa atg ggg ttt aca atg att acg     336
Ala Gly Gly Glu Ile Leu Ala Thr Gln Met Gly Phe Thr Met Ile Thr
            100                 105                 110 ctt gca gac cca tta act ggt aac acc aca ggt ttt att gca cat ttt     384
Leu Ala Asp Pro Leu Thr Gly Asn Thr Thr Gly Phe Ile Ala His Phe
        115                 120                 125 ctt tat atg gtt gct aca tta gtt ttt ctt gct ctt aat ggc cat ttg     432
Leu Tyr Met Val Ala Thr Leu Val Phe Leu Ala Leu Asn Gly His Leu
    130                 135                 140 ttt ctt ata aaa gct ttt aca tat act ttt aaa atg gtt cca gca gga     480
Phe Leu Ile Lys Ala Phe Thr Tyr Thr Phe Lys Met Val Pro Ala Gly
145                 150                 155                 160 gga ctt gtt gta aga gaa att tta ttg agt gaa ctt ctt aat atg gca     528
Gly Leu Val Val Arg Glu Ile Leu Leu Ser Glu Leu Leu Asn Met Ala
                165                 170                 175 ggg atg att ttt gtt ttt gcc tta cat gtt gcg gca cca gtt atg tca     576
Gly Met Ile Phe Val Phe Ala Leu His Val Ala Ala Pro Val Met Ser
            180                 185                 190 gct ctt ttt tta gta gag atc tct tta gga ctt atg gca aga gct gct     624
Ala Leu Phe Leu Val Glu Ile Ser Leu Gly Leu Met Ala Arg Ala Ala
        195                 200                 205 cct cag att cat att atg gaa gtt gga ttt cct gta aaa att ggt gta     672
Pro Gln Ile His Ile Met Glu Val Gly Phe Pro Val Lys Ile Gly Val
    210                 215                 220 gga ttt ttt ttc att gga cta tta ttt act atc tta tca aaa gaa acc     720
Gly Phe Phe Phe Ile Gly Leu Leu Phe Thr Ile Leu Ser Lys Glu Thr
225                 230                 235                 240 tat cga ttt att gca ggc cta gag gga cta ttt ttt aac tta ctt act     768
Tyr Arg Phe Ile Ala Gly Leu Glu Gly Leu Phe Phe Asn Leu Leu Thr
                245                 250                 255 gta atg ggt agt gga aaa tag                                         789
Val Met Gly Ser Gly Lys
            260

<210> SEQ ID NO 4
<211> LENGTH: 262
<212> TYPE: PRT
<213> ORGANISM: Lawsonia intracellularis
```

```
<400> SEQUENCE: 4

Met Asn Leu Phe Asn Phe Asp Pro Ser Met Phe Leu Ser Phe Leu Leu
1               5                   10                  15

Thr Phe Leu Arg Ile Ser Val Val Leu Phe Met Leu Pro Phe Phe Ser
                20                  25                  30

Ile Asp Gly Phe Pro Asn Met Leu Lys Ala Ser Ile Ala Leu Ile Leu
            35                  40                  45

Thr Ile Val Leu Trp Gly Arg Leu Ser Leu Ser Gly Thr Gln Met Pro
        50                  55                  60

Ala His Pro Phe Asp Leu Val Leu Leu Ile Ile Ser Glu Val Phe Leu
65                  70                  75                  80

Gly Ile Val Leu Gly Leu Ala Val Asn Phe Phe Ala Gly Ile Gln
                85                  90                  95

Ala Gly Gly Glu Ile Leu Ala Thr Gln Met Gly Phe Thr Met Ile Thr
                100                 105                 110

Leu Ala Asp Pro Leu Thr Gly Asn Thr Thr Gly Phe Ile Ala His Phe
                115                 120                 125

Leu Tyr Met Val Ala Thr Leu Val Phe Leu Ala Leu Asn Gly His Leu
        130                 135                 140

Phe Leu Ile Lys Ala Phe Thr Tyr Thr Phe Lys Met Val Pro Ala Gly
145                 150                 155                 160

Gly Leu Val Val Arg Glu Ile Leu Leu Ser Glu Leu Leu Asn Met Ala
                165                 170                 175

Gly Met Ile Phe Val Phe Ala Leu His Val Ala Ala Pro Val Met Ser
            180                 185                 190

Ala Leu Phe Leu Val Glu Ile Ser Leu Gly Leu Met Ala Arg Ala Ala
        195                 200                 205

Pro Gln Ile His Ile Met Glu Val Gly Phe Pro Val Lys Ile Gly Val
                210                 215                 220

Gly Phe Phe Phe Ile Gly Leu Leu Phe Thr Ile Leu Ser Lys Glu Thr
225                 230                 235                 240

Tyr Arg Phe Ile Ala Gly Leu Glu Gly Leu Phe Phe Asn Leu Leu Thr
                245                 250                 255

Val Met Gly Ser Gly Lys
                260

<210> SEQ ID NO 5
<211> LENGTH: 1371
<212> TYPE: DNA
<213> ORGANISM: Lawsonia intracellularis
<220> FEATURE:
<221> NAME/KEY: CDS
<222> LOCATION: (1)...(1368)

<400> SEQUENCE: 5 atg tca gca cgt ata ctt att ata gat gat gaa gac tct att aga ttt      48
Met Ser Ala Arg Ile Leu Ile Ile Asp Asp Glu Asp Ser Ile Arg Phe
1               5                   10                  15 tca ttg aaa gga att ttt gaa gat gag ggc cat gaa gtt tta gaa aga      96
Ser Leu Lys Gly Ile Phe Glu Asp Glu Gly His Glu Val Leu Glu Arg
                20                  25                  30 gct tca gca gaa gaa gga ctt aag tgt gtt gat gta gag tct cca gat     144
Ala Ser Ala Glu Glu Gly Leu Lys Cys Val Asp Val Glu Ser Pro Asp
            35                  40                  45 ctt gtt ttt ctt gat att tgg ctt cct ggg atg gat ggt ctt atg gct     192
Leu Val Phe Leu Asp Ile Trp Leu Pro Gly Met Asp Gly Leu Met Ala
        50                  55                  60
```

-continued

| | | |
|---|---|---|
| tta gac cat att cag gct ctt cat cag gaa tta cct gtt att atg att<br>Leu Asp His Ile Gln Ala Leu His Gln Glu Leu Pro Val Ile Met Ile<br>65                        70                     75                   80 | 240 |
| tca ggt cat gcc aca att gaa act gct gta aca gct atc cgt caa ggt<br>Ser Gly His Ala Thr Ile Glu Thr Ala Val Thr Ala Ile Arg Gln Gly<br>                  85                   90                   95 | 288 |
| gct tat gat ttt att gaa aag cct ctt tct ttg gaa aaa gtc ctt att<br>Ala Tyr Asp Phe Ile Glu Lys Pro Leu Ser Leu Glu Lys Val Leu Ile<br>              100                 105               110 | 336 |
| aca gct aat aga gct ata gaa aca gta aga tta aga agg gaa aac aaa<br>Thr Ala Asn Arg Ala Ile Glu Thr Val Arg Leu Arg Arg Glu Asn Lys<br>            115                120               125 | 384 |
| tta cta cgt act gta tta cct gag gag agt gag ttt ata gga cag tct<br>Leu Leu Arg Thr Val Leu Pro Glu Glu Ser Glu Phe Ile Gly Gln Ser<br>130                       135               140 | 432 |
| cct gtt atc tta aaa ttt aaa agt tta tta tca cag gtc gct cca aca<br>Pro Val Ile Leu Lys Phe Lys Ser Leu Leu Ser Gln Val Ala Pro Thr<br>145                     150               155               160 | 480 |
| gat gct tgg gta cta ctt aca gga gag aat ggt aca ggt aaa gag tta<br>Asp Ala Trp Val Leu Leu Thr Gly Glu Asn Gly Thr Gly Lys Glu Leu<br>                  165               170              175 | 528 |
| gct gca caa gca ttg cac aaa gga agc tca cga tat caa aaa cca ttt<br>Ala Ala Gln Ala Leu His Lys Gly Ser Ser Arg Tyr Gln Lys Pro Phe<br>            180                185               190 | 576 |
| ata gct gtt aat tgt gct gct atc cct gaa gaa ttg att gaa agc gaa<br>Ile Ala Val Asn Cys Ala Ala Ile Pro Glu Glu Leu Ile Glu Ser Glu<br>            195                200               205 | 624 |
| cta ttt ggt cat gaa aaa ggg gcc ttt act ggt gcc gat gct tct cgt<br>Leu Phe Gly His Glu Lys Gly Ala Phe Thr Gly Ala Asp Ala Ser Arg<br>210                       215               220 | 672 |
| gca ggt cgt ttt gag ttg gca cat aaa gga aca tta ttt ctt gat gaa<br>Ala Gly Arg Phe Glu Leu Ala His Lys Gly Thr Leu Phe Leu Asp Glu<br>225                     230               235               240 | 720 |
| ata gga gat atg agt tta aaa aca caa gca aaa att ttg cgt att ttg<br>Ile Gly Asp Met Ser Leu Lys Thr Gln Ala Lys Ile Leu Arg Ile Leu<br>                  245               250              255 | 768 |
| caa gaa caa tgt ttt gaa aaa att ggt agt gtt aga act att aaa gtt<br>Gln Glu Gln Cys Phe Glu Lys Ile Gly Ser Val Arg Thr Ile Lys Val<br>            260                265               270 | 816 |
| gat gta aga gtt att gca gca aca aat aag aat ctt gaa gac gct att<br>Asp Val Arg Val Ile Ala Ala Thr Asn Lys Asn Leu Glu Asp Ala Ile<br>            275                280               285 | 864 |
| agc gat gga aca ttt cgt caa gat ttg tat tat cgc tta cga gtt gtt<br>Ser Asp Gly Thr Phe Arg Gln Asp Leu Tyr Tyr Arg Leu Arg Val Val<br>290                       295               300 | 912 |
| cca ttg cat ctt ccc cct ctt cgt gaa cgt gat tct gat att gag cta<br>Pro Leu His Leu Pro Pro Leu Arg Glu Arg Asp Ser Asp Ile Glu Leu<br>305                     310               315               320 | 960 |
| tta tta aat agg ttt gtg att cag ttg agt aaa cgt tat aga cgt gag<br>Leu Leu Asn Arg Phe Val Ile Gln Leu Ser Lys Arg Tyr Arg Arg Glu<br>                  325               330              335 | 1008 |
| ccg cct att ttt tta gat gag gtc ttc cct gta ttg aaa caa tat tgt<br>Pro Pro Ile Phe Leu Asp Glu Val Phe Pro Val Leu Lys Gln Tyr Cys<br>            340                345               350 | 1056 |
| tgg cca ggg aat gta aga gaa tta ctt aat ttt gta gaa cga atg gtt<br>Trp Pro Gly Asn Val Arg Glu Leu Leu Asn Phe Val Glu Arg Met Val<br>            355                360               365 | 1104 |
| att ctt tat tca ggg aag aaa gta tgt ttg aca gat cct aag gta aaa<br>Ile Leu Tyr Ser Gly Lys Lys Val Cys Leu Thr Asp Pro Lys Val Lys | 1152 |

-continued

```
                  370                 375                 380
agc aat tta aaa tat tta ccc aag aaa ttt tct tcc cat tat aac ttt       1200
Ser Asn Leu Lys Tyr Leu Pro Lys Lys Phe Ser His Tyr Asn Phe
385                 390                 395                 400 ctt ccc gat ata gat ttt aac cag gct aaa ata gct ttt gaa cca aaa       1248
Leu Pro Asp Ile Asp Phe Asn Gln Ala Lys Ile Ala Phe Glu Pro Lys
                    405                 410                 415 ttt tta act gaa aaa tta cat gct tat caa gga aat att acc cga tta       1296
Phe Leu Thr Glu Lys Leu His Ala Tyr Gln Gly Asn Ile Thr Arg Leu
                420                 425                 430 gca gaa gct att gga ctt gaa aga agt tat tta tat aga aag cta aaa       1344
Ala Glu Ala Ile Gly Leu Glu Arg Ser Tyr Leu Tyr Arg Lys Leu Lys
            435                 440                 445 agc tat ggt att tat ctg tct gag tga                                   1371
Ser Tyr Gly Ile Tyr Leu Ser Glu
        450                 455
```

<210> SEQ ID NO 6
<211> LENGTH: 456
<212> TYPE: PRT
<213> ORGANISM: Lawsonia intracellularis

<400> SEQUENCE: 6

```
Met Ser Ala Arg Ile Leu Ile Asp Asp Glu Asp Ser Ile Arg Phe
 1               5                  10                  15

Ser Leu Lys Gly Ile Phe Glu Asp Glu Gly His Glu Val Leu Glu Arg
                20                  25                  30

Ala Ser Ala Glu Glu Gly Leu Lys Cys Val Asp Val Glu Ser Pro Asp
            35                  40                  45

Leu Val Phe Leu Asp Ile Trp Leu Pro Gly Met Asp Gly Leu Met Ala
        50                  55                  60

Leu Asp His Ile Gln Ala Leu His Gln Glu Leu Pro Val Ile Met Ile
65                  70                  75                  80

Ser Gly His Ala Thr Ile Glu Thr Ala Val Thr Ala Ile Arg Gln Gly
                85                  90                  95

Ala Tyr Asp Phe Ile Glu Lys Pro Leu Ser Leu Glu Lys Val Leu Ile
            100                 105                 110

Thr Ala Asn Arg Ala Ile Glu Thr Val Arg Leu Arg Arg Glu Asn Lys
        115                 120                 125

Leu Leu Arg Thr Val Leu Pro Glu Glu Ser Glu Phe Ile Gly Gln Ser
130                 135                 140

Pro Val Ile Leu Lys Phe Lys Ser Leu Leu Ser Gln Val Ala Pro Thr
145                 150                 155                 160

Asp Ala Trp Val Leu Leu Thr Gly Glu Asn Gly Thr Gly Lys Glu Leu
                165                 170                 175

Ala Ala Gln Ala Leu His Lys Gly Ser Ser Arg Tyr Gln Lys Pro Phe
            180                 185                 190

Ile Ala Val Asn Cys Ala Ala Ile Pro Glu Glu Leu Ile Glu Ser Glu
        195                 200                 205

Leu Phe Gly His Glu Lys Gly Ala Phe Thr Gly Ala Asp Ala Ser Arg
    210                 215                 220

Ala Gly Arg Phe Glu Leu Ala His Lys Gly Thr Leu Phe Leu Asp Glu
225                 230                 235                 240

Ile Gly Asp Met Ser Leu Lys Thr Gln Ala Lys Ile Leu Arg Ile Leu
                245                 250                 255

Gln Glu Gln Cys Phe Glu Lys Ile Gly Ser Val Arg Thr Ile Lys Val
```

-continued

```
                        260                 265                 270
Asp Val Arg Val Ile Ala Ala Thr Asn Lys Asn Leu Glu Asp Ala Ile
                275                 280                 285
Ser Asp Gly Thr Phe Arg Gln Asp Leu Tyr Tyr Arg Leu Arg Val Val
            290                 295                 300
Pro Leu His Leu Pro Leu Arg Glu Arg Asp Ser Asp Ile Glu Leu
305                 310                 315                 320
Leu Leu Asn Arg Phe Val Ile Gln Leu Ser Lys Arg Tyr Arg Glu
                325                 330                 335
Pro Pro Ile Phe Leu Asp Glu Val Phe Pro Val Leu Lys Gln Tyr Cys
            340                 345                 350
Trp Pro Gly Asn Val Arg Glu Leu Leu Asn Phe Val Glu Arg Met Val
                355                 360                 365
Ile Leu Tyr Ser Gly Lys Lys Val Cys Leu Thr Asp Pro Lys Val Lys
            370                 375                 380
Ser Asn Leu Lys Tyr Leu Pro Lys Lys Phe Ser Ser His Tyr Asn Phe
385                 390                 395                 400
Leu Pro Asp Ile Asp Phe Asn Gln Ala Lys Ile Ala Phe Glu Pro Lys
                405                 410                 415
Phe Leu Thr Glu Lys Leu His Ala Tyr Gln Gly Asn Ile Thr Arg Leu
            420                 425                 430
Ala Glu Ala Ile Gly Leu Glu Arg Ser Tyr Leu Tyr Arg Lys Leu Lys
            435                 440                 445
Ser Tyr Gly Ile Tyr Leu Ser Glu
450                 455
```

<210> SEQ ID NO 7
<211> LENGTH: 412
<212> TYPE: DNA
<213> ORGANISM: Lawsonia intracellularis
<220> FEATURE:
<221> NAME/KEY: CDS
<222> LOCATION: (1)...(411)

<400> SEQUENCE: 7

```
aaa caa att gat ata atc att agt ggg gct acg ata act ctt gaa cgt     48
Lys Gln Ile Asp Ile Ile Ile Ser Gly Ala Thr Ile Thr Leu Glu Arg
1               5                  10                  15 aat ctt caa gtc aat ttt tct aac cca tac cat caa aca gat att gaa     96
Asn Leu Gln Val Asn Phe Ser Asn Pro Tyr His Gln Thr Asp Ile Glu
                20                  25                  30 gtc ctg gct aat gca aaa aaa gtt aaa ggg atg aag ttt cca caa gac    144
Val Leu Ala Asn Ala Lys Lys Val Lys Gly Met Lys Phe Pro Gln Asp
            35                  40                  45 ttt aat aaa cct gaa gtt ata gtt gct ata cgt aat ggt agt aca gtt    192
Phe Asn Lys Pro Glu Val Ile Val Ala Ile Arg Asn Gly Ser Thr Val
        50                  55                  60 att act cct gca aag caa ctt ctt cct aaa gca tct ttt aga ctc ttt    240
Ile Thr Pro Ala Lys Gln Leu Leu Pro Lys Ala Ser Phe Arg Leu Phe
65                  70                  75                  80 gat gat gaa gtt gca tct ata aaa gat gta gaa tct gga caa tca cat    288
Asp Asp Glu Val Ala Ser Ile Lys Asp Val Glu Ser Gly Gln Ser His
                85                  90                  95 ata tta tta gct tca gca cca tta cca gcg att caa gct ata aac tca    336
Ile Leu Leu Ala Ser Ala Pro Leu Pro Ala Ile Gln Ala Ile Asn Ser
            100                 105                 110 aat ggc aac ctt att cgt tta gat aca ctc ccc att act cat caa tct    384
Asn Gly Asn Leu Ile Arg Leu Asp Thr Leu Pro Ile Thr His Gln Ser
```

```
                     115                 120                 125
gta gga ttt gca ata aag aag gga gat c                                        412
Val Gly Phe Ala Ile Lys Lys Gly Asp
    130                 135

<210> SEQ ID NO 8
<211> LENGTH: 137
<212> TYPE: PRT
<213> ORGANISM: Lawsonia intracellularis

<400> SEQUENCE: 8

Lys Gln Ile Asp Ile Ile Ser Gly Ala Thr Ile Thr Leu Glu Arg
 1               5                  10                  15

Asn Leu Gln Val Asn Phe Ser Asn Pro Tyr His Gln Thr Asp Ile Glu
            20                  25                  30

Val Leu Ala Asn Ala Lys Lys Val Lys Gly Met Lys Phe Pro Gln Asp
        35                  40                  45

Phe Asn Lys Pro Glu Val Ile Val Ala Ile Arg Asn Gly Ser Thr Val
50                  55                  60

Ile Thr Pro Ala Lys Gln Leu Leu Pro Lys Ala Ser Phe Arg Leu Phe
65                  70                  75                  80

Asp Asp Glu Val Ala Ser Ile Lys Asp Val Glu Ser Gly Gln Ser His
                85                  90                  95

Ile Leu Leu Ala Ser Ala Pro Leu Pro Ala Ile Gln Ala Ile Asn Ser
            100                 105                 110

Asn Gly Asn Leu Ile Arg Leu Asp Thr Leu Pro Ile Thr His Gln Ser
        115                 120                 125

Val Gly Phe Ala Ile Lys Lys Gly Asp
    130                 135

<210> SEQ ID NO 9
<211> LENGTH: 849
<212> TYPE: DNA
<213> ORGANISM: Lawsonia intracellularis
<220> FEATURE:
<221> NAME/KEY: CDS
<222> LOCATION: (1)...(846)

<400> SEQUENCE: 9 atg tat att att att g

-continued

| | | |
|---|---|---|
| tac cct aca att gta aaa gat act aaa gtt gtt gcc ttt att gca gat<br>Tyr Pro Thr Ile Val Lys Asp Thr Lys Val Val Ala Phe Ile Ala Asp<br>          115                    120                    125 | 384 |
| aca tta cga gtt tat ctg aca aca ggt gca cca gaa gat ata gat aac<br>Thr Leu Arg Val Tyr Leu Thr Thr Gly Ala Pro Glu Asp Ile Asp Asn<br>130                    135                    140 | 432 |
| ctc atg gaa tct gac atg aaa att aca cac gaa gaa gaa tta tta cct<br>Leu Met Glu Ser Asp Met Lys Ile Thr His Glu Glu Glu Leu Leu Pro<br>145                    150                    155                    160 | 480 |
| gca cat tcc atc agc cat atg gca gag tcg cta cca gga atg ggt att<br>Ala His Ser Ile Ser His Met Ala Glu Ser Leu Pro Gly Met Gly Ile<br>          165                    170                    175 | 528 |
| gtt gct gca gta tta ggt gtt gtt att acc atg gga aaa att aat gag<br>Val Ala Ala Val Leu Gly Val Val Ile Thr Met Gly Lys Ile Asn Glu<br>               180                    185                    190 | 576 |
| cct cca gaa gtc ctt ggg cat tat att gga gca gct ttg gtt ggt aca<br>Pro Pro Glu Val Leu Gly His Tyr Ile Gly Ala Ala Leu Val Gly Thr<br>          195                    200                    205 | 624 |
| ttt ata ggt att ctt ttc tgt tat ggt ttt ttt gga cct atg ggt tca<br>Phe Ile Gly Ile Leu Phe Cys Tyr Gly Phe Phe Gly Pro Met Gly Ser<br>210                    215                    220 | 672 |
| aag ctt gaa acc tct gca gaa gaa gca cat ttt tat tat aat tcc att<br>Lys Leu Glu Thr Ser Ala Glu Glu Ala His Phe Tyr Tyr Asn Ser Ile<br>225                    230                    235                    240 | 720 |
| aaa gaa gct gtt gca gct gct atc cga ggt tct aca cca atg ata gca<br>Lys Glu Ala Val Ala Ala Ala Ile Arg Gly Ser Thr Pro Met Ile Ala<br>               245                    250                    255 | 768 |
| gta gaa tat gga aga cgt gcc ata cct aat aca ttt cgt cca tca ttt<br>Val Glu Tyr Gly Arg Arg Ala Ile Pro Asn Thr Phe Arg Pro Ser Phe<br>          260                    265                    270 | 816 |
| tcg gaa atg gaa gaa cgt cta aaa aca gga taa<br>Ser Glu Met Glu Glu Arg Leu Lys Thr Gly<br>275                    280 | 849 |

<210> SEQ ID NO 10
<211> LENGTH: 282
<212> TYPE: PRT
<213> ORGANISM: Lawsonia intracellularis

<400> SEQUENCE: 10

Met Tyr Ile Ile Ile Gly Tyr Phe Ile Val Ile Ala Ser Ile Ile Gly
1               5                   10                  15

Gly Tyr Leu Met Ala Lys Gly Asn Leu Ala Leu Leu Phe Gln Pro Ala
            20                  25                  30

Glu Leu Val Ile Ile Gly Ala Ala Leu Gly Ala Phe Phe Ala Ser
        35                  40                  45

Gln Thr Lys Tyr Ser Phe Thr Leu Val Ile Lys Asn Leu Ser His Ile
    50                  55                  60

Phe Gly Asp Pro Asn Ser Thr Lys Ile Lys Tyr Leu Glu Thr Leu Ala
65                  70                  75                  80

Leu Leu Tyr Gly Leu Phe Leu Lys Met Asn Arg Glu Gly Val Ile Ser
                85                  90                  95

Ile Glu Ser Asp Ile Glu Lys Pro Glu Ser Ser Pro Ile Phe Ser Lys
            100                 105                 110

Tyr Pro Thr Ile Val Lys Asp Thr Lys Val Val Ala Phe Ile Ala Asp
        115                 120                 125

Thr Leu Arg Val Tyr Leu Thr Thr Gly Ala Pro Glu Asp Ile Asp Asn
    130                 135                 140

```
Leu Met Glu Ser Asp Met Lys Ile Thr His Glu Glu Leu Leu Pro
145                 150                 155                 160

Ala His Ser Ile Ser His Met Ala Glu Ser Leu Pro Gly Met Gly Ile
                165                 170                 175

Val Ala Ala Val Leu Gly Val Val Ile Thr Met Gly Lys Ile Asn Glu
            180                 185                 190

Pro Pro Glu Val Leu Gly His Tyr Ile Gly Ala Ala Leu Val Gly Thr
        195                 200                 205

Phe Ile Gly Ile Leu Phe Cys Tyr Gly Phe Phe Gly Pro Met Gly Ser
    210                 215                 220

Lys Leu Glu Thr Ser Ala Glu Ala His Phe Tyr Tyr Asn Ser Ile
225                 230                 235                 240

Lys Glu Ala Val Ala Ala Ile Arg Gly Ser Thr Pro Met Ile Ala
                245                 250                 255

Val Glu Tyr Gly Arg Arg Ala Ile Pro Asn Thr Phe Arg Pro Ser Phe
            260                 265                 270

Ser Glu Met Glu Glu Arg Leu Lys Thr Gly
        275                 280
```

<210> SEQ ID NO 11
<211> LENGTH: 717
<212> TYPE: DNA
<213> ORGANISM: Lawsonia intracellularis
<220> FEATURE:
<221> NAME/KEY: CDS
<222> LOCATION: (1)...(714)

<400> SEQUENCE: 11

```
atg tct ggc tca tgg aaa gtg gct tat gca gac ttt gtt aca gct atg      48
Met Ser Gly Ser Trp Lys Val Ala Tyr Ala Asp Phe Val Thr Ala Met
 1               5                  10                  15 atg gct ttc ttt cta ctg atg tgg att ctt gca atg aca ccc cct gag      96
Met Ala Phe Phe Leu Leu Met Trp Ile Leu Ala Met Thr Pro Pro Glu
                20                  25                  30 gtt aaa gaa ggt ctt gct gca tat ttt tct tca tct gat gct aca ttt     144
Val Lys Glu Gly Leu Ala Ala Tyr Phe Ser Ser Ser Asp Ala Thr Phe
            35                  40                  45 aaa aca cct gat agt tcg cca atc tct aac aat cct ctt atc aac caa     192
Lys Thr Pro Asp Ser Ser Pro Ile Ser Asn Asn Pro Leu Ile Asn Gln
        50                  55                  60 ata gat aaa ctt gat act cga caa tta aaa att aat gaa aca gaa caa     240
Ile Asp Lys Leu Asp Thr Arg Gln Leu Lys Ile Asn Glu Thr Glu Gln
 65                  70                  75                  80 tct cat tat gct ctt gct aat aaa tta aaa aaa atg tta atg gct gat     288
Ser His Tyr Ala Leu Ala Asn Lys Leu Lys Lys Met Leu Met Ala Asp
                85                  90                  95 gct atc cca cag tca gca aca gga ata agt gct gac gat gtt ggt gta     336
Ala Ile Pro Gln Ser Ala Thr Gly Ile Ser Ala Asp Asp Val Gly Val
            100                 105                 110 tta tta cgt gta aat tct aat tcc acg ttt ttt cct ggt aca gca act     384
Leu Leu Arg Val Asn Ser Asn Ser Thr Phe Phe Pro Gly Thr Ala Thr
        115                 120                 125 ctt aca ccc gaa ggg aaa aaa gtt atg gga act gtt tta gcc gtt ctc     432
Leu Thr Pro Glu Gly Lys Lys Val Met Gly Thr Val Leu Ala Val Leu
    130                 135                 140 cgt gaa tat aat ctt tac ctt gtg ata cgt ggc cat gct gat att ggt     480
Arg Glu Tyr Asn Leu Tyr Leu Val Ile Arg Gly His Ala Asp Ile Gly
145                 150                 155                 160
```

-continued

```
gaa ata aca aaa ggc agc cct ttt gct tct aac tgg gaa ctt tca gga      528
Glu Ile Thr Lys Gly Ser Pro Phe Ala Ser Asn Trp Glu Leu Ser Gly
            165                 170                 175 gct cgt gca gct gca gct gca cag tat ctt gta gag cac ggg ata aag      576
Ala Arg Ala Ala Ala Ala Ala Gln Tyr Leu Val Glu His Gly Ile Lys
        180                 185                 190 gct tca cga att cgc tct gta gga tat gca gat aca aga cct cta gaa      624
Ala Ser Arg Ile Arg Ser Val Gly Tyr Ala Asp Thr Arg Pro Leu Glu
    195                 200                 205 cct agt tct cct gaa gga agt aca aaa aat cgt cgt ata gaa ttc tat      672
Pro Ser Ser Pro Glu Gly Ser Thr Lys Asn Arg Arg Ile Glu Phe Tyr
210                 215                 220 ttt cat cgg cca gaa gtt atg tct tat ggc gtt gta tat taa              714
Phe His Arg Pro Glu Val Met Ser Tyr Gly Val Val Tyr *
225                 230                 235 tag                                                                   717
```

<210> SEQ ID NO 12
<211> LENGTH: 237
<212> TYPE: PRT
<213> ORGANISM: Lawsonia intracellularis

<400> SEQUENCE: 12

```
Met Ser Gly Ser Trp Lys Val Ala Tyr Ala Asp Phe Val Thr Ala Met
 1               5                  10                  15

Met Ala Phe Phe Leu Leu Met Trp Ile Leu Ala Met Thr Pro Pro Glu
            20                  25                  30

Val Lys Glu Gly Leu Ala Ala Tyr Phe Ser Ser Ser Asp Ala Thr Phe
        35                  40                  45

Lys Thr Pro Asp Ser Ser Pro Ile Ser Asn Asn Pro Leu Ile Asn Gln
    50                  55                  60

Ile Asp Lys Leu Asp Thr Arg Gln Leu Lys Ile Asn Glu Thr Glu Gln
65                  70                  75                  80

Ser His Tyr Ala Leu Ala Asn Lys Leu Lys Lys Met Leu Met Ala Asp
                85                  90                  95

Ala Ile Pro Gln Ser Ala Thr Gly Ile Ser Ala Asp Asp Val Gly Val
            100                 105                 110

Leu Leu Arg Val Asn Ser Asn Ser Thr Phe Phe Pro Gly Thr Ala Thr
        115                 120                 125

Leu Thr Pro Glu Gly Lys Lys Val Met Gly Thr Val Leu Ala Val Leu
    130                 135                 140

Arg Glu Tyr Asn Leu Tyr Leu Val Ile Arg Gly His Ala Asp Ile Gly
145                 150                 155                 160

Glu Ile Thr Lys Gly Ser Pro Phe Ala Ser Asn Trp Glu Leu Ser Gly
                165                 170                 175

Ala Arg Ala Ala Ala Ala Ala Gln Tyr Leu Val Glu His Gly Ile Lys
            180                 185                 190

Ala Ser Arg Ile Arg Ser Val Gly Tyr Ala Asp Thr Arg Pro Leu Glu
        195                 200                 205

Pro Ser Ser Pro Glu Gly Ser Thr Lys Asn Arg Arg Ile Glu Phe Tyr
    210                 215                 220

Phe His Arg Pro Glu Val Met Ser Tyr Gly Val Val Tyr
225                 230                 235
```

<210> SEQ ID NO 13
<211> LENGTH: 1047
<212> TYPE: DNA

<213> ORGANISM: Lawsonia intracellularis
<220> FEATURE:
<221> NAME/KEY: CDS
<222> LOCATION: (1)...(1044)

<400> SEQUENCE: 13

| | | | | | | | | | | | | | | | | |
|---|---|---|---|---|---|---|---|---|---|---|---|---|---|---|---|---|
| atg | ata | atc | ctt | tta | gga | act | gtt | ttt | ctt | att | gtt | ctt | atc | tct | gca | 48 |
| Met | Ile | Ile | Leu | Leu | Gly | Thr | Val | Phe | Leu | Ile | Val | Leu | Ile | Ser | Ala | |
| 1 | | | | 5 | | | | | 10 | | | | | 15 | | |
| tta | tgc | tca | atg | atg | gaa | gct | gct | ata | tac | tct | atc | cct | att | act | tat | 96 |
| Leu | Cys | Ser | Met | Met | Glu | Ala | Ala | Ile | Tyr | Ser | Ile | Pro | Ile | Thr | Tyr | |
| | | | | 20 | | | | | 25 | | | | | 30 | | |
| att | gaa | cac | ctt | cgt | gaa | cag | gga | agc | aaa | aaa | gga | gaa | aaa | ctt | tat | 144 |
| Ile | Glu | His | Leu | Arg | Glu | Gln | Gly | Ser | Lys | Lys | Gly | Glu | Lys | Leu | Tyr | |
| | | 35 | | | | | 40 | | | | | 45 | | | | |
| tat | tta | cat | agt | aat | att | gat | cag | cct | att | aca | gcc | gta | tta | ata | ttg | 192 |
| Tyr | Leu | His | Ser | Asn | Ile | Asp | Gln | Pro | Ile | Thr | Ala | Val | Leu | Ile | Leu | |
| | 50 | | | | | 55 | | | | | 60 | | | | | |
| aat | act | ata | gca | aat | act | gct | gga | gct | gcc | ctt | gct | gga | gca | att | gct | 240 |
| Asn | Thr | Ile | Ala | Asn | Thr | Ala | Gly | Ala | Ala | Leu | Ala | Gly | Ala | Ile | Ala | |
| 65 | | | | | 70 | | | | | 75 | | | | | 80 | |
| aca | aca | aca | ctt | cat | gaa | tct | act | aag | cct | ttc | ttt | gca | gca | atc | ctc | 288 |
| Thr | Thr | Thr | Leu | His | Glu | Ser | Thr | Lys | Pro | Phe | Phe | Ala | Ala | Ile | Leu | |
| | | | | 85 | | | | | 90 | | | | | 95 | | |
| acc | ttg | ctt | att | tta | gct | ttt | ggg | gaa | att | ata | cct | aaa | aca | cta | ggt | 336 |
| Thr | Leu | Leu | Ile | Leu | Ala | Phe | Gly | Glu | Ile | Ile | Pro | Lys | Thr | Leu | Gly | |
| | | | | 100 | | | | | 105 | | | | | 110 | | |
| gtt | gct | tac | tct | aaa | cgt | att | gct | ata | att | ctc | ctt | aat | cct | ctc | tct | 384 |
| Val | Ala | Tyr | Ser | Lys | Arg | Ile | Ala | Ile | Ile | Leu | Leu | Asn | Pro | Leu | Ser | |
| | | | 115 | | | | | 120 | | | | | 125 | | | |
| att | ctt | ata | gtt | act | tta | aaa | ccc | ctt | att | atg | ctt | tca | agc | tac | tta | 432 |
| Ile | Leu | Ile | Val | Thr | Leu | Lys | Pro | Leu | Ile | Met | Leu | Ser | Ser | Tyr | Leu | |
| | | 130 | | | | | 135 | | | | | 140 | | | | |
| aca | cga | ctt | gtt | tca | cct | cga | aaa | cgt | cct | aca | gtt | aca | gaa | gat | gac | 480 |
| Thr | Arg | Leu | Val | Ser | Pro | Arg | Lys | Arg | Pro | Thr | Val | Thr | Glu | Asp | Asp | |
| 145 | | | | | 150 | | | | | 155 | | | | | 160 | |
| atc | cgt | gca | ctt | aca | agt | ctt | tcc | aga | gag | tct | ggt | cgt | att | aag | cca | 528 |
| Ile | Arg | Ala | Leu | Thr | Ser | Leu | Ser | Arg | Glu | Ser | Gly | Arg | Ile | Lys | Pro | |
| | | | | 165 | | | | | 170 | | | | | 175 | | |
| tat | gaa | gaa | cat | gtc | ata | aaa | aat | atc | ctt | agt | ctt | gat | tta | aaa | tat | 576 |
| Tyr | Glu | Glu | His | Val | Ile | Lys | Asn | Ile | Leu | Ser | Leu | Asp | Leu | Lys | Tyr | |
| | | | 180 | | | | | 185 | | | | | 190 | | | |
| gct | cat | gaa | att | atg | act | ccc | aga | act | atg | gtc | ttt | tca | ctt | cat | gaa | 624 |
| Ala | His | Glu | Ile | Met | Thr | Pro | Arg | Thr | Met | Val | Phe | Ser | Leu | His | Glu | |
| | | 195 | | | | | 200 | | | | | 205 | | | | |
| aac | ctt | act | gtc | tct | gaa | gct | tat | agc | aac | ccc | aaa | ata | tgg | aac | tat | 672 |
| Asn | Leu | Thr | Val | Ser | Glu | Ala | Tyr | Ser | Asn | Pro | Lys | Ile | Trp | Asn | Tyr | |
| | 210 | | | | | 215 | | | | | 220 | | | | | |
| agt | cgc | atc | cct | act | tat | gga | gaa | aat | aac | gaa | gac | att | act | ggc | att | 720 |
| Ser | Arg | Ile | Pro | Thr | Tyr | Gly | Glu | Asn | Asn | Glu | Asp | Ile | Thr | Gly | Ile | |
| 225 | | | | | 230 | | | | | 235 | | | | | 240 | |
| atc | caa | cga | tat | gaa | att | gga | cga | tat | atg | acc | aat | gga | gaa | aca | gaa | 768 |
| Ile | Gln | Arg | Tyr | Glu | Ile | Gly | Arg | Tyr | Met | Thr | Asn | Gly | Glu | Thr | Glu | |
| | | | | 245 | | | | | 250 | | | | | 255 | | |
| aaa | aaa | ctt | tta | gaa | att | atg | caa | cca | gca | aaa | ttt | gtc | ctt | gaa | agt | 816 |
| Lys | Lys | Leu | Leu | Glu | Ile | Met | Gln | Pro | Ala | Lys | Phe | Val | Leu | Glu | Ser | |
| | | | 260 | | | | | 265 | | | | | 270 | | | |
| caa | act | gta | gat | cat | tta | ctt | ctt | gca | ttt | tta | gaa | gaa | aga | caa | cat | 864 |
| Gln | Thr | Val | Asp | His | Leu | Leu | Leu | Ala | Phe | Leu | Glu | Glu | Arg | Gln | His | |
| | | 275 | | | | | 280 | | | | | 285 | | | | |

```
ctt ttt att gta ctt gat gag tat ggg gga tta tct ggt gtt gtt tcc        912
Leu Phe Ile Val Leu Asp Glu Tyr Gly Gly Leu Ser Gly Val Val Ser
    290                 295                 300 tta gaa gat gta tta gaa act atg ctt gga aga gaa att gtt gat gaa        960
Leu Glu Asp Val Leu Glu Thr Met Leu Gly Arg Glu Ile Val Asp Glu
305                 310                 315                 320 agt gat aca aca cct gat ctt aga gca ctt gca aaa aaa aga cat agt       1008
Ser Asp Thr Thr Pro Asp Leu Arg Ala Leu Ala Lys Lys Arg His Ser
                325                 330                 335 gca tta atc caa aat aat aaa aat act ctt tta aaa taa                   1047
Ala Leu Ile Gln Asn Asn Lys Asn Thr Leu Leu Lys
                340                 345
```

<210> SEQ ID NO 14
<211> LENGTH: 348
<212> TYPE: PRT
<213> ORGANISM: Lawsonia intracellularis

<400> SEQUENCE: 14

```
Met Ile Ile Leu Leu Gly Thr Val Phe Leu Ile Val Leu Ile Ser Ala
  1               5                  10                  15

Leu Cys Ser Met Met Glu Ala Ala Ile Tyr Ser Ile Pro Ile Thr Tyr
                 20                  25                  30

Ile Glu His Leu Arg Glu Gln Gly Ser Lys Lys Gly Glu Lys Leu Tyr
             35                  40                  45

Tyr Leu His Ser Asn Ile Asp Gln Pro Ile Thr Ala Val Leu Ile Leu
         50                  55                  60

Asn Thr Ile Ala Asn Thr Ala Gly Ala Ala Leu Ala Gly Ala Ile Ala
 65                  70                  75                  80

Thr Thr Thr Leu His Glu Ser Thr Lys Pro Phe Phe Ala Ala Ile Leu
                 85                  90                  95

Thr Leu Leu Ile Leu Ala Phe Gly Glu Ile Ile Pro Lys Thr Leu Gly
            100                 105                 110

Val Ala Tyr Ser Lys Arg Ile Ala Ile Ile Leu Leu Asn Pro Leu Ser
        115                 120                 125

Ile Leu Ile Val Thr Leu Lys Pro Leu Ile Met Ser Ser Tyr Leu
    130                 135                 140

Thr Arg Leu Val Ser Pro Arg Lys Arg Pro Thr Val Thr Glu Asp Asp
145                 150                 155                 160

Ile Arg Ala Leu Thr Ser Leu Ser Arg Glu Ser Gly Arg Ile Lys Pro
                165                 170                 175

Tyr Glu Glu His Val Ile Lys Asn Ile Leu Ser Leu Asp Leu Lys Tyr
            180                 185                 190

Ala His Glu Ile Met Thr Pro Arg Thr Met Val Phe Ser Leu His Glu
        195                 200                 205

Asn Leu Thr Val Ser Glu Ala Tyr Ser Asn Pro Lys Ile Trp Asn Tyr
    210                 215                 220

Ser Arg Ile Pro Thr Tyr Gly Glu Asn Asn Glu Asp Ile Thr Gly Ile
225                 230                 235                 240

Ile Gln Arg Tyr Glu Ile Gly Arg Tyr Met Thr Asn Gly Glu Thr Glu
                245                 250                 255

Lys Lys Leu Leu Glu Ile Met Gln Pro Ala Lys Phe Val Leu Glu Ser
            260                 265                 270

Gln Thr Val Asp His Leu Leu Leu Ala Phe Leu Glu Glu Arg Gln His
        275                 280                 285

Leu Phe Ile Val Leu Asp Glu Tyr Gly Gly Leu Ser Gly Val Val Ser
```

```
                     290                 295                 300
Leu Glu Asp Val Leu Glu Thr Met Leu Gly Arg Glu Ile Val Asp Glu
305                 310                 315                 320

Ser Asp Thr Thr Pro Asp Leu Arg Ala Leu Ala Lys Lys Arg His Ser
                325                 330                 335

Ala Leu Ile Gln Asn Asn Lys Asn Thr Leu Leu Lys
            340                 345

<210> SEQ ID NO 15
<211> LENGTH: 1812
<212> TYPE: DNA
<213> ORGANISM: Lawsonia intracellularis
<220> FEATURE:
<221> NAME/KEY: CDS
<222> LOCATION: (1)...(1809)

<400> SEQUENCE: 15 atg caa aaa gta tgt tat ttt ttt ctt ata acc ttt ttc tac ttt ttc      48
Met Gln Lys Val Cys Tyr Phe Phe Leu Ile Thr Phe Phe Tyr Phe Phe
  1               5                  10                  15 ata aca gaa aat tat ctc ttt gct aca tca att acc act tcc aca att      96
Ile Thr Glu Asn Tyr Leu Phe Ala Thr Ser Ile Thr Thr Ser Thr Ile
             20                  25                  30 aac caa caa cat ata gca tat aca gtt act ttt acc tct cca gaa aat     144
Asn Gln Gln His Ile Ala Tyr Thr Val Thr Phe Thr Ser Pro Glu Asn
         35                  40                  45 cct aat ctt gca aca gag atg gaa aca cat agt gaa tta gta aag ctt     192
Pro Asn Leu Ala Thr Glu Met Glu Thr His Ser Glu Leu Val Lys Leu
     50                  55                  60 gca aat caa tct tta gat agt aaa ata ggt tta aat tta cgt gtt aaa     240
Ala Asn Gln Ser Leu Asp Ser Lys Ile Gly Leu Asn Leu Arg Val Lys
 65                  70                  75                  80 gaa gat ata agt aca gca caa aaa att ctt gac tcg aat ggt tat tat     288
Glu Asp Ile Ser Thr Ala Gln Lys Ile Leu Asp Ser Asn Gly Tyr Tyr
                 85                  90                  95 agt gga agt gtc gag gga aag att gac tgg cag acg aac cct att agt     336
Ser Gly Ser Val Glu Gly Lys Ile Asp Trp Gln Thr Asn Pro Ile Ser
            100                 105                 110 atc caa atc caa ttt aaa cca aat gta caa tat aaa ata aat aca ata     384
Ile Gln Ile Gln Phe Lys Pro Asn Val Gln Tyr Lys Ile Asn Thr Ile
        115                 120                 125 cat atc caa tac ctt gat agt gaa ctt gca tat ctc cct ctt tcc tta     432
His Ile Gln Tyr Leu Asp Ser Glu Leu Ala Tyr Leu Pro Leu Ser Leu
    130                 135                 140 gaa gaa ttc aat ctc tct aaa ggt aat cct gct ctt gct gtt aat atc     480
Glu Glu Phe Asn Leu Ser Lys Gly Asn Pro Ala Leu Ala Val Asn Ile
145                 150                 155                 160 cta tcc tct gta agt agc ctc atg caa tat ata cat aat aat gga tat     528
Leu Ser Ser Val Ser Ser Leu Met Gln Tyr Ile His Asn Asn Gly Tyr
                165                 170                 175 cca tta gcc aaa ata aaa aaa act caa tac ata att aat cgg atg gat     576
Pro Leu Ala Lys Ile Lys Lys Thr Gln Tyr Ile Ile Asn Arg Met Asp
            180                 185                 190 tat aca ttt gat att gat tta gta ata aga caa gga ccg tta ctc cat     624
Tyr Thr Phe Asp Ile Asp Leu Val Ile Arg Gln Gly Pro Leu Leu His
        195                 200                 205 atg ggt aaa gta caa cct caa cat aat ctc aat att tca aca ata ttc     672
Met Gly Lys Val Gln Pro Gln His Asn Leu Asn Ile Ser Thr Ile Phe
    210                 215                 220 cta aat aaa att gct aca tgg aag gaa gga agg gta tgg aac aat gca     720
```

| | | |
|---|---|---|
| Leu Asn Lys Ile Ala Thr Trp Lys Glu Gly Arg Val Trp Asn Asn Ala<br>225              230              235              240 | | |
| ctc ctt gat tct tat cga aca cgg ctt caa caa aca ggc ctt ttc agt<br>Leu Leu Asp Ser Tyr Arg Thr Arg Leu Gln Gln Thr Gly Leu Phe Ser<br>            245              250              255 | 768 |
| tct ata act ctc aat cca agg aat caa aaa gaa caa aat ggt aac acc<br>Ser Ile Thr Leu Asn Pro Arg Asn Gln Lys Glu Gln Asn Gly Asn Thr<br>                260              265              270 | 816 |
| tct ata gaa ctt gtt gca aca gaa gcc cct cca agg act att agt ggt<br>Ser Ile Glu Leu Val Ala Thr Glu Ala Pro Pro Arg Thr Ile Ser Gly<br>            275              280              285 | 864 |
| ggc tta caa tac tct tct gat caa ggt att ggt gca cgt ggg act tgg<br>Gly Leu Gln Tyr Ser Ser Asp Gln Gly Ile Gly Ala Arg Gly Thr Trp<br>290              295              300 | 912 |
| gaa cat cga aat gtt ttt ggt aat gga gaa ctt ttt cgt ata aca gca<br>Glu His Arg Asn Val Phe Gly Asn Gly Glu Leu Phe Arg Ile Thr Ala<br>305              310              315              320 | 960 |
| cca ata agt cga gat gat caa aaa att atg gca aac ttc caa aaa cca<br>Pro Ile Ser Arg Asp Asp Gln Lys Ile Met Ala Asn Phe Gln Lys Pro<br>                325              330              335 | 1008 |
| gcc ttt ggc cgt cca aat caa tca tta att agt gaa gca caa ctt aaa<br>Ala Phe Gly Arg Pro Asn Gln Ser Leu Ile Ser Glu Ala Gln Leu Lys<br>            340              345              350 | 1056 |
| aaa gaa aat aca aaa agt tac aaa caa caa ctt gca tct att gct tta<br>Lys Glu Asn Thr Lys Ser Tyr Lys Gln Gln Leu Ala Ser Ile Ala Leu<br>                355              360              365 | 1104 |
| gga att gaa cga caa ttt aat aga cgt tgg ttt ggt agt agc agt ctt<br>Gly Ile Glu Arg Gln Phe Asn Arg Arg Trp Phe Gly Ser Ser Ser Leu<br>370              375              380 | 1152 |
| tca gtt gat aca gga ttt atg gat gat cga gat tct ata aaa aaa ata<br>Ser Val Asp Thr Gly Phe Met Asp Asp Arg Asp Ser Ile Lys Lys Ile<br>385              390              395              400 | 1200 |
| ttt act ctt ttt ggc atc ccc tta tca ata aca agg gat agt tct aaa<br>Phe Thr Leu Phe Gly Ile Pro Leu Ser Ile Thr Arg Asp Ser Ser Lys<br>            405              410              415 | 1248 |
| gat cct ctt aat cct atc caa gga aca aaa gct acc tta aat gtt act<br>Asp Pro Leu Asn Pro Ile Gln Gly Thr Lys Ala Thr Leu Asn Val Thr<br>                420              425              430 | 1296 |
| cct tat att ggt aaa tat aaa aaa aag att ttg act tta cgt agt cgg<br>Pro Tyr Ile Gly Lys Tyr Lys Lys Lys Ile Leu Thr Leu Arg Ser Arg<br>            435              440              445 | 1344 |
| ttt gat ttt agc ttt tac ata gac gtt ctt aaa aca ggg aaa ctt atc<br>Phe Asp Phe Ser Phe Tyr Ile Asp Val Leu Lys Thr Gly Lys Leu Ile<br>450              455              460 | 1392 |
| ttg gct aac aaa ata gca ata ggt tcc ctc cta ggg aaa gat ata gaa<br>Leu Ala Asn Lys Ile Ala Ile Gly Ser Leu Leu Gly Lys Asp Ile Glu<br>465              470              475              480 | 1440 |
| aac tat cct gca ata cta agg ttt tat gct ggg ggt ggt agt gta<br>Asn Tyr Pro Ala Ile Leu Arg Phe Tyr Ala Gly Gly Gly Gly Ser Val<br>                485              490              495 | 1488 |
| aga ggg tat gac tat caa tca ttg gga cca aaa aat aaa tat ggg gat<br>Arg Gly Tyr Asp Tyr Gln Ser Leu Gly Pro Lys Asn Lys Tyr Gly Asp<br>            500              505              510 | 1536 |
| gct att gga gga ctt tct ttt tca act att agt ttt gaa tta cga tta<br>Ala Ile Gly Gly Leu Ser Phe Ser Thr Ile Ser Phe Glu Leu Arg Leu<br>                515              520              525 | 1584 |
| aaa ata aca gaa tcc att ggc att gtg cca att tat tgg atg ggg gaa<br>Lys Ile Thr Glu Ser Ile Gly Ile Val Pro Ile Tyr Trp Met Gly Glu<br>530              535              540 | 1632 |

```
tat tta cga aaa aaa aat ttc ctg act tta aaa aaa tca ata tat tgg    1680
Tyr Leu Arg Lys Lys Asn Phe Leu Thr Leu Lys Lys Ser Ile Tyr Trp
545                 550                 555                 560 ggg gta ggc ctg ggg cta cga tat tat aca agt ttt gcc ccc ata cgt    1728
Gly Val Gly Leu Gly Leu Arg Tyr Tyr Thr Ser Phe Ala Pro Ile Arg
                565                 570                 575 tta gat ata gca act cca ctt caa gat aga agc cat aat aaa cac ttt    1776
Leu Asp Ile Ala Thr Pro Leu Gln Asp Arg Ser His Asn Lys His Phe
            580                 585                 590 caa ctt tat att agt att ggg caa gca ttc taa tga                    1812
Gln Leu Tyr Ile Ser Ile Gly Gln Ala Phe *
            595                 600
```

<210> SEQ ID NO 16
<211> LENGTH: 602
<212> TYPE: PRT
<213> ORGANISM: Lawsonia intracellularis

<400> SEQUENCE: 16

```
Met Gln Lys Val Cys Tyr Phe Phe Leu Ile Thr Phe Tyr Phe Phe
1               5                  10                  15

Ile Thr Glu Asn Tyr Leu Phe Ala Thr Ser Ile Thr Thr Ser Thr Ile
            20                  25                  30

Asn Gln Gln His Ile Ala Tyr Thr Val Thr Phe Thr Ser Pro Glu Asn
        35                  40                  45

Pro Asn Leu Ala Thr Glu Met Glu Thr His Ser Glu Leu Val Lys Leu
    50                  55                  60

Ala Asn Gln Ser Leu Asp Ser Lys Ile Gly Leu Asn Leu Arg Val Lys
65                  70                  75                  80

Glu Asp Ile Ser Thr Ala Gln Lys Ile Leu Asp Ser Asn Gly Tyr Tyr
                85                  90                  95

Ser Gly Ser Val Glu Gly Lys Ile Asp Trp Gln Thr Asn Pro Ile Ser
            100                 105                 110

Ile Gln Ile Gln Phe Lys Pro Asn Val Gln Tyr Lys Ile Asn Thr Ile
        115                 120                 125

His Ile Gln Tyr Leu Asp Ser Glu Leu Ala Tyr Leu Pro Leu Ser Leu
    130                 135                 140

Glu Glu Phe Asn Leu Ser Lys Gly Asn Pro Ala Leu Ala Val Asn Ile
145                 150                 155                 160

Leu Ser Ser Val Ser Ser Leu Met Gln Tyr Ile His Asn Asn Gly Tyr
                165                 170                 175

Pro Leu Ala Lys Ile Lys Lys Thr Gln Tyr Ile Ile Asn Arg Met Asp
            180                 185                 190

Tyr Thr Phe Asp Ile Asp Leu Val Ile Arg Gln Gly Pro Leu Leu His
        195                 200                 205

Met Gly Lys Val Gln Pro Gln His Asn Leu Asn Ile Ser Thr Ile Phe
    210                 215                 220

Leu Asn Lys Ile Ala Thr Trp Lys Glu Gly Arg Val Trp Asn Asn Ala
225                 230                 235                 240

Leu Leu Asp Ser Tyr Arg Thr Arg Leu Gln Gln Thr Gly Leu Phe Ser
                245                 250                 255

Ser Ile Thr Leu Asn Pro Arg Asn Gln Lys Glu Gln Asn Gly Asn Thr
            260                 265                 270

Ser Ile Glu Leu Val Ala Thr Glu Ala Pro Pro Arg Thr Ile Ser Gly
        275                 280                 285

Gly Leu Gln Tyr Ser Ser Asp Gln Gly Ile Gly Ala Arg Gly Thr Trp
```

```
                290                 295                 300
Glu His Arg Asn Val Phe Gly Asn Gly Glu Leu Phe Arg Ile Thr Ala
305                 310                 315                 320

Pro Ile Ser Arg Asp Asp Gln Lys Ile Met Ala Asn Phe Gln Lys Pro
                325                 330                 335

Ala Phe Gly Arg Pro Asn Gln Ser Leu Ile Ser Glu Ala Gln Leu Lys
                340                 345                 350

Lys Glu Asn Thr Lys Ser Tyr Lys Gln Gln Leu Ala Ser Ile Ala Leu
                355                 360                 365

Gly Ile Glu Arg Gln Phe Asn Arg Arg Trp Phe Gly Ser Ser Ser Leu
370                 375                 380

Ser Val Asp Thr Gly Phe Met Asp Asp Arg Asp Ser Ile Lys Lys Ile
385                 390                 395                 400

Phe Thr Leu Phe Gly Ile Pro Leu Ser Ile Thr Arg Asp Ser Ser Lys
                405                 410                 415

Asp Pro Leu Asn Pro Ile Gln Gly Thr Lys Ala Thr Leu Asn Val Thr
                420                 425                 430

Pro Tyr Ile Gly Lys Tyr Lys Lys Ile Leu Thr Leu Arg Ser Arg
                435                 440                 445

Phe Asp Phe Ser Phe Tyr Ile Asp Val Leu Lys Thr Gly Lys Leu Ile
                450                 455                 460

Leu Ala Asn Lys Ile Ala Ile Gly Ser Leu Leu Gly Lys Asp Ile Glu
465                 470                 475                 480

Asn Tyr Pro Ala Ile Leu Arg Phe Tyr Ala Gly Gly Gly Ser Val
                485                 490                 495

Arg Gly Tyr Asp Tyr Gln Ser Leu Gly Pro Lys Asn Lys Tyr Gly Asp
                500                 505                 510

Ala Ile Gly Gly Leu Ser Phe Ser Thr Ile Ser Phe Glu Leu Arg Leu
                515                 520                 525

Lys Ile Thr Glu Ser Ile Gly Ile Val Pro Ile Tyr Trp Met Gly Glu
                530                 535                 540

Tyr Leu Arg Lys Lys Asn Phe Leu Thr Leu Lys Lys Ser Ile Tyr Trp
545                 550                 555                 560

Gly Val Gly Leu Gly Leu Arg Tyr Tyr Thr Ser Phe Ala Pro Ile Arg
                565                 570                 575

Leu Asp Ile Ala Thr Pro Leu Gln Asp Arg Ser His Asn Lys His Phe
                580                 585                 590

Gln Leu Tyr Ile Ser Ile Gly Gln Ala Phe
                595                 600
```

<210> SEQ ID NO 17
<211> LENGTH: 4149
<212> TYPE: DNA
<213> ORGANISM: Lawsonia intracellularis
<220> FEATURE:
<221> NAME/KEY: CDS
<222> LOCATION: (1)...(4146)

<400> SEQUENCE: 17

```
atg aat aac aca aaa ata ctt tct aag tta ctc tat acc ctc tta gga    48
Met Asn Asn Thr Lys Ile Leu Ser Lys Leu Leu Tyr Thr Leu Leu Gly
  1               5                  10                  15 gca ttt acg tta ttt tta gga ctt att att aca ggc att ctt ttt ata    96
Ala Phe Thr Leu Phe Leu Gly Leu Ile Ile Thr Gly Ile Leu Phe Ile
             20                  25                  30 cgg acc tct aca ggc att gct tgg att aaa aat aca gtt tct tct tta   144
```

```
                Arg Thr Ser Thr Gly Ile Ala Trp Ile Lys Asn Thr Val Ser Ser Leu
                         35                  40                  45 ctt caa caa caa gga att ata cta caa gta tct tca att att gga cca          192
Leu Gln Gln Gln Gly Ile Ile Leu Gln Val Ser Ser Ile Ile Gly Pro
     50                  55                  60 ttc cca gaa caa att act att aat gaa ctt agc ctt agt gat gtg aat          240
Phe Pro Glu Gln Ile Thr Ile Asn Glu Leu Ser Leu Ser Asp Val Asn
 65                  70                  75                  80 gga act tac ctt aca ata tct aac tta gaa atc caa tca aac tta tgg          288
Gly Thr Tyr Leu Thr Ile Ser Asn Leu Glu Ile Gln Ser Asn Leu Trp
                 85                  90                  95 gct tta ttc aaa ggt caa ctt gaa att ctg tct ttt gaa ctt aat gat          336
Ala Leu Phe Lys Gly Gln Leu Glu Ile Leu Ser Phe Glu Leu Asn Asp
                100                 105                 110 ctt gta tta tat cgc tta ccc tca aat aat aat cta aaa aaa tca tct          384
Leu Val Leu Tyr Arg Leu Pro Ser Asn Asn Asn Leu Lys Lys Ser Ser
            115                 120                 125 aca agt ttt gtg tta cct cac ata tca ttt gat tta act cca tgg tgg          432
Thr Ser Phe Val Leu Pro His Ile Ser Phe Asp Leu Thr Pro Trp Trp
    130                 135                 140 act gaa cat att cgt att caa aac atc cat att aac aat aca caa ctt          480
Thr Glu His Ile Arg Ile Gln Asn Ile His Ile Asn Asn Thr Gln Leu
145                 150                 155                 160 tcc tct gat att ata ggt att cca ttg gta tta tcc ctt gag ggt gat          528
Ser Ser Asp Ile Ile Gly Ile Pro Leu Val Leu Ser Leu Glu Gly Asp
                165                 170                 175 ggt aca tta aca aat tgg aat gga aca ttt caa cta tcc tct tct aac          576
Gly Thr Leu Thr Asn Trp Asn Gly Thr Phe Gln Leu Ser Ser Ser Asn
            180                 185                 190 aaa aca aaa att ata gga acg ctt cgt tac caa ggg aat aag aca caa          624
Lys Thr Lys Ile Ile Gly Thr Leu Arg Tyr Gln Gly Asn Lys Thr Gln
    195                 200                 205 ttt ttt gaa tat gtt cat cct aca cgg ata gta aca cta gag ata gac          672
Phe Phe Glu Tyr Val His Pro Thr Arg Ile Val Thr Leu Glu Ile Asp
210                 215                 220 agc gta gct gat aaa aag tca tat aat aat agt atc ctt gaa caa cct          720
Ser Val Ala Asp Lys Lys Ser Tyr Asn Asn Ser Ile Leu Glu Gln Pro
225                 230                 235                 240 cta cat tta cac ctt tct att tat cct gaa cat aat aga att atc tta          768
Leu His Leu His Leu Ser Ile Tyr Pro Glu His Asn Arg Ile Ile Leu
                245                 250                 255 cac tca tta cta gct gaa tat ggt agc tgg tta ctt aca tca gaa agt          816
His Ser Leu Leu Ala Glu Tyr Gly Ser Trp Leu Leu Thr Ser Glu Ser
            260                 265                 270 att gaa gta tct aat gag caa tta aaa gga aat att tta tta aaa tat          864
Ile Glu Val Ser Asn Glu Gln Leu Lys Gly Asn Ile Leu Leu Lys Tyr
    275                 280                 285 aat gga gaa gct act cat caa ctt cct ata aaa aaa ctt aac tca tca          912
Asn Gly Glu Ala Thr His Gln Leu Pro Ile Lys Lys Leu Asn Ser Ser
290                 295                 300 att acc ctc agt ggc tca cta aat aaa cct aat ttt agt ata caa atg          960
Ile Thr Leu Ser Gly Ser Leu Asn Lys Pro Asn Phe Ser Ile Gln Met
305                 310                 315                 320 aca tta cct gaa att aac att aca aaa aac ata ata gat ctt caa aca         1008
Thr Leu Pro Glu Ile Asn Ile Thr Lys Asn Ile Ile Asp Leu Gln Thr
                325                 330                 335 gaa ctt gtt att aat cta gga ctt ttc tct act cac tct gat att ctt         1056
Glu Leu Val Ile Asn Leu Gly Leu Phe Ser Thr His Ser Asp Ile Leu
            340                 345                 350
```

```
aca tct ggg aca att aca gta cag gga gaa act ata ccc aat agt att    1104
Thr Ser Gly Thr Ile Thr Val Gln Gly Glu Thr Ile Pro Asn Ser Ile
        355                 360                 365 ctt tcc agt gca gtt gat ata ata gcc tct aca aca aca cat aca att    1152
Leu Ser Ser Ala Val Asp Ile Ile Ala Ser Thr Thr Thr His Thr Ile
370                 375                 380 acc tta gag cat gca acc tta aca tct cca gaa atg cat ttt tcc cta    1200
Thr Leu Glu His Ala Thr Leu Thr Ser Pro Glu Met His Phe Ser Leu
385                 390                 395                 400 tct gga gaa ttt aat agt ctt cta gga aat atc gat gca aac cta aaa    1248
Ser Gly Glu Phe Asn Ser Leu Leu Gly Asn Ile Asp Ala Asn Leu Lys
                405                 410                 415 ggt aat act cca act ctt agt ata ttt tct tct ctt ctt gga cta cct    1296
Gly Asn Thr Pro Thr Leu Ser Ile Phe Ser Ser Leu Leu Gly Leu Pro
        420                 425                 430 gat ctt act ggg caa agt aac att act ata gga tta cac cgt caa ggg    1344
Asp Leu Thr Gly Gln Ser Asn Ile Thr Ile Gly Leu His Arg Gln Gly
    435                 440                 445 tct tcc tct tca ata gaa gga aca gca act gtc tca ctt aat aat atg    1392
Ser Ser Ser Ser Ile Glu Gly Thr Ala Thr Val Ser Leu Asn Asn Met
450                 455                 460 aac tgg gga gta caa gca tta cag ggg aca tta ggt gat aat gca act    1440
Asn Trp Gly Val Gln Ala Leu Gln Gly Thr Leu Gly Asp Asn Ala Thr
465                 470                 475                 480 cta agt gga ata tat aat tta act ccc ata gac tgg tct att tct tta    1488
Leu Ser Gly Ile Tyr Asn Leu Thr Pro Ile Asp Trp Ser Ile Ser Leu
                485                 490                 495 aac aaa ttg aaa tta aca gca aag aat gtt tat gct gaa ggc ctt att    1536
Asn Lys Leu Lys Leu Thr Ala Lys Asn Val Tyr Ala Glu Gly Leu Ile
        500                 505                 510 aat ttt caa aaa aaa tac ata gat agc tct ata aat ctt ata att cct    1584
Asn Phe Gln Lys Lys Tyr Ile Asp Ser Ser Ile Asn Leu Ile Ile Pro
    515                 520                 525 aac ctt cag cta ata gct cct cct ata tct gga gag tta caa tcc tta    1632
Asn Leu Gln Leu Ile Ala Pro Pro Ile Ser Gly Glu Leu Gln Ser Leu
530                 535                 540 att aca gtg tct gga aaa ctt gac gca cct tct ata gaa agc aaa att    1680
Ile Thr Val Ser Gly Lys Leu Asp Ala Pro Ser Ile Glu Ser Lys Ile
545                 550                 555                 560 ttt tca tca caa ctc acc tgg aat gcg ctc caa ctt aat aat cct caa    1728
Phe Ser Ser Gln Leu Thr Trp Asn Ala Leu Gln Leu Asn Asn Pro Gln
                565                 570                 575 ctc ata ata act act act caa tct tct tcc tct gcg att aaa ggt aat    1776
Leu Ile Ile Thr Thr Thr Gln Ser Ser Ser Ser Ala Ile Lys Gly Asn
        580                 585                 590 ata aca ctc tcg gct gag cca gct tca tct gag gca tta acc ttt tca    1824
Ile Thr Leu Ser Ala Glu Pro Ala Ser Ser Glu Ala Leu Thr Phe Ser
    595                 600                 605 agt aat tgg gga atc cta cct acg gaa ata cta gta gaa aaa att ata    1872
Ser Asn Trp Gly Ile Leu Pro Thr Glu Ile Leu Val Glu Lys Ile Ile
610                 615                 620 gga aat ata tta gga gta aat ctt gat ggt aat att aaa ata aca aaa    1920
Gly Asn Ile Leu Gly Val Asn Leu Asp Gly Asn Ile Lys Ile Thr Lys
625                 630                 635                 640 aaa gat tac ctt ata aat ggt gat att att gca gaa gtt cag tct tgg    1968
Lys Asp Tyr Leu Ile Asn Gly Asp Ile Ile Ala Glu Val Gln Ser Trp
                645                 650                 655 aaa gat att gca aac ata ttg caa ata cct att aga ggt tca gca tca    2016
Lys Asp Ile Ala Asn Ile Leu Gln Ile Pro Ile Arg Gly Ser Ala Ser
        660                 665                 670
```

| | |
|---|---|
| ata aaa ata cag ttt gat cca aag aat caa caa tgt att tct act caa<br>Ile Lys Ile Gln Phe Asp Pro Lys Asn Gln Gln Cys Ile Ser Thr Gln<br>       675               680               685 | 2064 |
| tgg caa tta aaa aat ttc ata tta ggt aat aat ttt aat gta act act<br>Trp Gln Leu Lys Asn Phe Ile Leu Gly Asn Asn Phe Asn Val Thr Thr<br>690               695              700 | 2112 |
| ata aaa gga aga gca gat aca ata caa ctt cat aag aat cct aca att<br>Ile Lys Gly Arg Ala Asp Thr Ile Gln Leu His Lys Asn Pro Thr Ile<br>705               710              715              720 | 2160 |
| gct ctc tct tca aaa att ggt gct ggt aca tat gaa gac ttt caa tgg<br>Ala Leu Ser Ser Lys Ile Gly Ala Gly Thr Tyr Glu Asp Phe Gln Trp<br>               725              730              735 | 2208 |
| aca caa ggg acg tta gac ata aaa ggc aca tta aaa aat ttt aat agt<br>Thr Gln Gly Thr Leu Asp Ile Lys Gly Thr Leu Lys Asn Phe Asn Ser<br>740                     745              750 | 2256 |
| aaa ata aat ata gca gga caa aca act gta aac gca aac ttt caa aca<br>Lys Ile Asn Ile Ala Gly Gln Thr Thr Val Asn Ala Asn Phe Gln Thr<br>               755              760              765 | 2304 |
| aat ctt ttt gaa aaa aat att aat ata act act ctt aat tta aaa aat<br>Asn Leu Phe Glu Lys Asn Ile Asn Ile Thr Thr Leu Asn Leu Lys Asn<br>770                     775              780 | 2352 |
| att caa aaa aat ata gga att aag ctc ctt cag cca ata aaa att ata<br>Ile Gln Lys Asn Ile Gly Ile Lys Leu Leu Gln Pro Ile Lys Ile Ile<br>785               790              795              800 | 2400 |
| gtc tca cct caa caa ttt gtt ctt aat aac tgt tca cta gca att ctt<br>Val Ser Pro Gln Gln Phe Val Leu Asn Asn Cys Ser Leu Ala Ile Leu<br>                     805              810              815 | 2448 |
| cca tct gga aca att aca act gat ata tat gtt act cct caa cga ctt<br>Pro Ser Gly Thr Ile Thr Thr Asp Ile Tyr Val Thr Pro Gln Arg Leu<br>820                     825              830 | 2496 |
| aat gct aat gca atc att aaa gaa gtt tca ctt ctc tct ttc caa cca<br>Asn Ala Asn Ala Ile Ile Lys Glu Val Ser Leu Leu Ser Phe Gln Pro<br>               835              840              845 | 2544 |
| ttt agt ata ctt ctt cct caa gga aat ata aat gga cac ata aca ctt<br>Phe Ser Ile Leu Leu Pro Gln Gly Asn Ile Asn Gly His Ile Thr Leu<br>850                     855              860 | 2592 |
| aca gga ata cct agt aaa cct aaa gga aca ctc tca ttt gat att cta<br>Thr Gly Ile Pro Ser Lys Pro Lys Gly Thr Leu Ser Phe Asp Ile Leu<br>865               870              875              880 | 2640 |
| aac ata cat tat cca agg cca aat cca tca ata gca aac tta cat gta<br>Asn Ile His Tyr Pro Arg Pro Asn Pro Ser Ile Ala Asn Leu His Val<br>               885              890              895 | 2688 |
| gaa ggg gaa att ata tct tct cct aac aat ata tgt aaa ctt aat gca<br>Glu Gly Glu Ile Ile Ser Ser Pro Asn Asn Ile Cys Lys Leu Asn Ala<br>                   900              905              910 | 2736 |
| acc cta aca gaa aaa aaa gag cct ata cct ata tca ata caa gca aca<br>Thr Leu Thr Glu Lys Lys Glu Pro Ile Pro Ile Ser Ile Gln Ala Thr<br>               915              920              925 | 2784 |
| ctc cct ttt gag ttc aca gaa aac aat atc cct atg cta tct aaa atg<br>Leu Pro Phe Glu Phe Thr Glu Asn Asn Ile Pro Met Leu Ser Lys Met<br>930                     935              940 | 2832 |
| agg cct ttt tct gcc cat atc aag tgg act gga ata tta gat aca ctt<br>Arg Pro Phe Ser Ala His Ile Lys Trp Thr Gly Ile Leu Asp Thr Leu<br>945               950              955              960 | 2880 |
| tgg aaa ctc att cca ctt act gat tac att atg gct ggg aat gga tct<br>Trp Lys Leu Ile Pro Leu Thr Asp Tyr Ile Met Ala Gly Asn Gly Ser<br>               965              970              975 | 2928 |
| tta gat gct tct ctt tct ggg act tta gat agt cca aca tat gca att<br>Leu Asp Ala Ser Leu Ser Gly Thr Leu Asp Ser Pro Thr Tyr Ala Ile | 2976 |

|  |  |  |  |  |  |  |  |  |  |  |  |  |  |  |  |
|---|---|---|---|---|---|---|---|---|---|---|---|---|---|---|---|

```
                        980                 985                 990
ata aca aca ctt tct aat gct aac ttt caa gat ctc tcc ctt ggt ctt         3024
Ile Thr Thr Leu Ser Asn Ala Asn Phe Gln Asp Leu Ser Leu Gly Leu
            995                 1000                1005 tac tta gaa aat atc aat gct aaa tta cag gtc ttt tct aat aga atc         3072
Tyr Leu Glu Asn Ile Asn Ala Lys Leu Gln Val Phe Ser Asn Arg Ile
    1010                1015                1020 tcc cat att caa gct aca gca tct gat ggt aaa caa ggt agt ata caa         3120
Ser His Ile Gln Ala Thr Ala Ser Asp Gly Lys Gln Gly Ser Ile Gln
1025                1030                1035                1040 ctt att ggt aat att ggc tca tct aaa gaa cac ttt cct ttg tct att         3168
Leu Ile Gly Asn Ile Gly Ser Ser Lys Glu His Phe Pro Leu Ser Ile
            1045                1050                1055 aat ggc tcc ttt aca aac ctt gct cca tta caa cgt aaa gac cta agt         3216
Asn Gly Ser Phe Thr Asn Leu Ala Pro Leu Gln Arg Lys Asp Leu Ser
    1060                1065                1070 ctt aca ctt tca gga gca gct act ctt gaa gga aca tta aaa cag tct         3264
Leu Thr Leu Ser Gly Ala Ala Thr Leu Glu Gly Thr Leu Lys Gln Ser
        1075                1080                1085 gaa gtt aaa ggc gat att gtt att aac caa ggc gaa ttt caa ctt act         3312
Glu Val Lys Gly Asp Ile Val Ile Asn Gln Gly Glu Phe Gln Leu Thr
    1090                1095                1100 gaa ggg tta acc agt aat att cca act ctt aat gta gtt gat agc act         3360
Glu Gly Leu Thr Ser Asn Ile Pro Thr Leu Asn Val Val Asp Ser Thr
1105                1110                1115                1120 caa caa caa aat aca aag acc aaa aaa gct acc tat caa caa cct acc         3408
Gln Gln Gln Asn Thr Lys Thr Lys Lys Ala Thr Tyr Gln Gln Pro Thr
            1125                1130                1135 tta tct att gcg tta agt atc ccg aat cgt ttt ttt gtc cgt agt agt         3456
Leu Ser Ile Ala Leu Ser Ile Pro Asn Arg Phe Phe Val Arg Ser Ser
    1140                1145                1150 atg ttt gaa agt gag tgg gga ggg aac cta act att aac aaa gtc ata         3504
Met Phe Glu Ser Glu Trp Gly Gly Asn Leu Thr Ile Asn Lys Val Ile
        1155                1160                1165 aca agt cct gtt att aca gga gca cta act tct ata aga gga aat ttt         3552
Thr Ser Pro Val Ile Thr Gly Ala Leu Thr Ser Ile Arg Gly Asn Phe
    1170                1175                1180 aat tta cta gga aaa caa ttt tct ctt gct aaa agt aca ata tca ttt         3600
Asn Leu Leu Gly Lys Gln Phe Ser Leu Ala Lys Ser Thr Ile Ser Phe
1185                1190                1195                1200 tca gga tca gtt cca cca aac cca cta ctc aat att tct tta aca tat         3648
Ser Gly Ser Val Pro Pro Asn Pro Leu Leu Asn Ile Ser Leu Thr Tyr
            1205                1210                1215 tca tca cct tct att aca gct ata ggc att att aaa ggt aca act agt         3696
Ser Ser Pro Ser Ile Thr Ala Ile Gly Ile Ile Lys Gly Thr Thr Ser
    1220                1225                1230 aat cct aat att act ttt tca agt aca cca cct tta cct caa gat gaa         3744
Asn Pro Asn Ile Thr Phe Ser Ser Thr Pro Pro Leu Pro Gln Asp Glu
        1235                1240                1245 ata gtt tcc caa gtt ctt ttt ggt aaa agc tca caa agt ctt agc agg         3792
Ile Val Ser Gln Val Leu Phe Gly Lys Ser Ser Gln Ser Leu Ser Arg
    1250                1255                1260 ata caa gcc ata caa ctt gct caa gaa tta gca aac tta aca gga ttt         3840
Ile Gln Ala Ile Gln Leu Ala Gln Glu Leu Ala Asn Leu Thr Gly Phe
1265                1270                1275                1280 aat act gga agt atg aat ttc cta aca aat att cga cag aca tta ggg         3888
Asn Thr Gly Ser Met Asn Phe Leu Thr Asn Ile Arg Gln Thr Leu Gly
            1285                1290                1295 tta gat ata ctt agc tta ggg aca act tct aat aga aaa gcc aat aca         3936
```

-continued

```
Leu Asp Ile Leu Ser Leu Gly Thr Thr Ser Asn Arg Lys Ala Asn Thr
            1300                1305                1310 tcc aac tca aac gat caa ata gaa gat atc cct gtt ata gaa cta ggt      3984
Ser Asn Ser Asn Asp Gln Ile Glu Asp Ile Pro Val Ile Glu Leu Gly
        1315                1320                1325 aaa tat att aca gac act gtt tat gtt ggt gtt gaa caa agt tat tta      4032
Lys Tyr Ile Thr Asp Thr Val Tyr Val Gly Val Glu Gln Ser Tyr Leu
    1330                1335                1340 gat agt aat gat act ggg gca aga ata tca gtt gaa ctt gca cct aat      4080
Asp Ser Asn Asp Thr Gly Ala Arg Ile Ser Val Glu Leu Ala Pro Asn
1345                1350                1355                1360 ttt aat ctt gaa ggt aga aca ggg act caa tat agt gag ata ggt att      4128
Phe Asn Leu Glu Gly Arg Thr Gly Thr Gln Tyr Ser Glu Ile Gly Ile
                1365                1370                1375 aat tgg aaa aaa gat tat taa                                          4149
Asn Trp Lys Lys Asp Tyr
            1380

<210> SEQ ID NO 18
<211> LENGTH: 1382
<212> TYPE: PRT
<213> ORGANISM: Lawsonia intracellularis

<400> SEQUENCE: 18

Met Asn Asn Thr Lys Ile Leu Ser Lys Leu Leu Tyr Thr Leu Leu Gly
  1               5                  10                  15

Ala Phe Thr Leu Phe Leu Gly Leu Ile Ile Thr Gly Ile Leu Phe Ile
             20                  25                  30

Arg Thr Ser Thr Gly Ile Ala Trp Ile Lys Asn Thr Val Ser Ser Leu
         35                  40                  45

Leu Gln Gln Gln Gly Ile Ile Leu Gln Val Ser Ser Ile Ile Gly Pro
     50                  55                  60

Phe Pro Glu Gln Ile Thr Ile Asn Glu Leu Ser Leu Ser Asp Val Asn
 65                  70                  75                  80

Gly Thr Tyr Leu Thr Ile Ser Asn Leu Glu Ile Gln Ser Asn Leu Trp
                 85                  90                  95

Ala Leu Phe Lys Gly Gln Leu Glu Ile Leu Ser Phe Glu Leu Asn Asp
            100                 105                 110

Leu Val Leu Tyr Arg Leu Pro Ser Asn Asn Leu Lys Lys Ser Ser
        115                 120                 125

Thr Ser Phe Val Leu Pro His Ile Ser Phe Asp Leu Thr Pro Trp Trp
    130                 135                 140

Thr Glu His Ile Arg Ile Gln Asn Ile His Ile Asn Thr Gln Leu
145                 150                 155                 160

Ser Ser Asp Ile Ile Gly Ile Pro Leu Val Leu Ser Leu Glu Gly Asp
                165                 170                 175

Gly Thr Leu Thr Asn Trp Asn Gly Thr Phe Gln Leu Ser Ser Ser Asn
            180                 185                 190

Lys Thr Lys Ile Ile Gly Thr Leu Arg Tyr Gln Gly Asn Lys Thr Gln
        195                 200                 205

Phe Phe Glu Tyr Val His Pro Thr Arg Ile Val Thr Leu Glu Ile Asp
    210                 215                 220

Ser Val Ala Asp Lys Lys Ser Tyr Asn Asn Ser Ile Leu Glu Gln Pro
225                 230                 235                 240

Leu His Leu His Leu Ser Ile Tyr Pro Glu His Asn Arg Ile Ile Leu
                245                 250                 255
```

```
His Ser Leu Leu Ala Glu Tyr Gly Ser Trp Leu Leu Thr Ser Glu Ser
            260                 265                 270

Ile Glu Val Ser Asn Glu Gln Leu Lys Gly Asn Ile Leu Leu Lys Tyr
            275                 280                 285

Asn Gly Glu Ala Thr His Gln Leu Pro Ile Lys Lys Leu Asn Ser Ser
            290                 295                 300

Ile Thr Leu Ser Gly Ser Leu Asn Lys Pro Asn Phe Ser Ile Gln Met
305                 310                 315                 320

Thr Leu Pro Glu Ile Asn Ile Thr Lys Asn Ile Ile Asp Leu Gln Thr
                325                 330                 335

Glu Leu Val Ile Asn Leu Gly Leu Phe Ser Thr His Ser Asp Ile Leu
            340                 345                 350

Thr Ser Gly Thr Ile Thr Val Gln Gly Glu Thr Ile Pro Asn Ser Ile
            355                 360                 365

Leu Ser Ser Ala Val Asp Ile Ile Ala Ser Thr Thr Thr His Thr Ile
370                 375                 380

Thr Leu Glu His Ala Thr Leu Thr Ser Pro Glu Met His Phe Ser Leu
385                 390                 395                 400

Ser Gly Glu Phe Asn Ser Leu Leu Gly Asn Ile Asp Ala Asn Leu Lys
            405                 410                 415

Gly Asn Thr Pro Thr Leu Ser Ile Phe Ser Ser Leu Leu Gly Leu Pro
            420                 425                 430

Asp Leu Thr Gly Gln Ser Asn Ile Thr Ile Gly Leu His Arg Gln Gly
            435                 440                 445

Ser Ser Ser Ile Glu Gly Thr Ala Thr Val Ser Leu Asn Asn Met
450                 455                 460

Asn Trp Gly Val Gln Ala Leu Gln Gly Thr Leu Gly Asp Asn Ala Thr
465                 470                 475                 480

Leu Ser Gly Ile Tyr Asn Leu Thr Pro Ile Asp Trp Ser Ile Ser Leu
            485                 490                 495

Asn Lys Leu Lys Leu Thr Ala Lys Asn Val Tyr Ala Glu Gly Leu Ile
            500                 505                 510

Asn Phe Gln Lys Lys Tyr Ile Asp Ser Ser Ile Asn Leu Ile Ile Pro
            515                 520                 525

Asn Leu Gln Leu Ile Ala Pro Pro Ile Ser Gly Glu Leu Gln Ser Leu
            530                 535                 540

Ile Thr Val Ser Gly Lys Leu Asp Ala Pro Ser Ile Glu Ser Lys Ile
545                 550                 555                 560

Phe Ser Ser Gln Leu Thr Trp Asn Ala Leu Gln Leu Asn Asn Pro Gln
            565                 570                 575

Leu Ile Ile Thr Thr Thr Gln Ser Ser Ser Ala Ile Lys Gly Asn
            580                 585                 590

Ile Thr Leu Ser Ala Glu Pro Ala Ser Ser Glu Ala Leu Thr Phe Ser
            595                 600                 605

Ser Asn Trp Gly Ile Leu Pro Thr Glu Ile Leu Val Glu Lys Ile Ile
            610                 615                 620

Gly Asn Ile Leu Gly Val Asn Leu Asp Gly Asn Ile Lys Ile Thr Lys
625                 630                 635                 640

Lys Asp Tyr Leu Ile Asn Gly Asp Ile Ala Glu Val Gln Ser Trp
                645                 650                 655

Lys Asp Ile Ala Asn Ile Leu Gln Ile Pro Ile Arg Gly Ser Ala Ser
            660                 665                 670

Ile Lys Ile Gln Phe Asp Pro Lys Asn Gln Gln Cys Ile Ser Thr Gln
```

-continued

```
            675                 680                 685
Trp Gln Leu Lys Asn Phe Ile Leu Gly Asn Asn Phe Asn Val Thr Thr
    690                 695                 700

Ile Lys Gly Arg Ala Asp Thr Ile Gln Leu His Lys Asn Pro Thr Ile
705                 710                 715                 720

Ala Leu Ser Ser Lys Ile Gly Ala Gly Thr Tyr Glu Asp Phe Gln Trp
                725                 730                 735

Thr Gln Gly Thr Leu Asp Ile Lys Gly Thr Leu Lys Asn Phe Asn Ser
                740                 745                 750

Lys Ile Asn Ile Ala Gly Gln Thr Thr Val Asn Ala Asn Phe Gln Thr
                755                 760                 765

Asn Leu Phe Glu Lys Asn Ile Asn Ile Thr Thr Leu Asn Leu Lys Asn
    770                 775                 780

Ile Gln Lys Asn Ile Gly Ile Lys Leu Leu Gln Pro Ile Lys Ile Ile
785                 790                 795                 800

Val Ser Pro Gln Gln Phe Val Leu Asn Asn Cys Ser Leu Ala Ile Leu
                805                 810                 815

Pro Ser Gly Thr Ile Thr Thr Asp Ile Tyr Val Thr Pro Gln Arg Leu
                820                 825                 830

Asn Ala Asn Ala Ile Ile Lys Glu Val Ser Leu Leu Ser Phe Gln Pro
                835                 840                 845

Phe Ser Ile Leu Leu Pro Gln Gly Asn Ile Asn Gly His Ile Thr Leu
    850                 855                 860

Thr Gly Ile Pro Ser Lys Pro Lys Gly Thr Leu Ser Phe Asp Ile Leu
865                 870                 875                 880

Asn Ile His Tyr Pro Arg Pro Asn Pro Ser Ile Ala Asn Leu His Val
                885                 890                 895

Glu Gly Glu Ile Ile Ser Ser Pro Asn Asn Ile Cys Lys Leu Asn Ala
                900                 905                 910

Thr Leu Thr Glu Lys Lys Glu Pro Ile Pro Ile Ser Ile Gln Ala Thr
                915                 920                 925

Leu Pro Phe Glu Phe Thr Glu Asn Asn Ile Pro Met Leu Ser Lys Met
    930                 935                 940

Arg Pro Phe Ser Ala His Ile Lys Trp Thr Gly Ile Leu Asp Thr Leu
945                 950                 955                 960

Trp Lys Leu Ile Pro Leu Thr Asp Tyr Ile Met Ala Gly Asn Gly Ser
                965                 970                 975

Leu Asp Ala Ser Leu Ser Gly Thr Leu Asp Ser Pro Thr Tyr Ala Ile
                980                 985                 990

Ile Thr Thr Leu Ser Asn Ala Asn Phe Gln Asp Leu Ser Leu Gly Leu
                995                 1000                1005

Tyr Leu Glu Asn Ile Asn Ala Lys Leu Gln Val Phe Ser Asn Arg Ile
    1010                1015                1020

Ser His Ile Gln Ala Thr Ala Ser Asp Gly Lys Gln Gly Ser Ile Gln
1025                1030                1035                1040

Leu Ile Gly Asn Ile Gly Ser Ser Lys Glu His Phe Pro Leu Ser Ile
                1045                1050                1055

Asn Gly Ser Phe Thr Asn Leu Ala Pro Leu Gln Arg Lys Asp Leu Ser
                1060                1065                1070

Leu Thr Leu Ser Gly Ala Ala Thr Leu Glu Gly Thr Leu Lys Gln Ser
                1075                1080                1085

Glu Val Lys Gly Asp Ile Val Ile Asn Gln Gly Glu Phe Gln Leu Thr
                1090                1095                1100
```

-continued

Glu Gly Leu Thr Ser Asn Ile Pro Thr Leu Asn Val Val Asp Ser Thr
1105                1110                1115                1120

Gln Gln Gln Asn Thr Lys Thr Lys Lys Ala Thr Tyr Gln Gln Pro Thr
            1125                1130                1135

Leu Ser Ile Ala Leu Ser Ile Pro Asn Arg Phe Phe Val Arg Ser Ser
        1140                1145                1150

Met Phe Glu Ser Glu Trp Gly Gly Asn Leu Thr Ile Asn Lys Val Ile
        1155                1160                1165

Thr Ser Pro Val Ile Thr Gly Ala Leu Thr Ser Ile Arg Gly Asn Phe
    1170                1175                1180

Asn Leu Leu Gly Lys Gln Phe Ser Leu Ala Lys Ser Thr Ile Ser Phe
1185                1190                1195                1200

Ser Gly Ser Val Pro Pro Asn Pro Leu Leu Asn Ile Ser Leu Thr Tyr
            1205                1210                1215

Ser Ser Pro Ser Ile Thr Ala Ile Gly Ile Ile Lys Gly Thr Thr Ser
            1220                1225                1230

Asn Pro Asn Ile Thr Phe Ser Ser Thr Pro Pro Leu Pro Gln Asp Glu
            1235                1240                1245

Ile Val Ser Gln Val Leu Phe Gly Lys Ser Ser Gln Ser Leu Ser Arg
    1250                1255                1260

Ile Gln Ala Ile Gln Leu Ala Gln Glu Leu Ala Asn Leu Thr Gly Phe
1265                1270                1275                1280

Asn Thr Gly Ser Met Asn Phe Leu Thr Asn Ile Arg Gln Thr Leu Gly
            1285                1290                1295

Leu Asp Ile Leu Ser Leu Gly Thr Thr Ser Asn Arg Lys Ala Asn Thr
            1300                1305                1310

Ser Asn Ser Asn Asp Gln Ile Glu Asp Ile Pro Val Ile Glu Leu Gly
            1315                1320                1325

Lys Tyr Ile Thr Asp Thr Val Tyr Val Gly Val Glu Gln Ser Tyr Leu
    1330                1335                1340

Asp Ser Asn Asp Thr Gly Ala Arg Ile Ser Val Glu Leu Ala Pro Asn
1345                1350                1355                1360

Phe Asn Leu Glu Gly Arg Thr Gly Thr Gln Tyr Ser Glu Ile Gly Ile
            1365                1370                1375

Asn Trp Lys Lys Asp Tyr
            1380

<210> SEQ ID NO 19
<211> LENGTH: 26
<212> TYPE: DNA
<213> ORGANISM: Artificial Sequence
<220> FEATURE:
<223> OTHER INFORMATION: Oligonucleotide probe/primer

<400> SEQUENCE: 19
catattcaag gtacagcatc tgatgg                                    26

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide probe/primer

<400> SEQUENCE: 20
ctcctttaca aaccttgctc c                                         21

<210> SEQ ID NO 21
<211> LENGTH: 22
<212> TYPE: DNA
<213> ORGANISM: Artificial Sequence
<220> FEATURE:
<223> OTHER INFORMATION: Oligonucleotide probe/primer

<400> SEQUENCE: 21
gctcatctaa agaacacttt cc                    22

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide probe/primer

<400> SEQUENCE: 22
caaggtagta tacaacttat tgg                   23

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide probe/primer

<400> SEQUENCE: 23
gacctaagtc ttacactttc agg                   23

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide probe/primer

<400> SEQUENCE: 24
gtattaatac tacattagtt gacg                  24

<210> SEQ ID NO 25
<211> LENGTH: 21
<212> TYPE: DNA
<213> ORGANISM: Artificial Sequence
<220> FEATURE:
<223> OTHER INFORMATION: Oligonucleotide probe/primer

<400> SEQUENCE: 25
ggataataat ggaaaaagtg g                     21

<210> SEQ ID NO 26
<211> LENGTH: 22
<212> TYPE: DNA
<213> ORGANISM: Artificial Sequence
<220> FEATURE:
<223> OTHER INFORMATION: Oligonucleotide probe/primer

<400> SEQUENCE: 26
caagcaatgc ctgtagaggt cc                    22

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide probe/primer

```
<400> SEQUENCE: 27
aagaatgcct gtaataataa gtcc                                          24

<210> SEQ ID NO 28
<211> LENGTH: 19
<212> TYPE: DNA
<213> ORGANISM: Artificial Sequence
<220> FEATURE:
<223> OTHER INFORMATION: Oligonucleotide probe/primer

<400> SEQUENCE: 28
ttggggaatc ctacctacg                                                19

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide probe/primer

<400> SEQUENCE: 29
tattaggagt aaatcttgat g                                             21

<210> SEQ ID NO 30
<211> LENGTH: 22
<212> TYPE: DNA
<213> ORGANISM: Artificial Sequence
<220> FEATURE:
<223> OTHER INFORMATION: Oligonucleotide probe/primer

<400> SEQUENCE: 30
gcaggacaaa caactgtaaa cg                                            22

<210> SEQ ID NO 31
<211> LENGTH: 22
<212> TYPE: DNA
<213> ORGANISM: Artificial Sequence
<220> FEATURE:
<223> OTHER INFORMATION: Oligonucleotide probe/primer

<400> SEQUENCE: 31
gaggaagaag tatactaaat gg                                            22

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide probe/primer

<400> SEQUENCE: 32
tgttggacta tctaaagtcc                                               20

<210> SEQ ID NO 33
<211> LENGTH: 22
<212> TYPE: DNA
<213> ORGANISM: Artificial Sequence
<220> FEATURE:
<223> OTHER INFORMATION: Oligonucleotide probe/primer

<400> SEQUENCE: 33
ctattgatgg atttggcctt gg                                            22

<210> SEQ ID NO 34
```

```
<211> LENGTH: 20
<212> TYPE: DNA
<213> ORGANISM: Artificial Sequence
<220> FEATURE:
<223> OTHER INFORMATION: Oligonucleotide probe/primer

<400> SEQUENCE: 34
gtgctggtac atatgaagac                                              20

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide probe/primer

<400> SEQUENCE: 35
ttcatcacct tctattacag                                              20

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide probe/primer

<400> SEQUENCE: 36
ggaaactatt tcatcttgag                                              20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide probe/primer

<400> SEQUENCE: 37
attaggtgca agttcaactg                                              20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide probe/primer

<400> SEQUENCE: 38
tttagatagt aatgatactg                                              20

<210> SEQ ID NO 39
<211> LENGTH: 36
<212> TYPE: DNA
<213> ORGANISM: Artificial Sequence
<220> FEATURE:
<223> OTHER INFORMATION: Oligonucleotide probe/primer

<400> SEQUENCE: 39
ttattatatt atgtttttg taatgttaat ttcagg                             36

<210> SEQ ID NO 40
<211> LENGTH: 28
<212> TYPE: DNA
<213> ORGANISM: Artificial Sequence
<220> FEATURE:
<223> OTHER INFORMATION: Oligonucleotide probe/primer

<400> SEQUENCE: 40
```

-continued

```
gacatatgaa taacacaaaa atactttc                                   28

<210> SEQ ID NO 41
<211> LENGTH: 41
<212> TYPE: DNA
<213> ORGANISM: Artificial Sequence
<220> FEATURE:
<223> OTHER INFORMATION: Oligonucleotide probe/primer

<400> SEQUENCE: 41
gaggatcctc tagagttaat caaactgtat ttttattgat g                    41

<210> SEQ ID NO 42
<211> LENGTH: 31
<212> TYPE: DNA
<213> ORGANISM: Artificial Sequence
<220> FEATURE:
<223> OTHER INFORMATION: Oligonucleotide probe/primer

<400> SEQUENCE: 42
gacatatgcg gacctctaca ggcattgctt g                               31

<210> SEQ ID NO 43
<211> LENGTH: 24
<212> TYPE: DNA
<213> ORGANISM: Artificial Sequence
<220> FEATURE:
<223> OTHER INFORMATION: Oligonucleotide probe/primer

<400> SEQUENCE: 43
gatcaggtag tccaagaaga gaag                                       24

<210> SEQ ID NO 44
<211> LENGTH: 45
<212> TYPE: DNA
<213> ORGANISM: Artificial Sequence
<220> FEATURE:
<223> OTHER INFORMATION: Oligonucleotide probe/primer

<400> SEQUENCE: 44
ttggaggatc ctctagagtt atcaggttgt aattgttcca gatgg                45

<210> SEQ ID NO 45
<211> LENGTH: 21
<212> TYPE: DNA
<213> ORGANISM: Artificial Sequence
<220> FEATURE:
<223> OTHER INFORMATION: Oligonucleotide probe/primer

<400> SEQUENCE: 45
ccttggttaa taacaatatc g                                          21

<210> SEQ ID NO 46
<211> LENGTH: 23
<212> TYPE: DNA
<213> ORGANISM: Artificial Sequence
<220> FEATURE:
<223> OTHER INFORMATION: Oligonucleotide probe/primer

<400> SEQUENCE: 46
caactccact tcaagataga agc                                        23

<210> SEQ ID NO 47
<211> LENGTH: 29
<212> TYPE: DNA
```

```
<213> ORGANISM: Artificial Sequence
<220> FEATURE:
<223> OTHER INFORMATION: oligo

<400> SEQUENCE: 47
gaccatggaa aaagtatgtt attttttc                                             29

<210> SEQ ID NO 48
<211> LENGTH: 36
<212> TYPE: DNA
<213> ORGANISM: Artificial Sequence
<220> FEATURE:
<223> OTHER INFORMATION: oligo

<400> SEQUENCE: 48
gaggatcctc tagagttaga atgcttgccc aatact                                    36

<210> SEQ ID NO 49
<211> LENGTH: 39
<212> TYPE: DNA
<213> ORGANISM: Artificial Sequence
<220> FEATURE:
<223> OTHER INFORMATION: oligo

<400> SEQUENCE: 49
ttggaggatc ctctagagtt agaatgcttg cccaatact                                 39

<210> SEQ ID NO 50
<211> LENGTH: 32
<212> TYPE: DNA
<213> ORGANISM: Artificial Sequence
<220> FEATURE:
<223> OTHER INFORMATION: oligo

<400> SEQUENCE: 50
ttgaccatgg ctacatcaat taccacttcc ac                                        32

<210> SEQ ID NO 51
<211> LENGTH: 29
<212> TYPE: DNA
<213> ORGANISM: Artificial Sequence
<220> FEATURE:
<223> OTHER INFORMATION: oligo

<400> SEQUENCE: 51
ggacatatga ataacacaaa aatactttc                                            29

<210> SEQ ID NO 52
<211> LENGTH: 44
<212> TYPE: DNA
<213> ORGANISM: Artificial Sequence
<220> FEATURE:
<223> OTHER INFORMATION: oligo

<400> SEQUENCE: 52
ttggaggatc ctctagagtt aatcaaactg tatttttatt gatg                           44

<210> SEQ ID NO 53
<211> LENGTH: 32
<212> TYPE: DNA
<213> ORGANISM: Artificial Sequence
<220> FEATURE:
<223> OTHER INFORMATION: oligo

<400> SEQUENCE: 53
ggacatatgc ggacctctac aggcattgct tg                                        32
```

```
<210> SEQ ID NO 54
<211> LENGTH: 20
<212> TYPE: DNA
<213> ORGANISM: Artificial Sequence
<220> FEATURE:
<223> OTHER INFORMATION: oligo

<400> SEQUENCE: 54
tgaggattat taagttggag                                                     20

<210> SEQ ID NO 55
<211> LENGTH: 20
<212> TYPE: DNA
<213> ORGANISM: Artificial Sequence
<220> FEATURE:
<223> OTHER INFORMATION: oligo

<400> SEQUENCE: 55
gcatgcaacc ttaacatctc                                                     20

<210> SEQ ID NO 56
<211> LENGTH: 20
<212> TYPE: DNA
<213> ORGANISM: Artificial Sequence
<220> FEATURE:
<223> OTHER INFORMATION: oligo

<400> SEQUENCE: 56
tttctgatgt aagtaaccag                                                     20

<210> SEQ ID NO 57
<211> LENGTH: 20
<212> TYPE: DNA
<213> ORGANISM: Artificial Sequence
<220> FEATURE:
<223> OTHER INFORMATION: oligo

<400> SEQUENCE: 57
tctgcccata tcaagtggac                                                     20

<210> SEQ ID NO 58
<211> LENGTH: 20
<212> TYPE: DNA
<213> ORGANISM: Artificial Sequence
<220> FEATURE:
<223> OTHER INFORMATION: oligo

<400> SEQUENCE: 58
ggaacatttc aactatcctc                                                     20

<210> SEQ ID NO 59
<211> LENGTH: 20
<212> TYPE: DNA
<213> ORGANISM: Artificial Sequence
<220> FEATURE:
<223> OTHER INFORMATION: oligo

<400> SEQUENCE: 59
gtaaggtaag ttccattcac                                                     20

<210> SEQ ID NO 60
<211> LENGTH: 25
<212> TYPE: DNA
<213> ORGANISM: Artificial Sequence
<220> FEATURE:
```

<223> OTHER INFORMATION: oligo

<400> SEQUENCE: 60
caacgtggat ccgaattcaa gcttc        25

<210> SEQ ID NO 61
<211> LENGTH: 16
<212> TYPE: PRT
<213> ORGANISM: Artificial Sequence
<220> FEATURE:
<223> OTHER INFORMATION: Peptide

<400> SEQUENCE: 61

Met Gly Ser Gly Ser Gly Asp Asp Asp Lys Leu Ala Leu Leu Thr
1               5                   10                  15

<210> SEQ ID NO 62
<211> LENGTH: 7
<212> TYPE: PRT
<213> ORGANISM: Artificial Sequence
<220> FEATURE:
<223> OTHER INFORMATION: Peptide

<400> SEQUENCE: 62

Ala Thr Ser Ile Thr Thr Ser
1               5

<210> SEQ ID NO 63
<211> LENGTH: 45
<212> TYPE: PRT
<213> ORGANISM: Artificial Sequence
<220> FEATURE:
<223> OTHER INFORMATION: Peptide

<400> SEQUENCE: 63

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met
        35                  40                  45

<210> SEQ ID NO 64
<211> LENGTH: 50
<212> TYPE: PRT
<213> ORGANISM: Artificial Sequence
<220> FEATURE:
<223> OTHER INFORMATION: Peptide

<400> SEQUENCE: 64

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Asp Ile
        35                  40                  45

Gly Ser
    50

<210> SEQ ID NO 65
<211> LENGTH: 7
<212> TYPE: PRT
<213> ORGANISM: Artificial Sequence
<220> FEATURE:

-continued

```
<223> OTHER INFORMATION: Peptide

<400> SEQUENCE: 65

Glu Phe Asn Leu Ser Lys Gly
1               5

<210> SEQ ID NO 66
<211> LENGTH: 17
<212> TYPE: PRT
<213> ORGANISM: Artificial Sequence
<220> FEATURE:
<223> OTHER INFORMATION: Peptide

<400> SEQUENCE: 66

Met Gly Ser Gly Ser Gly Asp Asp Asp Lys Leu Ala Leu Gly His
1               5                   10                  15

Met

<210> SEQ ID NO 67
<211> LENGTH: 7
<212> TYPE: PRT
<213> ORGANISM: Artificial Sequence
<220> FEATURE:
<223> OTHER INFORMATION: Peptide

<400> SEQUENCE: 67

Arg Thr Ser Thr Gly Ile Ala
1               5

<210> SEQ ID NO 68
<211> LENGTH: 21
<212> TYPE: PRT
<213> ORGANISM: Artificial Sequence
<220> FEATURE:
<223> OTHER INFORMATION: Peptide

<400> SEQUENCE: 68

Asp Pro Asn Ser Ser Ser Val Asp Lys Leu Ala Ala Ala Leu Glu His
1               5                   10                  15

His His His His His
            20
```